US008858991B2

(12) United States Patent
McKearn et al.

(10) Patent No.: US 8,858,991 B2
(45) Date of Patent: Oct. 14, 2014

(54) DELAYED RELEASE ORAL PHARMACEUTICAL DOSAGE FORMS COMPRISING MGBG

(75) Inventors: John McKearn, Saint Louis, MO (US); Jeremy Blitzer, Sunnyvale, CA (US)

(73) Assignee: Pathologica LLC, Burlingame, CA (US)

( * ) Notice: Subject to any disclaimer, the term of this patent is extended or adjusted under 35 U.S.C. 154(b) by 0 days.

(21) Appl. No.: 13/354,076

(22) Filed: Jan. 19, 2012

(65) Prior Publication Data
US 2012/0269891 A1 Oct. 25, 2012

Related U.S. Application Data

(60) Provisional application No. 61/434,269, filed on Jan. 19, 2011.

(51) Int. Cl.
| | | |
|---|---|---|
| *A61K 31/132* | (2006.01) |
| *A61K 9/20* | (2006.01) |
| *A61K 9/28* | (2006.01) |
| *A61K 9/50* | (2006.01) |
| *A61K 9/48* | (2006.01) |
| *C07C 211/13* | (2006.01) |
| *C07C 243/16* | (2006.01) |
| *C07C 251/12* | (2006.01) |
| *C07C 251/78* | (2006.01) |

(52) U.S. Cl.
CPC ............ *A61K 9/2054* (2013.01); *C07C 251/12* (2013.01); *C07C 251/78* (2013.01); *C07C 243/16* (2013.01); *C07C 211/13* (2013.01); *A61K 9/4808* (2013.01); *A61K 9/2846* (2013.01); *A61K 9/5026* (2013.01); *A61K 9/5047* (2013.01)

USPC ........... 424/451; 424/457; 424/459; 424/462; 424/463; 424/464; 424/468; 424/474; 424/482; 564/227; 564/250; 514/634; 514/639; 514/451; 514/457; 514/459; 514/462; 514/463; 514/464; 514/468; 514/474; 514/482

(58) Field of Classification Search
USPC ......... 424/451, 457, 459, 462, 463, 464, 468, 424/474, 482; 564/227, 250; 514/634, 639
See application file for complete search history.

(56) References Cited

U.S. PATENT DOCUMENTS 5,614,557 A     3/1997   Bey
7,445,794 B1 * 11/2008   Newell et al. ................ 424/450
(Continued)

FOREIGN PATENT DOCUMENTS

EP          2283830 A1 * 2/2011 ............... A61K 9/48
WO    2011009039 A2    1/2011

OTHER PUBLICATIONS

Freedlander et al., "Carcinostatic Action of Polycarbonyl Compounds and Their Derivatives, II. Glyoxal Bis(Guanylhydrazone) and Derivatives," 1958, Cancer Research, 18(4):360-363.*

(Continued)

*Primary Examiner* — Jane C Oswecki
(74) *Attorney, Agent, or Firm* — Cynthia Hathaway; Dennis A. Bennett

(57) ABSTRACT

Disclosed herein are controlled-release oral pharmaceutical dosage forms comprising MGBG, and their application for the improved treatment of diseases with reduced side effects and/or longer time at maximum concentration.

6 Claims, 5 Drawing Sheets

(56) References Cited

U.S. PATENT DOCUMENTS

| | | | |
|---|---|---|---|
| 8,258,186 | B2 | 9/2012 | McKearn et al. |
| 8,445,540 | B2 | 5/2013 | Hadlock et al. |
| 2005/0159493 | A1 | 7/2005 | McGrath |
| 2007/0078187 | A1* | 4/2007 | McGrath et al. ............. 514/611 |
| 2008/0262092 | A1 | 10/2008 | Hadlock |
| 2011/0112199 | A1 | 5/2011 | McKearn |

OTHER PUBLICATIONS

Herr, H.W., "Phase I trial of alpha-difluoromethyl ornithine (DFMO) and methylglyoxyal bis(guanylhydrazone) (MGBG) in patients with advanced prostate cancer," 1986, Urology, 28(6):508-511.*

Freedlander, B.L., Carcinostatic Action of Polycarbonyl Compounds and Their Derivatives III. Hydroxymethylglyoxal Bis(guanylhydrazone), Cancer Res. (1958) vol. 18 December (No. 12): 1286-89.

Freedlander, B.L., Carcinostatic Action of Polycarbonyl Compounds and Their Derivatives II. Glyoxal Bis (Guanylhydrazone) and Derivatives, Cancer Res. (1958) vol. 18, April, (No. 4): 360-63.

Regelson, William, Initial clinical study of parenteral methylglyoxal bis(guanylhydrazone) diacetate., Cancer Chemother Repts, (1961) vol. 11, pp. 81-86.

E. Mihich, C.L., Pharmacology of Methylglyoxal-bis-(guanylhydrazone) (CH3-G) I. Toxic and Pathologic Effects, Cancer Res, (1962) vol. 22, September (No. 9) pp. 962-972 (plus figs).

Regelson, William, Clinical experience with methylglyoxal bis(guanylhydrazone) dihydrochloride: A new agent with clinical activity in acute myelocytic leukemia and the lymphomas., Cancer Chemother Repts, (1963) vol. 27, pp. 15-26.

Mihich, Enrico, Current Studies with Methylglyoxal-bis(guanylhydrazone), Cancer Res, (1963) vol. 23, September (No. 9) pp. 1375-1389.

Freireich, B.L., Methylglyoxal bis (guanylhydrazone) A new agent active against acute myelocytic leukemia., Cancer Chemother Repts, (1962) vol. 16, pp. 183-186. Meeting Info.: Second Conference Experimental Clinical Cancer Chemotherapy, Washington, D.C., Nov. 1961.

Levin, Robert H., Different patterns of remission in acute myelocytic leukemia. A comparison of the effects of the methylglyoxal bis(guanylhydrazone) and 6-mercaptopurine, Blood (1963), 21, 689-98 CODEN: BLOOAW; ISSN: 0006-4971.

Liesmann, J., Pharmaco Kinetics of Methyl Glyoxal Bis Guanyl Hydrazone, Proceedings of the American Association for Cancer Research and American Society of Clinical Oncology, (1980) vol. 21, pp. 151. Meeting Info.: 71st Annual Meeting of the American Association for Cancer Research, San Diego, Calif., USA, May 28-31, 1980. Proc Am Assoc Cancer Res Am Soc Clin Oncol.

Siimes, M., Synergistic Action of 2 Polyamine Anti Metabolites leads to a Rapid Therapeutic Response in Childhood Leukemia, International Journal of Cancer, (1981) vol. 28, No. 5, pp. 567-570. CODEN: IJCNAW. ISSN: 0020-7136.

Takami, H., Experimental chronochemotherapy with methylglyoxal bis-(guanylhydrazone) (methyl-GAG)., Proceedings of the American Association for Cancer Research, (1981) vol. vol. 22, pp. 882. CODEN: PAACA3.

Jensen, B. Dialyzability of Methyl Glyoxal Bis Guanyl Hydrazone, Cancer Treatment Reports, (1983) vol. 67, No. 3, pp. 283-284. CODEN: CTRRDO. ISSN: 0361-5960.

Herr, H.W., Phase I trial of alpha-difluoromethyl ornithine (DFMO) and methylglyoxal bis (guanylhydrazone) (MGBG) in patients with advanced prostatic cancer., Urology, (1986) vol. 28, No. 6, pp. 508-511. ISSN: 0090-4295 CODEN: URGYAZ.

Dunzendorfer, U., Some aspects of clearance of mitoguazone in cancer patients and experimental cancer models, Arzneimittel-Forschung (1986), 36(3), 506-8 CODEN: ARZNAD; ISSN: 0004-4172.

Maddox, A.M., Polyamines increase in human peripheral blood and bone marrow mononuclear cells following administration of methylglyoxal bis(guanylhydrazone)., Chemotherapy, (1988) vol. 34, No. 5, pp. 419-429. Journal code: 0144731. ISSN: 0009-3157.

Oliverio, Vincent, Distribution, excretion, and metabolism of methylglyoxal bisguanylhydrazone-14C, Journal of Pharmacology and Experimental Therapeutics (1963), 141(2), 149-56 CODEN: JPETAB; ISSN: 0022-3565.

Mihich, E., Anti-Tumor Effects and Toxicology of Methylglyoxal Bis (Guanylhydrazone),, Proc. Nat. Acad. Sciences Abstracts 1959.

WO2011009039, Pathologica, LLC, International Search Report, Publication Date Jan. 20, 2011.

WO2011009039, Pathologica, LLC, Written Opinion, Publication Date Jan. 20, 2011.

U.S. Appl. No. 13/865,816 , not yet published.

Prosecution file history of US20110112199A1.

* cited by examiner

DELAYED RELEASE ORAL PHARMACEUTICAL DOSAGE FORMS COMPRISING MGBG

This application claims the benefit of priority of U.S. provisional application No. 61/434,269, filed Jan. 19, 2011, the disclosure of which is incorporated by reference as if written herein in its entirety.

This invention was made with government support under Grant Number U19 MH081835 awarded by the National Institutes of Health. The government has certain rights in the invention.

Disclosed herein are controlled-release oral pharmaceutical dosage forms comprising MGBG, and their application for the improved treatment of diseases with reduced side effects.

MGBG (methylglyoxal bis(guanylhydrazone); mitoguazone) is a competitive inhibitor of S-adenosyl methionine decarboxylase (AMD-I), which catalyzes the synthesis of spermidine (a polyamine). The amino acid-derived polyamines have long been associated with cell growth and cancer, and specific oncogenes and tumor-suppressor genes regulate polyamine metabolism. Inhibition of polyamine biosynthesis has proven to be generally ineffective as an anticancer strategy in clinical trials, but it is a potent cancer chemoprevention strategy in preclinical studies. Despite its novel mechanism of action and promising preclinical data, initial clinical trials of MGBG were ceased in the middle of 1960s due to severe toxicity particularly to self-renewing tissues including bone marrow and intestinal tract (e.g. severe mucositis), which were both dose- and schedule-dependent.

Regardless, research continued with MGBG. A number of studies have examined potential uses in combination with other chemotherapeutic agents and innovative dosing regimens, designed to minimize side effects and dose where possible. Others have focused on elucidating MGBG's modes of action in the body. Yet others have investigated MGBG's activity in diseases other than cancer.

Perhaps due to the negative clinical findings coupled with a lack of demonstrated oral bioavailability in these early studies, MGBG has been confined to intravenous use to date. As a practical matter, this presents a number of problems for the treatment of many diseases, particularly chronic or recurrent conditions. Administration via IV injection or infusion must be done by a medical professional in a hospital setting. This not only presents an inconvenience and increased cost to the subject, but it also exposes him or her to hospital-based infections and illnesses, the latter both from venipuncture and the hospital or clinic visit itself. In immunocompromised individuals such as, for example, those with HIV or AIDS, individuals undergoing treatment with immunosuppressive agents, and the elderly, this is a relevant concern. Thus, a subject with a long-term chronic condition such as an autoimmune or hyperproliferative disorder, or a doctor treating such a subject, might find the cost, inconvenience, and risks of such a treatment more important than any potential therapeutic benefits the drug might offer.

An oral formulation of MGBG, in contrast, presents several benefits. First, an oral formulation, for example a simple capsule or tablet, may be taken outside of a hospital setting, increasing the potential for ease of use and compliance. This permits a subject to avoid infection risks concomitant with IV administration and hospital visits. Where early treatment can prevent the development of disease complications, this is of particular benefit. Chronic low-dose administration of MGBG is practically impossible in an IV formulation. Additionally, oral delivery typically avoids the high concentration peak and rapid clearance associated with an IV bolus dose. Yet another advantage of an oral drug would be the ability to formulate MGBG as a combination composition with one or more other therapeutic agents.

However, because gastrointestinal side effects have been reported in the course of oral MGBG therapy, and because these side effects have been reported to increase in frequency and severity with dose, dose-limiting oral GI toxicity is cause for concern. Additionally, in prior studies a correlation was observed across species whereby as body surface area increases, $T_{max}$ declines and $C_{max}$ increases, culminating in immediate gastric irritation/emesis in dogs; see, e.g., FIG. 1. Of concern was whether humans would have a similar reaction to the drug. Dosage forms in which the location within the GI tract and the timing of release of the drug are controlled, for example delayed-release formulations, represent a practical solution in the event that GI toxicity becomes a problem in the clinic.

Accordingly, disclosed herein are controlled-release oral pharmaceutical dosage forms comprising MGBG for the treatment of disease.

Figure 1:
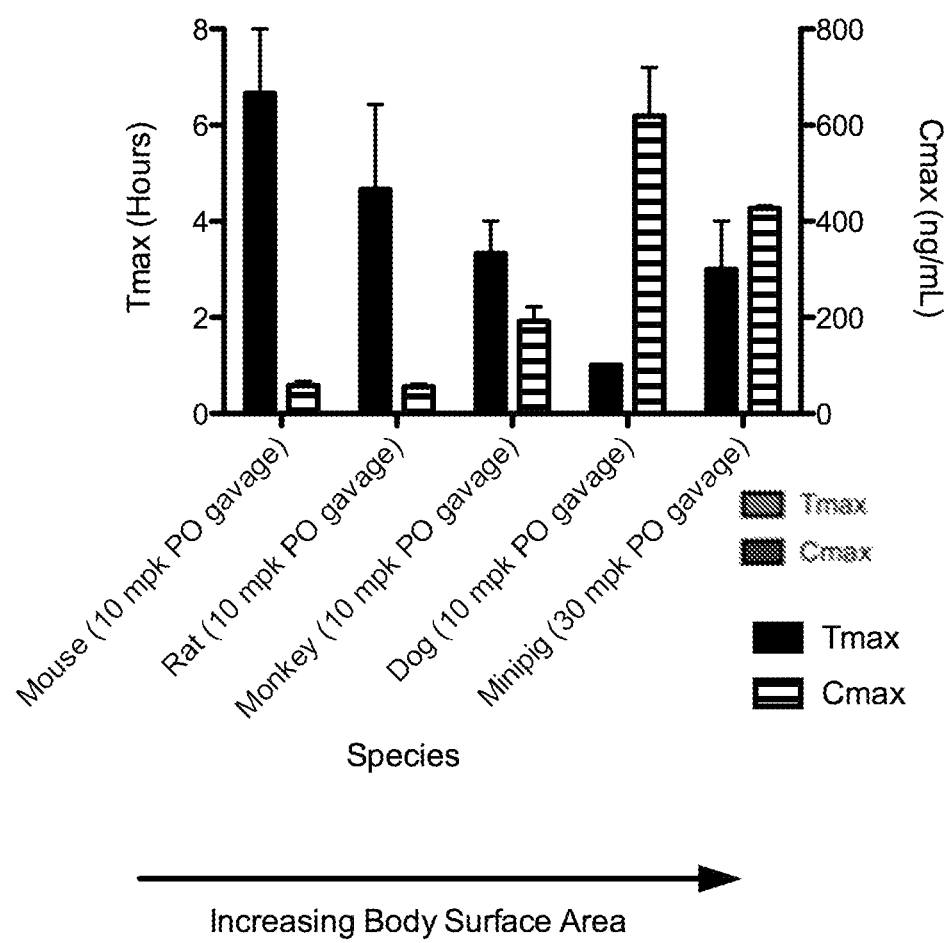
FIG. 1 depicts a graph showing that as body surface area increases across species administered MGBG, $T_{max}$ drops while $C_{max}$ increases.

Provided herein is a controlled-release oral pharmaceutical dosage form comprising MGBG.

In certain embodiments, the controlled-release dosage form comprising MGBG is chosen from extended-release, sustained release, delayed release, and pulsed-release.

In certain embodiments, the controlled-release dosage form comprising MGBG is a delayed-release tablet or a delayed-release capsule.

Also provided a delayed-release tablet or a delayed-release capsule comprising MGBG, wherein the capsule or tablet comprises an enteric coating.

In certain embodiments, the enteric coating comprises one or more of cellulose acetate phthalate (CAP), cellulose acetate succinate, hydroxy propyl methyl cellulose phthalate, hydroxy propyl methyl cellulose acetate succinate (hypromellose acetate succinate), polyvinyl acetate phthalate (PVAP), methacrylic acid/methyl methacrylate copolymer, methacrylic acid/methyl acrylate copolymers, methacrylic acid/ethyl acrylate copolymer, sodium alginate and stearic acid.

In certain embodiments, the enteric coating applied to the tablet.

In certain embodiments, the enteric coating applied to the capsule.

In certain embodiments, the enteric coating comprises a methacrylic acid/ethyl acrylate copolymer.

In certain embodiments, the methacrylic acid/ethyl acrylate copolymer is EUDRAGIT® L100-55.

In certain embodiments, the enteric coating begins to substantially dissolve, and drug release commences, in the duodenum.

In certain embodiments, the enteric coating begins to substantially dissolve and drug release commences at about ½ or more hours after ingestion.

In certain embodiments, the enteric coating begins to substantially dissolve and drug release commences at about 1 or more hours after ingestion.

In certain embodiments, enterically-coated capsule comprising MGBG exhibits reduced side effects in patients compared to a non-enterically-coated capsule. In certain embodiments, said side effects are reduced by at least 30%, at least 40%, least 50%, at least 55%, at least 60%, at least 65%, at least 70%, at least 75%, at least 80%, at least 85%, or at least 90% compared to a non-enterically-coated capsule. In certain embodiments, it is the overall incidence of said side effects that is reduced. In other embodiments, it is the severity of said side effects that is reduced. In certain embodiments, both the incidence and severity of said side effects are reduced.

In certain embodiments is provided an enterically-coated capsule which does not have substantially dose-limiting side effects.

In certain embodiments, said side effects are gastrointestinal.

In certain embodiments is provided an enterically-coated capsule comprising MGBG which exhibits reduced side effects in patients compared to a non-enterically-coated capsule and is orally bioavailable. In certain embodiments, the percent bioavailability is between about 10 and about 50%. In certain embodiments, the percent bioavailability is between about 20 and about 40%. In certain embodiments, the percent bioavailability is between about 30 and about 40%. In certain embodiments, the percent bioavailability is about 35%.

In certain embodiments, said gastrointestinal side effects are chosen from nausea, emesis (vomiting), diarrhea, abdominal pain, oral mucositis, oral ulceration, pharyngitis, stomatitis, irritation of the gastric mucosa, and gastrointestinal ulceration.

In certain embodiments, emesis is reduced by at least at least 30%, at least 40%, least 50%, at least 55%, at least 60%, at least 65%, at least 70%, at least 75%, at least 80%, at least 85%, or at least 90% compared to a reference standard that is not enterically coated. In certain embodiments, emesis is reduced by at least 50% compared to a reference standard that is not enterically coated. In certain embodiments, emesis is reduced by at least 70% compared to a reference standard that is not enterically coated. In certain embodiments, emesis is reduced by at least 80% compared to a reference standard that is not enterically coated. In certain embodiments, emesis is reduced by at least 90% compared to a reference standard that is not enterically coated.

In certain embodiments, said gastrointestinal side effects are chosen from inhibition of gastrointestinal mucosal proliferation, inhibition of migration of developing epithelial lumen cells, and inhibition of differentiation of stem or progenitor cells into epithelial lumen cells.

In certain embodiments is provided an enterically-coated capsule which exhibits dose-proportional increases in $C_{max}$ and AUC.

In certain embodiments is provided an enterically-coated capsule which exhibits a half life comparable to a reference standard that is not enterically coated.

In certain embodiments is provided a tablet additionally comprising a seal coating between the tablet and the enteric coating.

In certain embodiments is provided a tablet additionally comprising an extended release coating.

In certain embodiments is provided a tablet additionally comprising an immediate release coating containing MGBG atop the extended-release coating.

In certain embodiments, the enteric coating is applied to micropellets comprising MGBG optionally with one or more excipients, and the micropellets are enclosed in a capsule.

In certain embodiments, the enteric coating is applied to spheroids comprising MGBG optionally with one or more excipients, and the spheroids are enclosed in a capsule.

In certain embodiments, the enteric coating is applied to the capsule.

In certain embodiments, the enteric coating comprises a methacrylic acid/ethyl acrylate copolymer.

In certain embodiments, the methacrylic acid/ethyl acrylate copolymer is EUDRAGIT® L100-55.

In certain embodiments, the enteric coating begins to substantially dissolve and drug release commences in the duodenum.

In certain embodiments, the enteric coating begins to substantially dissolve and drug release commences at about 1 or more hours after ingestion.

In certain embodiments, the oral pharmaceutical composition does not have substantially dose-limiting side effects.

In certain embodiments, said side effects are gastrointestinal.

In certain embodiments, said gastrointestinal side effects are chosen from nausea, emesis, diarrhea, abdominal pain, oral mucositis, oral ulceration, pharyngitis, stomatitis, and gastrointestinal ulceration.

In certain embodiments, said gastrointestinal side effects are chosen from inhibition of gastrointestinal mucosal proliferation, inhibition of migration of developing epithelial lumen cells, and inhibition of differentiation of stem or progenitor cells into epithelial lumen cells.

In certain embodiments, the delayed-release oral pharmaceutical dosage form has a $T_{max}$ from about 1 hour to about 14 hours. In certain embodiments, the delayed-release oral pharmaceutical dosage form has a $T_{max}$ from about 1 hour to about 8 hours. In certain embodiments, the delayed-release oral pharmaceutical dosage form has a $T_{max}$ from about 1 hour to about 4 hours. In further embodiments, the $T_{max}$ is from 1 hour to 2 hours. In further embodiments, the $T_{max}$ is from 2 hours to 3 hours. In further embodiments, the $T_{max}$ is from 3 hours to 4 hours. In further embodiments, the $T_{max}$ is from 4 hours to 5 hours. In further embodiments, the $T_{max}$ is from 5 hours to 6 hours. In further embodiments, the $T_{max}$ is from 6 hours to 7 hours. In further embodiments, the $T_{max}$ is from 7 hours to 8 hours. In further embodiments, the $T_{max}$ is from 8 hours to 9 hours. In further embodiments, the $T_{max}$ is from 9 hours to 10 hours. In further embodiments, the $T_{max}$ is from 10 hours to 11 hours. In further embodiments, the $T_{max}$ is from 11 hours to 12 hours. In further embodiments, the $T_{max}$ is chosen from about 1, about 1.5 about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, and about 12 hours.

In certain embodiments is provided a delayed-release capsule comprising between about 25 to about 350 mg/kg MGBG, wherein said capsule comprises an enteric coating, and wherein the MGBG $T_{max}$ is between 1 and 14 hours. In further embodiments, the enterically-coated delayed-release capsule has a $T_{max}$ which is between 1 and 4 hours. In further embodiments, the enterically-coated delayed-release capsule has a $T_{max}$ which is between 1 and 2 hours. In further embodiments, the enterically-coated delayed-release capsule has a $T_{max}$ which is between 2 and 4 hours. In further embodiments, the enterically-coated delayed-release capsule has a $T_{max}$ which is between 4 and 8 hours. In further embodiments, the enterically-coated delayed-release capsule has a $T_{max}$ which is between 8 and 14 hours.

In certain embodiments is provided a delayed-release capsule comprising between about 25 to about 350 mg/kg MGBG, wherein said capsule comprises an enteric coating, and wherein the MGBG $T_{max}$ is at least 1 hour later than a reference standard which is not enterically coated, etc. In further embodiments, the enterically-coated delayed-release capsule has a $T_{max}$ which is at least 2 hours later than a reference standard which is not enterically coated. In further embodiments, the enterically-coated delayed-release capsule has a $T_{max}$ which is at least 3 hours later than a reference standard which is not enterically coated. In further embodiments, the enterically-coated delayed-release capsule has a $T_{max}$ which is at least 4 hours later than a reference standard which is not enterically coated. In further embodiments, the enterically-coated delayed-release capsule has a $T_{max}$ which is at least 6 hours later than a reference standard which is not enterically coated.

In certain embodiments is provided a delayed-release capsule comprising between about 25 to about 350 mg/kg MGBG, wherein said capsule comprises an enteric coating, and wherein the MGBG $C_{max}$ is less than about 500 ng/mL. In further embodiments, the enterically-coated delayed-release capsule has a $C_{max}$ which is less than about 465 ng/mL. In further embodiments, the enterically-coated delayed-release capsule has a $C_{max}$ which is less than about 400 ng/mL. In further embodiments, the enterically-coated delayed-release capsule has a $C_{max}$ which is less than about 300 ng/mL. In further embodiments, the enterically-coated delayed-release capsule has a $C_{max}$ which is less than about 200 ng/mL. In further embodiments, the enterically-coated delayed-release capsule has a $C_{max}$ which is less than about 100 ng/mL. In further embodiments, the enterically-coated delayed-release capsule has a $C_{max}$ which is less than about 50 ng/mL. In further embodiments, the enterically-coated delayed-release capsule has a $C_{max}$ which is less than about 25 ng/mL. In further embodiments, the enterically-coated delayed-release capsule has a $C_{max}$ which is less than about 12 ng/mL.

In certain embodiments is provided a delayed-release capsule comprising between about 25 to about 350 mg/kg MGBG, wherein said capsule comprises an enteric coating, and wherein the MGBG $C_{max}$ is between 10 and 465 ng/mL.

In certain embodiments is provided a delayed-release capsule comprising between about 25 to about 350 mg/kg MGBG, wherein said capsule comprises an enteric coating, and wherein the MGBG $C_{max}$ is 50% less than a reference standard which is not enterically coated. In further embodiments, the enterically-coated delayed-release capsule has a $C_{max}$ which is at least 60% less than a reference standard which is not enterically coated. In yet further embodiments is provided a delayed-release capsule comprising between about 25 to about 350 mg/kg MGBG, wherein said capsule comprises an enteric coating, and wherein the MGBG $C_{max}$ is 75% less than a reference standard which is not enterically coated.

In certain embodiments is provided a delayed-release capsule comprising between about 25 to about 350 mg/kg MGBG, wherein said capsule comprises an enteric coating, and wherein the MGBG AUC is less than about 3,100 ng*hr/mL. In certain embodiments is provided a delayed-release capsule comprising between about 25 to about 350 mg/kg MGBG, wherein said capsule comprises an enteric coating, and wherein the MGBG AUC is between about 180 and about 3,100 ng*hr/mL.

In certain embodiments is provided a delayed-release capsule comprising between about 25 to about 350 mg/kg MGBG, wherein said capsule comprises an enteric coating, and wherein the MGBG AUC is between about 20% and about 50% less than a reference standard which is not enterically coated. In further embodiments, the enterically-coated delayed-release capsule has an MGBG AUC between about 30% and about 50% less than a reference standard which is not enterically coated. In further embodiments, the enterically-coated delayed-release capsule has an MGBG AUC between about 30% and about 50% less than a reference standard which is not enterically coated. In certain embodiments is provided a delayed-release capsule comprising between about 25 to about 350 mg/kg MGBG, wherein said capsule comprises an enteric coating, and wherein the MGBG AUC is about 40% less than a reference standard which is not enterically coated.

Also provided is a delayed-release oral pharmaceutical dosage form comprising MGBG dihydrochloride hydrate in capsule enterically-coated for duodenal release. In certain embodiments, wherein the enteric coating comprises a methacrylic acid/ethyl acrylate copolymer. In certain embodiments, the methacrylic acid/ethyl acrylate copolymer is EUDRAGIT® L100-55. In certain embodiments, wherein the capsule comprises 25-350 mg MGBG. In certain embodiments, reduced gastrointestinal side effects in patients compared to a non-enterically-coated capsule.

In certain embodiments, the controlled-release dosage form is an extended release form.

In certain embodiments, the delayed-release oral pharmaceutical dosage form is a capsule comprising micropellets of MGBG optionally with one or more excipients, said micropellets being coated with an enteric coating, and optionally with a seal coating beneath the enteric coating.

In certain embodiments, the delayed-release oral pharmaceutical dosage form is a capsule comprising spheroids of MGBG optionally with one or more excipients, said spheroids being coated with an enteric coating, and optionally with a seal coating beneath the enteric coating.

In certain embodiments, the delayed-release oral pharmaceutical dosage form is a capsule comprising MGBG optionally with one or more excipients, said capsule being coated with an enteric coating, and optionally with a seal coating beneath the enteric coating.

In certain embodiments, the delayed-release oral pharmaceutical dosage form is a tablet having an enteric coating. In further embodiments, the delayed-release tablet comprises an enteric coating applied directly to the tablet. In other embodiments, delayed-release tablet comprises a seal coating applied directly to the tablet and an enteric coating.

In certain embodiments, the dosage form is chosen from extended-release and sustained-release.

In certain embodiments, the dosage form additionally comprises a hydrogel.

In certain embodiments, the dosage form comprises micropellets having at least one layer comprising said MGBG and at least one layer comprising at least one cellulose ether.

In certain embodiments, the cellulose ethers are chosen from methylcellulose, ethylcellulose, hydroxypropylmethylcellulose, carboxymethylcellulose, or microcrystalline cellulose.

In certain embodiments, the cellulose ether layer comprises ethylcellulose and hydroxypropylcellulose.

In certain embodiments, the dosage form comprises micropellets having coated onto a seed a first layer comprising said MGBG and a second layer comprising ethylcellulose and hydroxypropylcellulose.

In certain embodiments, the second layer makes up from about 2% to about 10% by weight of the micropellet.

In certain embodiments, the second layer comprises 70-90% by weight of ethylcellulose and about 10-30% by weight of hydroxypropylcellulose.

In certain embodiments, the cellulose ether layer comprises 80-90% by weight of ethylcellulose and about 10-20% by weight of hydroxypropylcellulose.

In certain embodiments, the cellulose ether layer comprises about 3 parts of ethylcellulose to about 1 part of hydroxypropylcellulose.

In certain embodiments, the layer comprising MGBG additionally comprises a polyvinylpyrrolidone.

In certain embodiments, said polyvinylpyrrolidone has a molecular weight of about 30,000 to about 50,000.

In certain embodiments, said polyvinylpyrrolidone has a molecular weight of about 40,000.

In other embodiments, the dosage form comprises spheroids comprised of MGBG and a cellulose ether.

In certain embodiments, the micropellets have diameters in the range of about 0.5 to about 0.7 mm.

Also provided herein is a controlled-release oral pharmaceutical dosage form comprising MGBG together with at least one oral pharmaceutically acceptable excipient, which yields a therapeutically effective systemic plasma MGBG level when orally administered to a subject, which does not have substantially dose-limiting side effects. In certain embodiments, said side effects are gastrointestinal. In further embodiments, said gastrointestinal side effects are chosen from nausea, emesis, diarrhea, abdominal pain, oral mucositis, oral ulceration, pharyngitis, stomatitis, and gastrointestinal ulceration. In further embodiments, said gastrointestinal side effects are chosen from inhibition of gastrointestinal mucosal proliferation, inhibition of migration of developing epithelial lumen cells, and inhibition of differentiation of stem or progenitor cells into epithelial lumen cells. In certain embodiments, said side effects are chosen from thrombocytopenia, leukopenia, phlebitis, laryngitis, cellulitis, dermatitis, and hypoglycemia.

Also provided herein is a low-dose oral pharmaceutical composition for chronic delivery, comprising a therapeutically effective amount of MGBG and at least one pharmaceutically acceptable excipient, which does not have substantial gastrointestinal side effects. In certain embodiments, the low-dose oral pharmaceutical composition for chronic delivery, comprising a therapeutically effective amount of MGBG and at least one pharmaceutically acceptable excipient, which does not have substantial gastrointestinal side effects, yields a therapeutically effective plasma level of MGBG for at least a 24 hour period in the subject with once-daily dosing.

In certain embodiments, the pharmaceutical composition is formulated as a tablet or capsule. For example, in certain embodiments, the pharmaceutical composition comprises:
- 0.1-50% of a polyamine analog or a polyamine biosynthesis inhibitor;
- 0.1-99.9% of a filler;
- 0-10% of a disintegrant;
- 0-5% of a lubricant; and
- 0-5% of a glidant.

In certain embodiments, the pharmaceutical composition comprises:
- 0.1-50% of MGBG;
- 0.1-99.9% of a filler;
- 0-10% of a disintegrant;
- 0-5% of a lubricant; and
- 0-5% of a glidant.

In further embodiments,
- said filler is chosen from a sugar, a starch, a cellulose, and a poloxamer;
- said disintegrant is chosen from povidone and crospovidone;
- said lubricant is magnesium stearate; and
- said glidant is silicon dioxide.

In further embodiments,
- said filler is chosen from lactose and microcrystalline cellulose;
- said disintegrant is chosen from povidone and crospovidone;
- said lubricant is magnesium stearate; and
- said glidant is silicon dioxide.

In certain embodiments, the pharmaceutical composition comprises:
- 10-300 mg of a polyamine analog or a polyamine biosynthesis inhibitor, making up 2-50% of the tablet content or capsule fill content;
- 0-10% of a disintegrant;
- 0-5% of a lubricant;
- 0-5% of a glidant; and
- 30-98% of a filler.

In certain embodiments, the pharmaceutical composition comprises:
- 10-300 mg of MGBG, making up 2-50% of the tablet content or capsule fill content;
- 0-10% of a disintegrant;
- 0-5% of a lubricant;
- 0-5% of a glidant; and
- 30-98% of a filler.

In further embodiments, the pharmaceutical composition comprises
- 0.1-10% of a binder;
- 0-5% of a surfactant;
- 0-10% of an intergranular disintegrant; and
- 0-10% of an extragranular disintegrant.

In further embodiments, the pharmaceutical composition may additionally comprise
- 0-10% of a binder;
- 0-5% of a surfactant;
- 0-10% of an intergranular disintegrant; and
- 0-10% of an extragranular disintegrant.

In further embodiments,
- said binder is chosen from copolyvidone, hydroxypropylcellulose, hydroxypropylmethylcellulose, and povidone;
- said surfactant is chosen from polyoxyethylene (20) sorbitan monooleate, a poloxamer, and sodium lauryl sulfate;
- said intergranular disintegrant is chosen from croscarmellose sodium, sodium starch glyconate, and crospovidone; and
- said extragranular disintegrant is chosen from croscarmellose sodium, sodium starch glyconate, and crospovidone.

Also provided herein is a method of treating, or delaying the onset or development of, a condition in a subject in need thereof comprising the administration of a controlled-release oral pharmaceutical dosage form comprising MGBG. In certain embodiments, the MGBG is delivered in a therapeutically effective amount.

Also provided herein is a method of treatment of a condition in a subject in need thereof comprising the administration of
  an oral pharmaceutical composition comprising MGBG and at least one pharmaceutically acceptable excipient; and
  another therapeutic agent.

In certain embodiments, the MGBG is delivered in a therapeutically effective amount. In other embodiments, the MGBG is delivered in a subtherapeutic amount. In certain embodiments, the other therapeutic agent is delivered in a therapeutically effective amount. In other embodiments, the other therapeutic agent is delivered in a subtherapeutic amount. In certain embodiments, the MGBG and the other therapeutic agent are delivered together in amounts which would individually be subtherapeutic but which together are therapeutically effective. In other embodiments, the MGBG and the other therapeutic agent are delivered together in amounts which are individually therapeutically effective.

Also provided herein is a method of treating a condition comprising the administration, to a patient in need thereof, a delayed-release oral pharmaceutical dosage form comprising MGBG.

In certain embodiments, the condition is pain. In certain embodiments, the pain is inflammatory pain.

In certain embodiments, said delayed release oral pharmaceutical dosage form is an enterically-coated capsule comprising MGBG.

In certain embodiments, the administration of the enterically-coated capsule comprising MGBG results in a reduction of gastrointestinal side effects when compared to a reference standard that is not enterically coated.

In certain embodiments, said gastrointestinal side effects are chosen from nausea, emesis, diarrhea, abdominal pain, oral mucositis, oral ulceration, pharyngitis, stomatitis, irritation of the gastric mucosa, and gastrointestinal ulceration.

In certain embodiments, said gastrointestinal side effect is emesis.

In certain embodiments, MGBG is administered at a dosage level which would result in dose-limiting side effects if administered as a non-enteric coated dosage form.

Controlled-release oral pharmaceutical dosage forms disclosed herein are useful for targeting absorption of MGBG to a particular portion of the gastrointestinal tract, or for modulating the temporal delivery of MGBG, or both. These objectives may be achieved, for example, by formulating MGBG in an oral dosage form having a modified-release film coating, by formulating MGBG in a swelling system, by formulating MGBG in a matrix, by formulating MGBG in a controlled dissolutions system using coated particles, granules, micropellets, or spheroids of a pharmaceutical composition of MGBG or by microencapsulation, or by formulating MGBG in an osmotically active delivery system.

For targeting absorption of MGBG to a particular portion of the gastrointestinal tract, film coatings and swelling systems are particularly useful. Swelling systems represent a means to target absorption of drug in the stomach. Such a dosage form would comprise MGBG in a matrix of material which would expand upon contact with the aqueous environment of the stomach, preventing passage into the duodenum. Hydrogels are one example of such a material. Typically a hydrogel comprises, for example, polyvinyl alcohol, sodium polyacrylate, acrylate polymers and/or copolymers with an abundance of hydrophilic groups.

When targeting the small intestine is desired, a film coating is useful. One type of film coating is an enteric coating, which is designed to remain intact in the stomach, but dissolves and releases drug in the small intestine. Release in the small intestine may be desirable if, for example, the drug is inactivated or rendered less useful by reaction with gastric fluids, or if the drug causes gastric irritation or related side effects such as nausea and/or emesis.

Most enteric coatings achieve delayed release by virtue of being resistant to dissolution at low pH such as that found in the stomach, but which dissociate more readily in the higher pH environment of the small intestine. Most effective enteric coatings are therefore weak acids with pKas of about 3 to about 5. Additionally, coatings which are responsive to intestinal enzymatic breakdown may be used.

Enteric coatings which are pH-labile are typically formed of polymers, optionally in combination with plasticizing agents and other excipients. Shellac and gelatin may be used, but polymerization must be carefully controlled or the contents of the dosage form will not be released. Suitable polymers include cellulose acetate phthalate (CAP), polyvinyl acetate phthalate (PVAP), hydroxypropyl methylcellulose (HPMC), hydroxypropyl methylcellulose phthalate (HP-MCP), acrylic copolymers such as methacrylic acid/methacrylic acid ester copolymers, ethyl acrylate/methyl methacrylate/methacrylic acid copolymer, and methacrylic acid/ethyl acrylate copolymer, cellulose acetate trimellate (CAT), carboxymethyl ethylcellulose (CMEC), hydroxypropyl methylcellulose acetate succinate (HPMCAS), and acrylic copolymers. Prepared copolymers are commercially available in many forms, such as aqueous suspensions, organic solutions, and powders, for release of drug to various parts of the small intestine, such as the duodenum, jejunum, or ileum. For example, the EUDRAGIT® series of coatings is available from Evonik Inds., and the SURELEASE® series from Colorcon.

Alternatively or in addition to an enteric coating, a sustained-release coating may be employed. Such a coating would be useful where rapid release of drug causes undesirable side effects. Suitable materials for creating a sustained-release coating include, in addition to the polymers above: mixtures of waxes with glyceryl monostearate, stearic acid, palmitic acid, glyceryl monopalmitate, and/or cetyl alcohol; ethylcellulose; acrylic resins; cellulose acetates; and silicone elastomers.

Methods for coating dosage forms with enteric, sustained-release, or enteric/sustained-release coatings include spray-drying (pan coating), air suspension column coating, and electrostatic powder coating followed by heat fixation. The pan coating method is useful for depositing a substantial coating onto the tablet; in certain embodiments, 3%-4% of the tablet weight is deposited as coating, but it can be significantly higher, up to about 15%. Where a thinner coating is desired, the air suspension coating technique is useful. The initial seal coat can be applied on an Aeromatic Strea™ fluid bed apparatus fitted with a Wurster column and bottom spray nozzle system. The electrostatic method may be useful where it is desirable to avoid use of solvents, where dosage forms are to be partially coated, or where precision in deposition or even greater thinness of the coating is desired.

In certain embodiments, the MGBG oral dosing units of the invention comprise at minimum a core containing MGBG, and one or more pharmaceutically acceptable excipients. In certain embodiments, the core may contain about 10 wt % to about 90 wt % MGBG. The core containing the MGBG may be in a sustained release formulation or other suitable cores as are described in greater detail below may be selected. In certain embodiments, a delay release coat and/or an enteric coat are provided over the core.

The delay release coat and/or an enteric coat (rate-controlling film) can be applied to the MGBG core directly, or there may be intermediate coating layers located between the MGBG core and any over coats. Optionally, a further seal or top coat may be located outside the enteric coat.

In certain embodiments, the MGBG core is provided with further layers that provide a sustained release formulation which contains rate-controlling components. Typically, such rate controlling components are rate controlling polymers selected from among hydrophilic polymers and inert plasticized polymers. Suitable rate controlling hydrophilic polymers include, without limitation, polyvinyl alcohol (PVA), hypomellose and mixtures thereof. Examples of suitable insoluble or inert "plastic" polymers include, without limitation, one or more polymethacrylates (i.e., EUDRAGIT® polymer). Other suitable rate-controlling polymer materials include, e.g., hydroxyalkyl celluloses, poly(ethylene) oxides, alkyl celluloses, carboxymethyl celluloses, hydrophilic cellulose derivatives, and polyethylene glycol.

Thus, in certain embodiments, the formulation of the invention contains one or more coatings over the MGBG core. In still other embodiments, the core can contain a non-functional seal coating (i.e., a coat which does not affect release rate) and a functional second coating. The enteric coat can be applied directly to the uncoated core, or may be applied over an initial seal coat.

In certain embodiments, an initial seal coat can be applied directly to the core. Although the components of this seal coat can be modified by one of skill in the art, the seal coat may be selected from among suitable polymers such as hydroxypropyl methylcellulose (HPMC), ethylcellulose, polyvinyl alcohol, and combinations thereof, optionally containing plasticizers and other desirable components. A particularly suitable seal coat contains HPMC. For example, a seal coat can be applied as a HPMC solution at a concentration of about 3% w/w to 25% w/w. In certain embodiments, the seal coat can be applied as a HPMC solution at a concentration of about 5% w/w to about 7.5% w/w. In certain embodiments, the initial seal coat is in the range of about 1% w/w to about 3% w/w, or about 2% w/w, of the uncoated core. In another embodiment, a commercially available seal coat containing HPMC, among other inert components, is utilized. One such commercially available seal coat is OPADRY® Clear (Colorcon, Inc.).

In certain embodiments, the enteric coat contains a product which is a copolymer of methacrylic acid and methacrylates, such as the commercially available EUDRAGIT® L 30 K55 (Röhm GmbH & Co. KG). This enteric coat may be applied such that it coats the core in an amount of about 10 wt % to 20 wt %, or about 12 wt % to about 17 wt %, or about 15.5 wt % to 16.5 wt % of the uncoated or initially-coated core. In certain embodiments, the enteric coat is composed of a EUDRAGIT® L30D-55 copolymer (Röhm GmbH & Co. KG), talc, triethyl citrate, and water. In certain embodiments, the enteric coating may contain about 7 wt % to about 9 wt % of a 30 wt % dispersion of EUDRAGIT® L 30 D55 coating; about 4 wt % to about 5 wt %/w talc, about 0.7 wt % to about 1 wt % triethyl citrate; a pH adjuster such as sodium hydroxide and water.

In certain embodiments, the delayed-release oral pharmaceutical dosage form is a capsule comprising micropellets of MGBG optionally with one or more excipients, said micropellets being coated with an enteric coating, and optionally with a seal coating beneath the enteric coating.

In certain embodiments, the delayed-release oral pharmaceutical dosage form is a capsule comprising spheroids of MGBG and one or more excipients, said spheroids being coated with an enteric coating, and optionally with a seal coating beneath the enteric coating.

In certain embodiments, the delayed-release oral pharmaceutical dosage form is a tablet having an enteric coating. In further embodiments, the delayed-release tablet comprises an enteric coating applied directly to the tablet. In other embodiments, delayed-release tablet comprises a seal coating applied directly to the tablet and an enteric coating.

In certain embodiments, the enteric coating comprises from about 1% to about 30% of the total weight of the delayed-release oral pharmaceutical dosage form. In further embodiments, the enteric coating comprises from 1% to 25%, or from 1% to 20%, or from 1% to 15% of the total weight of the delayed-release oral pharmaceutical dosage form. In further embodiments, the enteric coating comprises from 1% to 10%, or from 1% to 5% of the total weight of the delayed-release oral pharmaceutical dosage form. In further embodiments, the enteric coating comprises a percentage of the total weight of the delayed-release oral pharmaceutical dosage form chosen from about 1%, about 2%, about 3%, about 4%, and about 5%. In further embodiments, the enteric coating comprises from 5% to 10% of the total weight of the delayed-release oral pharmaceutical dosage form. In further embodiments, the enteric coating comprises a percentage of the total weight of the delayed-release oral pharmaceutical dosage form chosen from about 6%, about 7%, about 8%, about 9%, and about 10%. In further embodiments, the enteric coating comprises from 10% to 15% of the total weight of the delayed-release oral pharmaceutical dosage form. In further embodiments, the enteric coating comprises a percentage of the total weight of the delayed-release oral pharmaceutical dosage form chosen from about 11%, about 12%, about 13%, about 14%, and about 15%. In further embodiments, the enteric coating comprises from 15% to 20% of the total weight of the delayed-release oral pharmaceutical dosage form. In further embodiments, the enteric coating comprises a percentage of the total weight of the delayed-release oral pharmaceutical dosage form chosen from about 16%, about 17%, about 18%, about 19%, and about 20%. In further embodiments, the enteric coating comprises from 20% to 30% of the total weight of the delayed-release oral pharmaceutical dosage form. In these embodiments, the enteric coating is substantially uniform in thickness.

In certain embodiments, the controlled-release oral pharmaceutical dosage form may be achieved through formulation in a matrix. The matrix may be a controlled release matrix, although normal release matrices having a coating that controls the release of the drug may be used. Suitable materials for inclusion in a controlled release matrix are a) Hydrophilic polymers, such as gums, cellulose ethers, acrylic resins and protein derived materials. In certain embodiments, the polymers are cellulose ethers. In further embodiments, the cellulose ethers are hydroxyalkylcelluloses (e.g., methylcellulose, hydroxypropyl methylcellulose), and carboxyalkylcelluloses (e.g., carboxymethylcellulose, carbopol 934). The oral dosage form may contain between 1% and 80% (by weight) of at least one hydrophilic or hydrophobic polymer.

b) Insoluble plastics, including methyl-acrylate methylmethacrylate, polyvinyl chloride, and polyethylene.

c) Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes. In certain embodiments the hydrocarbons have a melting point of between 25° and 90° C. In further embodiments, the long chain hydrocarbon materials are fatty (aliphatic) alcohols. The oral dosage form may contain up to 60% (by weight) of at least one digestible, long chain hydrocarbon.

d) Polyalkylene glycols. The oral dosage form may contain up to 60% (by weight) of at least one polyalkylene glycol.

A common method of preparation is to mix drug and matrix material and then to compress into a tablet. When a priming dose is desirable, the tablet may then be coated with a drug-containing layer substantially free of matrix material. An additional enteric coating may be added if delay of release is desired.

In certain embodiments, the matrix comprises at least one water soluble hydroxyalkyl cellulose, at least one $C_{12}$-$C_{36}$ aliphatic alcohol and, optionally, at least one polyalkylene glycol. In further embodiments, the aliphatic alcohol is a $C_{14}$-$C_{22}$ aliphatic alcohol.

The hydroxyalkyl cellulose may be, for example, a hydroxy ($C_1$ to $C_6$) alkyl cellulose, such as hydroxypropylcellulose, hydroxypropylmethylcellulose or hydroxyethyl cellulose. The amount of the hydroxyalkyl cellulose in the present oral dosage form will be determined, inter alia, by the precise rate of drug release required. In certain embodiments, the oral dosage form contains between 5% and 25% (by wt) of the hydroxyalkyl cellulose. In further embodiments, the oral dosage form contains between 6.25% and 15% of the hydroxyalkyl cellulose.

The aliphatic alcohol may be, for example, lauryl alcohol, myristyl alcohol or stearyl alcohol. In certain embodiments, the aliphatic alcohol is cetyl alcohol or cetostearyl alcohol. The amount of the aliphatic alcohol in the present oral dosage form will be determined, as above, by the precise rate of drug release required. It will also depend on whether polyalkylene glycol is present in or absent from the oral dosage form. In certain embodiments, in the absence of polyalkylene glycol, the oral dosage form may contain between 20% and 50% (by wt) of the aliphatic alcohol. In other embodiments, where polyalkylene glycol is present in the oral dosage form, then the combined weight of the aliphatic alcohol and the polyalkylene glycol may constitute between 20% and 50% (by wt) of the total dosage.

In certain embodiments, the controlled release composition comprises from about 5 to about 25% acrylic resin and from about 8 to about 40% by weight aliphatic alcohol by weight of the total dosage form. Many acrylic resins are commercially available. Examples include the entire family of EUDRAGIT® family of formulation copolymers—EUDRAGIT® RS PM is one example, EUDRAGIT® RL 30 D is another.

In general, the ratio of, e.g., hydroxyalkyl cellulose or acrylic resin to aliphatic alcohol/polyalkylene glycol determines, to a considerable extent, the release rate of the drug from the formulation. In certain embodiments, the ratio of hydroxyalkyl cellulose to aliphatic alcohol/polyalkylene glycol is between 1:2 and 1:4. In further embodiments, the ratio is between 1:3 and 1:4.

The polyalkylene glycol may be, for example, polypropylene glycol. In certain embodiments, the polyalkylene glycol is polyethylene glycol. In certain embodiments, the average molecular weight of the polyalkylene glycol is between 1,000 and 15,000. In certain embodiments, the average molecular weight of the polyalkylene glycol is between 1500 and 12000.

Another suitable controlled release matrix would comprise an alkylcellulose (especially ethyl cellulose), a C12 to C36 aliphatic alcohol and, optionally, a polyalkylene glycol.

In addition to the above ingredients, a controlled release matrix may also contain suitable quantities of other materials, e.g. diluents, lubricants, binders, granulating aids, colorants, flavorants and glidants that are conventional in the pharmaceutical art.

As an alternative to a controlled release matrix, the present matrix may be a normal release matrix having a coat that controls the release of the drug. In certain embodiments, the dosage form comprises film coated spheroids containing active ingredient and a non-water soluble spheronising agent. The term spheroid is known in the pharmaceutical art and usually refers to a spherical granule having a diameter of between 0.1 mm and 2.5 mm especially between 0.5 mm and 2 mm.

The spheronising agent may be any pharmaceutically acceptable material that, together with the active ingredient, can be spheronised to form spheroids. Microcrystalline cellulose is an example of a spheronizing agent. A suitable microcrystalline cellulose is, for example, the material sold as Avicel PH 101 (Trade Mark, FMC Corporation). In certain embodiments, the film coated spheroids contain between 10% and 95% (by wt) of the spheronising agent. In further embodiments, the film coated spheroids contain between 20% and 80% (by wt) of the spheronising agent. In further embodiments, the film coated spheroids contain between 20% and 50% (by wt) of the spheronising agent. In further embodiments, the film coated spheroids contain between 10% and 40% (by wt) of the spheronising agent. In further embodiments, the film coated spheroids contain between 20% and 40% (by wt) of the spheronising agent. In further embodiments, the spheronizing agent is microcrystalline cellulose.

In addition to the active ingredient and spheronising agent, the spheroids may also contain a binder. Suitable binders, such as low viscosity, water soluble polymers, will be well known to those skilled in the pharmaceutical art. Microcrystalline cellulose is an effective diluent and binder. In certain embodiments, the binder is a water soluble hydroxy lower alkyl cellulose, such as hydroxypropyl cellulose. Additionally (or alternatively) the spheroids may contain a water insoluble polymer, such as an acrylic polymer, an acrylic copolymer, such as a methacrylic acid-ethyl acrylate copolymer, or ethyl cellulose.

In certain embodiments, the spheroids are film coated with a material that permits release of the drug at a controlled rate in an aqueous medium.

The film coat will generally include a water insoluble material such as a wax, either alone or in admixture with a fatty alcohol,
shellac or zein,
a water insoluble cellulose, or
a polymethacrylate.

In certain embodiments, the water insoluble cellulose is ethyl cellulose.

In certain embodiments, the polymethacrylate is EUDRAGIT®.

In further embodiments, the film coat comprises a mixture of the water insoluble material and a water soluble material. The ratio of water insoluble to water soluble material is determined by, amongst other factors, the release rate required and the solubility characteristics of the materials selected.

The water soluble material may be, for example, polyvinylpyrrolidone or a water soluble cellulose. In certain embodiments, the water soluble cellulose is hydroxypropylmethyl cellulose.

Suitable combinations of water insoluble and water soluble materials for the film coat include shellac and polyvinylpyrrolidone, or ethyl cellulose and hydroxypropylmethyl cellulose. In certain embodiments, the combination of water insoluble and water soluble materials for the film coat is ethyl cellulose and hydroxypropylmethyl cellulose.

Additionally, a process for the preparation of a solid, controlled release, oral dosage form according to the present invention comprising incorporating MGBG in a controlled release matrix is provided. Incorporation in the matrix may be effected, for example, by forming granules comprising at least one water soluble hydroxyalkyl cellulose and MGBG, mixing the hydroxyalkyl cellulose containing granules with at least one C12-C36 aliphatic alcohol, and optionally, compressing and shaping the granules. In certain embodiments, the granules are formed by wet granulating the hydroxyalkyl cellulose/MGBG with water. In further embodiments of this process, the amount of water added during the wet granulation step is between 1.5 and 5 times the dry weight of the MGBG. In further embodiments, the amount is between 1.75 and 3.5 times the dry weight of the MGBG.

The present solid, controlled release, oral dosage form may also be prepared, in the form of film coated spheroids, by blending a mixture comprising MGBG and a non-water soluble spheronising agent, extruding the blended mixture to give an extrudate, spheronising the extrudate until spheroids are formed, and coating the spheroids with a film coat.

In certain embodiments, the controlled-release oral pharmaceutical dosage form may be achieved through formulation in micropellets which may then be either compressed into a tablet or put into a capsule.

In certain embodiments, the MGBG may be coated onto a seed, such as a sugar seed crystal of a predetermined size, by first combining it with polyvinylpyrrolidone, having a molecular weight of from about 30,000 to about 50,000 with a molecular weight of about 40,000 being preferred. The sugar seeds which may be coated with a combination of MGBG and polyvinylpyrrolidone are then in turn coated with an outer coating comprised of two polymers. The sugar seeds coated with MGBG may then be coated with from 5% to 10% by weight of sustained release coating which is comprised of a combination of ethylcellulose and hydroxypropylcellulose. In certain embodiments the sustained release coating is comprised of 70% to 90% by weight of ethylcellulose and 10% to 30% hydroxypropylcellulose based on the weight of the coating. In certain embodiments, the outer coating is comprised of 75% ethylcellulose and 25% hydroxypropylcellulose. In further embodiments, the average diameter of each of the micropellets formed is 0.5 to 0.7 mm, particularly preferably about 0.6 mm.

These micropellets may be comprised, for example, of 5% to 10% by weight of a coating of two different polymers. In certain embodiments, one of the polymers is ethylcellulose with is present in the coating in an amount of 90% to 70% by weight, based on the weight of the coating; the other polymer is hydroxypropylcellulose which is present in an amount of 10% to 30% by weight, based on the weight of the coating. When a coating is comprised in this manner and placed on a micropellet as described in detail below, the oral formulation of the invention will provide zero order release of MGBG.

The inclusion of hydroxypropylcellulose within the coating along with the ethylcellulose provides the desired sustained release of the active ingredient MGBG. If the micropellets of the present invention were coated with a coating comprised completely of ethylcellulose (which is an ethyl ether of cellulose) containing 2.25-2.28 ethoxyl groups per anhydroglucose unit, the drug within the coating would be released very slowly or be released not at all for a long period of time. Hydroxypropylcellulose, wherein the primary hydroxyls present in cellulose have been substituted (etherified) by hydroxypropyl is more water soluble then ethylcellulose. Accordingly, the presence of such hydroxypropylcellulose in the coating provides "channels" in the coating through which water can enter, and over a period of time, leach out the MGBG contained within the non-pareil sugar seed. The presence of too many "channels" will make the MGBG more quickly available then is therapeutically appropriate. Within the stated range, an optimal release rate is obtained when the outer coating contains three parts of ethylcellulose (75% by weight) to one part of hydroxypropyl cellulose (25% by weight)

Compounds for use in the dosage forms disclosed herein include MGBG, as well as other polyamine analogs and polyamine biosynthesis inhibitors, and their salts, prodrugs, solvates, anhydrous forms, protected derivatives, structural isomers, stereoisomers, amino acid conjugates, and porphyrin conjugates thereof. Any polyamine analog is suitable for use in the dosage forms of the present invention.

MGBG is 1,1' [methylethanediylidene]dinitrilodiguanidine and is also known as methylglyoxal bis(guanylhydrazone), methyl-GAG, Me-G, and mitoguazone. As used herein, MGBG includes the free base and salts thereof. It is commonly, but not necessarily, used as a dihydrochloride. MGBG may be present as any one of the following isomers, or a tautomer and/or a syn/anti isomer thereof, mixture of one or more thereof:

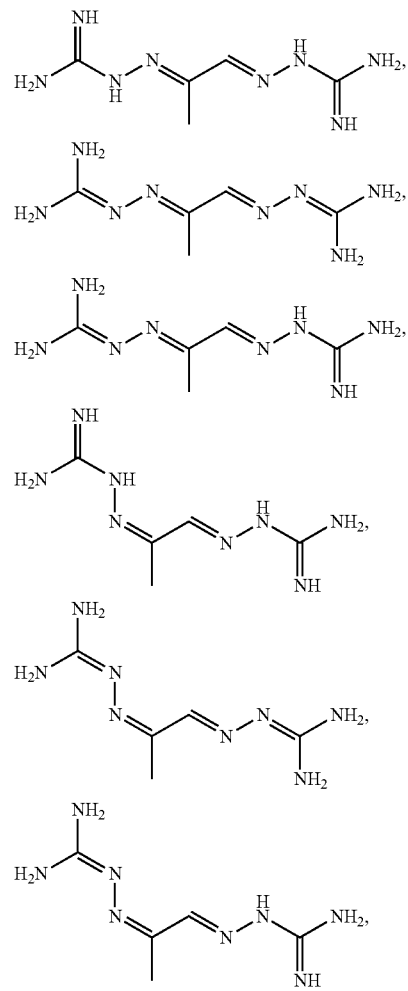

-continued

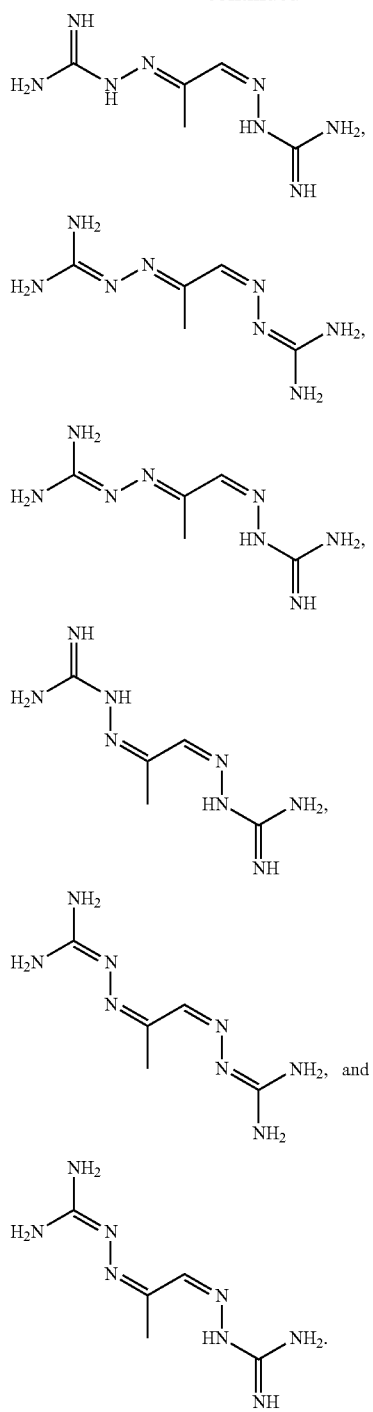

In certain embodiments, MGBG may be present in one of the following isomers, or a tautomer and/or a syn/anti isomer thereof, mixture of one or more thereof:

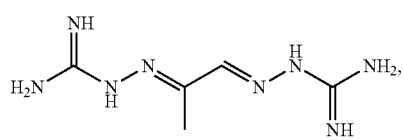

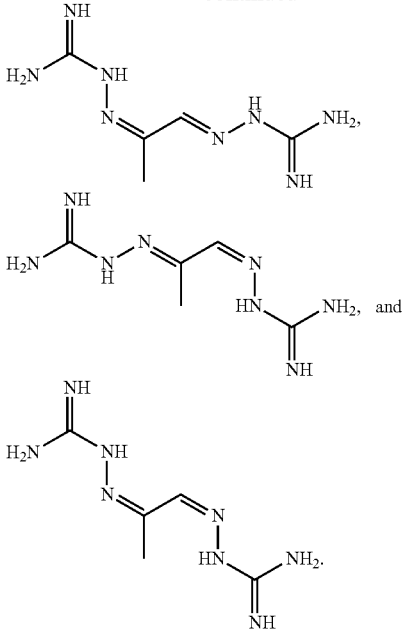

Other polyamine analogs used in the methods of the invention include compounds of the structural formulas 1, 2, 3, 4, 5, 6, and 7 and the corresponding stereoisomers, salts, and protected derivatives thereof.

Formula 1 has the structure

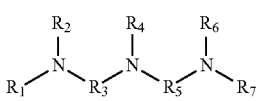

wherein
$R_1$, $R_2$, $R_4$, $R_6$ and $R_7$ are independently chosen from hydrogen, alkyl and aryl; and
$R_3$ and $R_5$, are alkyl groups.

Formula 2 has the structure

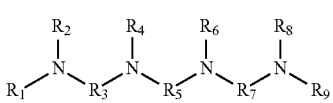

wherein
$R_1$, $R_2$, $R_4$, $R_6$, $R_8$, and $R_9$ are independently chosen from hydrogen, alkyl and aryl; and
$R_3$, $R_5$ and $R_7$ are alkyl groups.

Formula 3 has the structure

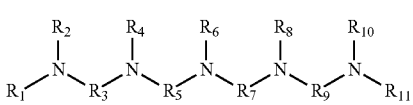

wherein
$R_1$, $R_2$, $R_4$, $R_6$, $R_{10}$ and $R_{11}$ are independently chosen from hydrogen, alkyl and aryl; and
$R_3$, $R_5$, $R_7$ and $R_9$ are alkyl groups.

Formula 4 has the structure

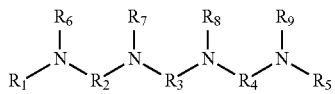

wherein $R_1$ and $R_5$ are independently chosen from methyl, ethyl, n-propyl, and isopropyl;

$R_2$, $R_3$, and $R_4$ are independently chosen from $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl; and $R_6$, $R_7$, $R_8$ and $R_9$ are independently chosen from hydrogen, methyl, and ethyl;

Formula 5 has the structure

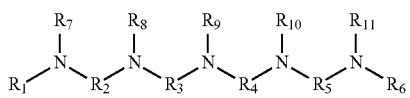

wherein $R_1$ and $R_6$ are independently chosen from methyl, ethyl, n-propyl, and isopropyl;

$R_2$, $R_3$, $R_4$ and $R_5$ are independently chosen from $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_3$-$C_{10}$ aryl-$C_1$-$C_6$ alkyl; and $R_7$, $R_8$, $R_9$, $R_{10}$ and $R_{11}$ are independently chosen from hydrogen, methyl, and ethyl.

In another embodiment, the polyamine analogs are compounds of structural formulas 2 and 3, wherein $R_3$, $R_5$, $R_7$ and $R_9$ are independently $(CH_2)_x$ groups;

x is an integer from 2 to 6; and $R_4$, $R_6$ and $R_8$ are hydrogen atoms.

In yet another embodiment, the polyamine analogs are compounds of structural formulas 2 and 3, wherein $R_3$, $R_5$, $R_7$ and $R_9$ are independently $(CH_2)_x$ groups;

x is an integer from 2 to 6;

$R_4$, $R_6$ and $R_8$ are hydrogen atoms;

$R_1$ and $R_{10}$ are alkyl groups; and $R_2$ and $R_{11}$ are hydrogen atoms.

In yet another embodiment, the polyamine analogs are compounds of structural formulas 2 and 3, wherein $R_3$, $R_5$, $R_7$ and $R_9$ are independently $(CH_2)_x$ groups;

x is an integer from 2 to 6;

$R_4$, $R_6$ and $R_8$ are hydrogen atoms;

$R_1$ and $R_{10}$ are alkyl groups;

$R_2$ and $R_{11}$ are hydrogen atoms; and the polyamine analogs have a molecular weight less than 500.

Further embodiments of compounds of structural formula 4 include those wherein $R_6$, $R_7$, $R_8$ and $R_9$ are hydrogen.

In other embodiments, $R_1$ and $R_5$ are ethyl.

In yet further embodiments, $R_6$, $R_7$, $R_8$ and $R_9$ are hydrogen; and $R_1$ and $R_5$ are ethyl.

In yet further embodiments, $R_2$ and $R_4$ are independently chosen from $C_1$-$C_6$ alkyl; and $R_3$ is chosen from $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl.

Additional polyamine analogs useful in the present invention include compounds of the formula 6, and the corresponding stereoisomers, salts, and protected derivatives thereof:

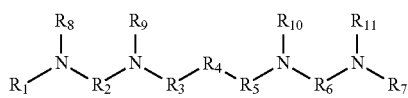

wherein $R_4$ is chosen from $C_2$-$C_6$ n-alkenyl, $C_3$-$C_6$ cycloalkyl, $C_3$-$C_6$ cycloalkenyl, and $C_3$-$C_6$ aryl;

$R_3$ and $R_5$ are independently chosen from a single bond, $C_1$-$C_6$ alkyl, and $C_1$-$C_6$ alkenyl;

$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, and $C_3$-$C_6$ aryl;

$R_1$ and $R_7$ are independently chosen from hydrogen, $C_1$-$C_6$ alkyl, and $C_2$-$C_6$ alkenyl; and $R_8$, $R_9$, $R_{10}$, and $R_{11}$ are hydrogen.

In certain embodiments of the compounds of formula 6, $R_1$ and $R_7$ are independently chosen from $C_1$-$C_6$ alkyl and $C_2$-$C_6$ alkenyl.

Additional polyamine analogs useful in the present invention include compounds of structural formula 7, and the corresponding stereoisomers, salts, and protected derivatives thereof:

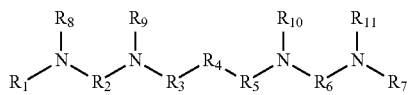

wherein $R_4$ is chosen from $C_1$-$C_6$ n-alkyl and $C_1$-$C_6$ branched alkyl;

$R_3$ and $R_5$ are independently chosen from a single bond or $C_1$-$C_6$ alkyl;

$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, or $C_3$-$C_6$ aryl;

$R_1$ and $R_7$ are independently chosen from H, $C_1$-$C_6$ alkyl, or $C_2$-$C_6$ alkenyl; and $R_8$, $R_9$, $R_{10}$, and $R_{11}$ are hydrogen.

In certain embodiments of the compounds of formula 7

$R_2$ and $R_7$ are independently chosen from $C_1$-$C_6$ alkyl or $C_2$-$C_6$ alkenyl;

$R_4$ is chosen from $C_1$-$C_6$ saturated n-alkyl and $C_1$-$C_6$ saturated branched alkyl; and $R_3$ and $R_5$ are independently chosen from a single bond and $C_1$-$C_6$ saturated n-alkyl.

According to another embodiment of the present invention, the agent is a chemical moiety that inhibits polyamine biosynthesis by inhibiting the activity of S-adenosyl methionine decarboxylase, inhibits polyamine biosynthesis by inhibiting an enzyme distinct from S-adenosyl methionine decarboxylase, or antagonizes the end-products (ie polyamines, including putrescine, spermidine, and spermine) of polyamine biosynthesis.

Examples of such moieties include, but are not limited to, those listed in Table 1. Irrespective of the form of the moiety listed in Table 1, it is understood that it includes, as applicable, a salt, protected derivative, and stereoisomer thereof.

TABLE 1

| Compound | Official Name (Not IUPAC) | Pub Chem ID |
|---|---|---|
| Decarboxylated SAM | s-adenosyl-3-methylthiopropylamine | 5351154 |
| Mitoguazone or "MGBG" | Methylglyoxal bis(guanylhydrazone) | 9561662 |
| EGBG | Ethylglyoxal bis(guanylhydrazone) | 2354 |
| Berenil | Diminazene or Diminazene aceturate | 4735 |
| Pentamidine | 4-[5-(4-carbamimidoylphenoxy)pentoxy] benzenecarboximidamide | |
| | 5'-(Dimethylsulphino)-5'-deoxyadenosine | |
| | S-adneosyl-4-methylthiobutyrate | |
| | S-adenosyl-S-methyl-L-cysteine | |
| AMA | S-(5'-Deoxy-5'-adenosyl) methylthioethylhydroxylamine | |
| EMGBG | Ethylmethylglyoxal bis(guanylhydrazone) | |
| DEGBG | Diethylglyoxal bis(guanylhydrazone) | 9574151 |
| CGP-33'829 | 6-((2-carbamimidoylhydrazono)methyl) picolinimidamide | 5479208 |
| CGP-36'958 | | |
| CGP-39'937 | 2,2'-bipyridine-6,6'-bis(carboximidamide) | |
| CGP-48664 or CGP48664A or SAM 364A | 4-amidinoindan-1-one 2'-amidinohydrazone | 5486811 |
| AbeAdo or MDL-73811 | 5'-[[(Z)-4-amino-2-butenyl]methylamino]- 5'-deoxyadenosine | 6436013 |
| MAOEA | 5'-deoxy-5'-[N-methyl-N-[2-(aminooxy)ethyl]amino]adenosine | 3081018 |
| MHZPA | 5'-deoxy-5'-[N-methyl-N-(3-hydrazinopropyl)amino]adenosine | 122092 |
| MHZEA | 5'-deoxy-5'-[(2-hydrazinoethyl)- methylamino]adenosine | |
| AdoMac | S-(5'-deoxy-5'-adenosyl)-1-ammonio-4-(methylsulfonio)-2cyclopentene | 3083364 |
| AdoMao | S-(5'-deoxy-5'-adenosyl)-1-aminoxy-4-(methylsulfonio)-2-cyclopentene | |
| APA | 1-Aminooxy-3-aminopropane | 65020 |
| AOE-PU | N-[2-aminooxyethyl]-1,4-diaminobutane | |
| AP-APA | 1-aminooxy-3-N-[3-aminopropyl]- aminopropane 1,11-bis(ethyl)norspermine | |
| BES | 1,8-bis(ethyl)spermidine | |
| BES | 1,12-bis(ethyl)spermine | |
| DESPM | N1,N12-diethylspermine | |
| BE-3-3-3 | 1,11-bis(ethylamino)-4,8-diazaundecan | |
| BE-4-4-4 | 1,14-bis(ethylamino)-5,10-diazatetradecane | |
| DEHOP or DEHSPM | Diethylhomospermine, N1,N14-diethylhomospermine | |
| DENOP | diethyl-norspermine | |
| BE-4-4-4-4 | 1,19-bis(ethylamino)-5,10,15-triaza-nonadecane | |
| SL11037 | N-ethyl-N'-(2-(3'-ethylamino-propylamino methyl)-cis-cyclopropylmethyl)-propane 1,3-diamine tetrahydrochloride | |
| SL11038 | N-ethyl-N'-(2-(3'-ethylamino-propylamino methyl)-trans-cyclobutylmethyl)-propane 1,3-diamine tetrahydrochloride | |
| SL11044 | N-ethyl-N'-(2-(3'-ethylamino-propylamino methyl)-transcyclopropylmethyl)-propane 1,3-diamine tetrahydrochloride | |
| SL11047 or SL47 | N,N'-bis(3-ethylaminopropyl)-cis-but-2-ene-1,4-diaminetetrahydrochloride | |
| SL11093 or SL93 | N,N'-(cyclopropane-1,2-diylbis(methylene))bis(N4-ethylbutane-1,4-diamine) | |

In yet another embodiment, the agent is a compound chosen from MGBG, MDL73811, CGP48664, Berenil, Pentamidine, SL47, and SL93, or a combination of two or more thereof. In yet another embodiment, the agent is MGBG, SL47 or SL93. In still another embodiment, two or more agents are used in the methods of the invention to regulate the activity of osteopontin. The two or more agents can be used either sequentially or simultaneously.

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "substantially" as used herein is intended to mean predominantly or having the overriding characteristic of, such that any opposing or detracting characteristics reach a level of insignificance. By way of example, a composition "substantially" free of water might not be absolutely free of all traces of water, but would be sufficiently anhydrous that any remaining water would not influence the composition in any significant way. By way of further example, "substantially dose-limiting side effects" might be side effects which limited a dose to a level which was below that required for therapeutic efficacy.

The following standard abbreviations are used to represent the associated pharmacokinetic parameters.

| | |
|---|---|
| AUC | Area under the curve up to the last measurable concentration plus the AUC extrapolated from the last measurable concentration ($C_{last}$ at $t_{last}$) to infinity: $AUC_{INFobs} = AUC_{0-tlast} + C_{last}/\text{Lambda z}$ (where $\lambda z$ is the first order rate constant associated with the terminal (log-linear) portion of the curve) |
| $AUC_{0-12}$ | Area under the curve between the time of dose and the 12 h time point |
| $AUC_{0-24}$ | Area under the curve between the time of dose and the 24 h time point |
| F | Fraction available (bioavailability): $F = [AUC_{oral}] \cdot dose_{iv}/[AUC_{iv}] \cdot dose_{oral}$ |
| $Cl_{obs}$ | Observed clearance |
| $Vss_{obs}$ | Steady state volume of distribution |
| $V_d$ | Volume of distribution (often used with oral) |
| $Cl/F_{obs}$ | Apparent total body clearance as a function of bioavailability |
| $t_{1/2}$ | Terminal half-life ($HL_{\lambda z}$) |
| $C_{max}$ | The maximum observed concentration |
| $T_{max}$ | The time at which $C_{max}$ occurred |

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

A "proliferative disorder" may be any disorder characterized by dysregulated cellular proliferation. Examples include cancers, psoriasis, and atopic dermatitis.

As used herein, "hyperalgesia" means a heightened sensitivity to pain, and can be considered a type of pain or a measure of pain-related behavior.

As used herein, reference to "treatment" of a patient is intended to include prophylaxis. Treatment may also be pre-emptive in nature, i.e., it may include prevention of disease.

Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "patient" is generally synonymous with the term "subject" and means an animal differing from a diseases, disorder, or condition treatable in accordance with the methods disclosed herein, including all mammals and humans. Examples of patients include humans, livestock such as cows, goats, sheep, pigs, and rabbits, and companion animals such as dogs, cats, rabbits, and horses. Preferably, the patient is a human.

An "effective amount" or a "therapeutically effective amount" is a quantity of a compound (e.g., MGBG, a polyamine analog, a polyamine biosynthesis inhibitor or any agent) that is sufficient to achieve a desired effect in a subject being treated. For instance, this can be the amount necessary to treat a disease, disorder, condition, or adverse state (such as pain or inflammation) or to otherwise measurably alter or alleviate the symptoms, markers, or mechanisms of the disease, disorder, condition, or adverse state. As just one example, an effective amount for the treatment of pain is an amount sufficient to prevent, delay the onset of, or reduce pain or one or more pain-related symptoms in a subject, as measured by methods known in the art. Similar methods of assessing response to treatment of a number of diseases are well-known in the art. The effective amount of a compound of the present invention may vary depending upon the route of administration and dosage form. In addition, specific dosages may be adjusted depending on conditions of disease, the age, body weight, general health conditions, sex, and diet of the subject, dose intervals, administration routes, excretion rate, and combinations of agents.

The term "low dose," in reference to a low dose formulation of a drug or a method of treatment specifically employing a "low dose" of a drug, means a dose which for at least one indication is subtherapeutic, or is a fraction of the dose typically given for at least one indication. Take for example the case of a drug for the treatment of proliferative disorders—a low dose formulation for the treatment of, say, chronic psoriasis, might be a fraction of the dose for the treatment of an aggressive cancer. In this way, the dose for one disease might be an amount which would be subtherapeutic for another disease. Alternatively, for a drug which is therapeutic in different individuals or populations at different doses, and is available in a range of doses, a low dose may be simply a dose toward the low end of recognized therapeutic efficacy. Chronic diseases represent an embodiment treatable by low dose formulations and methods. Additionally, a subtherapeutic amount of a drug might be used in combination with one or more other drugs (themselves in either therapeutic or sub-therapeutic amounts) to yield a combination formulation or treatment which is potentiated, that is, more efficacious than the expected effects of the sum of the drugs given alone. A low dose for the treatment of one indication may be two-fold, three-fold, four-fold, five-fold, six-fold, seven-fold, eight-fold, nine-fold, ten-fold, fifteen-fold, twenty-fold, thirty-fold, forty-fold, fifty-fold, may be one hundred-fold less than the therapeutic dose for a different indication.

The term "therapeutically acceptable" refers to those compounds (or salts, prodrugs, tautomers, zwitterionic forms, etc.) which are suitable for use in contact with the tissues of subjects without undue toxicity, irritation, and allergic response, are commensurate with a reasonable benefit/risk ratio, and are effective for their intended use.

The term "drug" is used herein interchangeably with "compound," "agent," and "active pharmaceutical ingredient" ("API").

As used herein, a "polyamine" is any of a group of aliphatic, straight-chain amines derived biosynthetically from amino acids; polyamines are reviewed in Marton et al. (1995) *Ann. Rev. Pharm. Toxicol.* 35:55-91. By "polyamine" is generally meant a naturally-occurring polyamine or a polyamine which is naturally produced in eukaryotic cells. Examples of polyamines include putrescine, spermidine, spermine and cadaverine.

As used herein, a "polyamine analog" is an organic cation structurally similar but non-identical to naturally-occurring polyamines such as spermine and/or spermidine and their precursor, diamine putrescine. Polyamine analogs can be branched or un-branched, or incorporate cyclic moieties. Polyamines may comprise primary, secondary, tertiary, or quaternary amino groups. In certain embodiments, all the nitrogen atoms of the polyamine analogs are independently secondary, tertiary, or quaternary amino groups, but are not so limited. Polyamine analogs may include imine, amidine and guanidine groups in place of amine groups. The term "polyamine analog" includes stereoisomers, salts and protected derivatives of polyamine analogs.

A "stereoisomer" is any optical isomer of a compound, including enantiomers and diastereomers. Unless otherwise indicated, structural formulae of compounds are intended to embrace all possible stereoisomers.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The term "controlled release" in reference to a formulation or dosage form means that release of active drug (e.g., MGBG) from the dosage form is controlled through the use of ingredients that retard, dissolution of the dosage form or efflux of the drug from the dosage form. The term includes extended-release, sustained-release, delayed-release, and pulsed-release (cycled release).

The term to "substantially dissolve," as used herein in reference to a dosage form, means to dissolve to a degree that is clinically relevant. For example, when an enterically coated dosage form begins to substantially dissolve, it would begin to release drug into the GI tract to a degree that would, within the time necessary for drug to be absorbed from the GI lumen and distributed into the plasma, yield a clinically relevant plasma concentration. A clinically relevant plasma concentration might be, for example, a therapeutically effective plasma concentration. Alternatively, it might be near a therapeutically effective plasma concentration; for example, it might be between about 50% and 100% of a therapeutically effective plasma concentration, between about 80% and 100% of a therapeutically effective plasma concentration, between about 90% and 100% of a therapeutically effective plasma concentration, between about 95% and 100% of a therapeutically effective plasma concentration, or between about 99% and 100% of a therapeutically effective plasma concentration. Alternatively, a clinically relevant plasma concentration might be a plasma concentration at which adverse effects are seen, or near such a concentration, for example between about 50% and 100%, between about 60% and 100%, between about 70% and 100%, between about 80% and 100%, between about 90% and 100%, or between about 95% and 100% of such a concentration. Alternatively, substantially dissolved might mean about 50%, about 55%, about 60%, about 65%, about 70%, about 75%, about 800%, about 85%, about 90%, or about 95% dissolved. A dosage form is not "substantially dissolved" when it dissolves only to the extent that it releases a detectable, but otherwise irrelevant, amount of drug into the GI tract.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

Provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The optimal dose, frequency of administration, and duration of treatment with the agent in a subject may vary from subject to subject, depending on the disease to be treated or clinical endpoint to be reached (for example, decrease in the level or activity of osteopontin, inhibition of infiltration of macrophages to a tissue, or mitigation of pain) the subject's condition, the subject's age, weight, response to the treatment, and the nature of the therapeutic entity. Determination of the optimal dose and duration of treatment is within the scope of one of skill in the art. The optimal dose and duration of treatment may be best determined by monitoring the subject's response during the course of the treatment. In some instances, the administration of higher doses may permit less frequent administration, and lower doses may require more frequent administration in order to achieve a clinically significant improvement in the subject's condition. The agent(s) of the invention may be administered as a single dose or in multiple doses.

Generally, a therapeutically effective dose of the agent in accordance with the present methods will be one or more doses of from about 10 to about 1100 mg/m$^2$. Lower dose regimens include doses of 10-200, 10-100, 10-50 and 20-200 mg/m$^2$. Higher dose regimens include 200-400, 250-500, 400-600, 500-800 600-1000 and 800-1100 mg/m$^2$. In certain embodiments, the dose regimens range from 200-400 mg/m$^2$. In another embodiment, the dose regimens range from 250-500 mg/m$^2$. In yet another embodiment, the dose regimens range from 600-1000 mg/m$^2$. In some embodiments the agent is administered daily, once per week, once every other week, or once per month. In certain embodiments, a dose regimen ranging from 200-400 mg/m$^2$ is administered once a week. In another embodiment, a dose regimen ranging from 250-500 mg/m$^2$ is administered once every other week.

The doses may be constant over the entire treatment period, or they may increase or decrease during the course of the treatment. In certain embodiments, the agent is administered once a week and starts with the administration of 200 mg/m$^2$, and increases to 300 mg/m$^2$ and 400 mg/m$^2$ in the second and third weeks, respectively. In another embodiment, the agent is administered once every other week and is kept constant for the entire duration of treatment with the administration of 250 mg/m$^2$. The doses of the agent may be administered for at least one week, at least two weeks, at least three weeks, at least four weeks, at least 6 weeks, or even at least 8 weeks. Adjusting the dose of the agent within these ranges for a particular subject is well within the skill of the ordinary clinician.

The agent may be administered via any conventional route normally used to administer a medicament including, but not limited to, oral, parenteral (including subcutaneous, intradermal, intramuscular, intravenous, intraarticular, and intramedullary), intraperitoneal, transmucosal (including nasal), transdermal, rectal and topical (including dermal, buccal, sublingual and intraocular) routes. Intravenous delivery may take place via a bolus injection or via infusion; infusion may be done over a period ranging from less than a minute to several hours to continuously. In certain embodiments, a course of treatment will involve administration by a combination of routes.

For example, the agent may be administered via a combination of intravenous and oral routes for the treatment of pain or another disorder. In one embodiment, a "loading" dose may be administered IV in order to bring the concentration of drug to the desired therapeutic level, followed by one or more maintenance doses via the oral route to keep it there. In a further embodiment, a combination of oral and IV delivery may be used to mitigate pain in a surgery patient. The agent may be delivered pre-, peri-, and post-surgically by a combination of IV and oral routes. In one embodiment, the patient may be administered or may self-administer the drug orally prior to surgery, be administered the drug via IV infusion during surgery and just after, and may thereafter be administered or may self-administer the drug orally or intravenously (patient-controlled analgesia pumps) after surgery. In another embodiment, the patient may be administered the drug IV prior to surgery, be administered the drug via IV infusion during surgery and just after, and may thereafter be administered or may self-administer the drug orally after surgery.

The agent may be administered as a pharmaceutical composition in a variety of forms including, but not limited to, liquid, powder, suspensions, tablets, pills, capsules, sprays and aerosols. The pharmaceutical compositions may include various pharmaceutically acceptable additives including, but not limited to, carriers, excipients, binders, stabilizers, antimicrobial agents, antioxidants, diluents and/or supports. Examples of suitable excipients and carriers are described, for example, in "Remington's Pharmaceutical Sciences," Mack Pub. Co., New Jersey (1991). In some embodiments, the agent may be administered via an IV infusion in an aqueous sugar solution. The agent may also be associated with another substance that facilitates agent delivery. For example, the agent may be associated into liposomes. The liposomes, in turn, may be conjugated with targeting substance(s), such as IgGFc receptors.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Oral pharmaceutical preparations include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Exemplary unit dosage formulations are those containing an effective dose, as herein below recited, or an appropriate fraction thereof, of the active ingredient.

Fillers to be used in the compositions herein include all those now known and in use, as well as those developed in the future. Examples of fillers, or diluents, include, without limitation, lactose, mannitol, xylitol, dextrose, sucrose, sorbitol, compressible sugar, microcrystalline cellulose (MCC), powdered cellulose, cornstarch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose. Fillers may have complexed solvent molecules, such as in the case where the lactose used is lactose monohydrate. Fillers may also be proprietary, such as in the case of the filler PROSOLV® (available from JRS Pharma). PROSOLV® is a proprietary, optionally high-density, silicified microcrystalline cellulose composed of 98% microcrystalline cellulose and 2% colloidal silicon dioxide. Silicification of the microcrystalline cellulose is achieved by a patented process, resulting in an intimate association between the colloidal silicon dioxide and microcrystalline cellulose. PROSOLV® comes in different grades based on particle size, and is a white or almost white, fine or granular powder, practically insoluble in water, acetone, ethanol, toluene and dilute acids and in a 50 g/l solution of sodium hydroxide.

Disintegrants to be used in the compositions herein include all those now known and in use, as well as those developed in the future. Examples of disintegrants include, without limitation, sodium starch glycolate, sodium carboxymethyl cellulose, calcium carboxymethyl cellulose, croscarmellose sodium, povidone, crospovidone (polyvinylpolypyrrolidone), methyl cellulose, microcrystalline cellulose, powdered cellulose, low-substituted hydroxy propyl cellulose, starch, pregelatinized starch, and sodium alginate.

Lubricants to be used in the compositions herein include all those now known and in use, as well as those developed in the future. Examples of lubricants include, without limitation, calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Glidants to be used in the compositions herein include all those now known and in use, as well as those developed in the future. Examples of glidants include, without limitation, silicon dioxide ($SiO_2$), talc cornstarch, and poloxamers. Poloxamers (or LUTROL®, available from the BASF Corporation) are A-B-A block copolymers in which the A segment is a hydrophilic polyethylene glycol homopolymer and the B segment is hydrophobic polypropylene glycol homopolymer.

Tablet binders to be used in the compositions herein include all those now known and in use, as well as those developed in the future. Examples of tablet binders include, without limitation, acacia, alginic acid, carbomer, carboxymethyl cellulose sodium, dextrin, ethylcellulose, gelatin, guar gum, hydrogenated vegetable oil, hydroxyethylcellulose, hydroxypropyl cellulose, hydroxypropylmethyl cellulose, copolyvidone, methyl cellulose, liquid glucose, maltodextrin, polymethacrylates, povidone, pregelatinized starch, sodium alginate, starch, sucrose, tragacanth, and zein.

Examples of surfactants include, without limitation, fatty acid and alkyl sulfonates; commercial surfactants such as benzethanium chloride (HYAMINE® 1622, available from Lonza, Inc., Fairlawn, N.J.); DOCUSATE SODIUM® (available from Mallinckrodt Spec. Chem., St. Louis, Mo.); polyoxyethylene sorbitan fatty acid esters (TWEEN®, available from ICI Americas Inc., Wilmington, Del.; LIPOSORB® P-20, available from Lipochem Inc., Patterson N.J.; CAPMUL® POE-0, available from Abitec Corp., Janesville, Wis.), polyoxyethylene (20) sorbitan monooleate (TWEEN 80®, available from ICI Americas Inc., Wilmington, Del.); and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug Drug complexing agents and solubilizers to be used in the compositions herein include all those now known and in use, as well as those developed in the future. Examples of drug complexing agents or solubilizers include, without limitation, the polyethylene glycols, caffeine, xanthene, gentisic acid and cyclodextrins.

The addition of pH modifiers such as acids, bases, or buffers may also be beneficial, retarding or enhancing the rate of dissolution of the composition, or, alternatively, helping to improve the chemical stability of the composition. Suitable pH modifiers to be used in the compositions herein include all those now known and in use, as well as those developed in the future.

It should be understood that in addition to the ingredients particularly mentioned above, the formulations provided herein may include other agents conventional in the art having regard to the type of formulation in question. Proper formulation is dependent upon the route of administration chosen. Any of the well-known techniques, carriers, and excipients may be used as suitable and as understood in the art; e.g., Remington, supra. The pharmaceutical compositions may be manufactured in a manner that is itself known, e.g., by means of conventional mixing, dissolving, granulating, dragee-making, levigating, emulsifying, encapsulating, entrapping or compression processes.

Compounds may be generally administered orally at a dose of from 0.1 to about 500 mg/kg per day. The dose range for adult humans is generally from about 5 mg to about 2 g/day. Tablets, capsules, or other forms of presentation provided in discrete units may conveniently contain an amount of one or more compounds which is effective at such dosage or as a multiple of the same, for instance, units containing about 5 mg to about 500 mg. In certain embodiments, an oral dosage form will comprise about 20 to about 400 mg, about 25 to about 350 mg, about 100 to about 350 mg, about 200 to about 350 mg, or about 300 to about 350 mg.

The precise amount of compound administered to a subject will be the responsibility of the attendant physician. The specific dose level for any particular subject will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity. Dosing frequency may also be selected or adjusted based on factors including those above as well as the formulation of the compound delivered. Dosing may occur, for example: once daily, twice daily, three or four times daily, every other day, weekly, bi-weekly, or monthly; or in cycles comprising a sustained dosing period followed by a non-dosing period; or on an as-needed basis.

In certain instances, it may be appropriate to administer at least one of the compounds described herein (or a pharmaceutically acceptable salt, ester, or prodrug thereof) in combination with another therapeutic agent. By way of example only, if one of the side effects experienced by a subject upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the subject is enhanced). Or, by way of example only, the benefit experienced by a subject may be increased by administering one of the compounds described herein with another therapeutic agent (which also includes a therapeutic regimen) that also has therapeutic benefit. By way of example only, in a treatment for neuropathy involving administration of one of the compounds described herein, increased therapeutic benefit may result by also providing the subject with another therapeutic agent for neuropathy. In any case, regardless of the disease, disorder or condition being treated, the overall benefit experienced by the subject may simply be additive of the two therapeutic agents or the subject may experience a synergistic benefit.

In certain embodiments, the other therapeutic agent is an antiviral agent. In one embodiment, the antiviral agent is an antiretroviral agent, e.g. nucleoside reverse transcriptase inhibitors, nucleotide reverse transcriptase inhibitors, non-nucleoside reverse transcriptase inhibitors, protease inhibitors, entry inhibitors, integrase inhibitors or gp41, CXCR4, or gp120 inhibitors. Examples of nucleoside reverse transcriptase inhibitors for the treatment of HIV infections include amdoxovir, elvucitabine, alovudine, racivir (±-FTC), phosphazide, fozivudine tidoxil, apricitibine (AVX754), amdoxovir, zidovudine (AZT), didanosine (ddI), lamivudine (3TC), stavudine (d4T), zalcitabine (ddC), emtricitabine (FTC), and abacavir (ABC). Examples of nucleotide reverse transcriptase inhibitors include tenofovir (TDF) and adefovir. Examples of non-nucleoside reverse transcriptase inhibitors include capravirine, emivirine, calanolide A, etravirine, efavirenz (EFV), nevirapine (NVP) and delavirdine (DLV). Examples of protease inhibitors include amprenavir (APV), tipranavir (TPV), lopinavir (LPV), fosamprenavir (FPV), atazanavir (ATV), darunavir, brecanavir, mozenavir, indinavir (IDV), nelfinavir (NFV), ritonavir (RTV), and saquinavir (SQV). Examples of entry inhibitors include SPOIA. Examples of a HIV integrase inhibitor include curcumin, derivatives of curcumin, chicoric acid, derivatives of chicoric acid, 3,5-dicaffeoylquinic acid, derivatives of 3,5dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-25 870810, MK-0518, BMS-538158, GSK364735C, Examples of a gp41 inhibitor include enfuvirtide (ENF). Examples of a CXCR4 inhibitor include AMD-070, Examples of a gp120 inhibitor include BMS-488043.

In another embodiment, the polyamine analog is administered concurrently with a highly active antiretroviral therapy (HAART), i.e., a combination of a protease inhibitor, a non-nucleoside reverse transcriptase inhibitor and a nucleoside reverse transcriptase inhibitor, or a combination of two non-nucleoside reverse transcriptase inhibitors and a nucleoside reverse transcriptase inhibitor. In general, the polyamine analog may be administered simultaneously or sequentially (i.e., before or after) with the administration of antiviral or antiretroviral agents. Administration of the antiviral and antiretroviral agents to subjects in need thereof can be made in accordance with regimens and dosages well known in the art.

In yet other embodiments, the antiviral agent is an agent that is capable of reducing the HIV viral load in T-cells. T-cells, particularly CD4+ T-cells, also serve as a viral reservoir for immunodeficiency viruses such as HIV. Thus, combination treatments of polyamine analogs with agents that reduce the viral load in T-cells are particularly desirable for flushing or destroying viral reservoirs of HIV. Suitable agents that reduce the viral load in T-cells are reviewed in Pierson et al. (Annu. Rev. Immunol. (2000), 18:665-708) and include, without limitation, T-cell activating cytokines, anti-CD3 antibodies, and anti-CD45RO-toxin conjugates. For example, T-cell activating cytokines such as IL-2, IL-6, TNF-α, and any two or more combinations thereof may be used in the present methods.

In other embodiments, the other therapeutic agent is a TNF inhibitor. The TNF inhibitor may be: a monoclonal antibody such as, for example, infliximab (Remicade), adalimumab (Humira), certolizumab pegol (Cimzia), or golimumab (Simponi); a circulating receptor fusion protein such as etanercept (Enbrel); or a small molecule, such as pentoxifylline or bupropion (Zyban, Wellbutrin).

In other embodiments, the other therapeutic agent is a disease-modifying anti-rheumatic drug (DMARD). Examples of DMARDs include azathioprine, cyclosporin (cyclosporine A), D-penicillamine, gold salts, hydroxychloroquine, leflunomide, methotrexate (MTX), minocycline, sulfasalazine (SSZ), and cyclophosphamide.

In further embodiments, the other therapeutic agent is methotrexate.

Other agents for used in combination include interleukin 1 (IL-1) blockers such as anakinra (Kineret), T-cell costimulation blockers such as abatacept (Orencia), interleukin 6 (IL-6) blockers such as tocilizumab (an anti-IL-6 receptor antibody; RoActemra, Actemra), monoclonal antibodies against B cells such as rituximab (Rituxan), and other biologics (eg. Ocrelizumab, Ofatumumab, Golimumab, and Certolizumab pegol).

In other embodiments, the other therapeutic agent is a glucocorticoid or a non-steroidal anti-inflammatory drug (NSAID). NSAIDS include propionic acid derivatives such as ibuprofen, naproxen, fenoprofen, ketoprofen, flurbiprofen, and oxaprozin; acetic acid derivatives such as indomethacin, sulindac, etodolac, and diclofenac; enolic acid (oxicam) derivatives such as piroxicam and meloxicam; fenamic acid derivatives such as mefenamic acid and meclofenamic acid; selective COX-2 inhibitors (Coxibs) such as celecoxib (Celebrex), rofecoxib, valdecoxib, parecoxib, lumiracoxib, and etoricoxib.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the doses of the multiple therapeutic agents may be any duration of time ranging from a few minutes to four weeks.

Thus, in another aspect, certain embodiments provide methods for treating disorders in a human or animal subject in need of such treatment comprising administering to said subject an amount of a compound disclosed herein effective to reduce or prevent said disorder in the subject, optionally in combination with at least one additional agent for the treatment of said disorder that is known in the art. Specific diseases to be treated by the compounds, compositions, and methods disclosed herein, singly or in combination, include, without limitation: pain; neuropathy; inflammation and related disorders; arthritis; metabolic inflammatory disorders; respiratory disorders; autoimmune disorders; neurological disorders; and proliferative disorders, including cancer and non-cancerous diseases.

The compounds disclosed herein are useful to treat patients with pain, including neuropathy and/or neuropathic pain, and inflammatory pain. Pain indications include, but are not limited to, treatment or prophylaxis of surgical or post-surgical pain for various surgical procedures including amputation, post-cardiac surgery, dental pain/dental extraction, pain resulting from cancer, muscular pain, mastalgia, pain resulting from dermal injuries, lower back pain, headaches of various etiologies, including migraine, menstrual cramps, and the like. The compounds are also useful for the treatment of pain-related disorders such as tactile allodynia and hyperalgesia. The pain may be somatogenic (either nociceptive or neuropathic), acute and/or chronic. Peripheral neuropathies which can be treated with the compounds disclosed herein include mono-neuropathies, mono-multiplex neuropathies, and poly-neuropathies, including axonal and demyelinating neuropathies. Both sensory and motor neuropathies are encompassed. The neuropathy or neuropathic pain may be associated with a number of peripheral neuropathies of varying etiologies, including but not limited to:

- trauma-induced neuropathies, including those caused by physical injury (such as blunt trauma, abrasion, or burns) or disease state, physical damage to the brain, physical damage to the spinal cord, or stroke associated with brain damage; neurological disorders related to neurodegeneration; and post-surgical neuropathies and neuropathic pain (such as from tumor resection, mastectomy, and the like)
- infectious and viral neuropathies, including those caused by leprosy, Lyme disease, a herpes virus (and more particularly by a herpes zoster virus, which may lead to post-herpetic neuralgia), human immunodeficiency virus (HIV, which may lead to HIV neuropathy), or a papilloma virus, or any other pathogen-induced nerve damage;
- toxin-induced neuropathies (including but not limited to neuropathies induced by alcoholism, vitamin B6 intoxication, hexacarbon intoxication, amiodarone, chloramphenicol, disulfuram, isoniazide, gold, lithium, metronidazole, misonidazole, nitrofurantoin);
- drug-induced neuropathies, including therapeutic-drug-induced neuropathy, particularly a) chemotherapy-induced neuropathies caused by anti-cancer agents such as taxol, taxotere, cisplatin, nocodazole, vincristine, vindesine and vinblastine, and b) anti-viral neuropathies caused by anti-viral agents such as ddI, DDC, d4T, foscarnet, dapsone, metronidazole, and isoniazid);
- vitamin-deficiency-induced neuropathies including those resulting from vitamin B12 deficiency, vitamin B6 deficiency, and vitamin E deficiency);
- hereditary neuropathy (including but not limited to Friedreich ataxia, familial amyloid polyneuropathy, Tangier disease, Fabry disease;
- diabetic neuropathy and neuropathy caused by metabolic disorders such as renal insufficiency and hypothyroidism;
- neuropathy secondary to tumor infiltration;
- auto-immune neuropathies, including those resulting from Guillain-Barre syndrome, chronic inflammatory de-myelinating polyneuropathy, monoclonal gammopathy of undetermined significance and polyneuropathy, and multiple sclerosis;
- other neuropathies and neuropathic pain syndromes including inflammation-induced nerve damage, neurodegeneration, post-traumatic neuralgia, central neuropathic pain syndromes such as phantom limb pain, pain, complex regional pain syndromes (including but not limited to reflex sympathetic dystrophy, causalgia), neoplasia-associated pain, vasculitic/angiopathic neuropathy, and sciatica; and
- idiopathic neuropathies, In certain embodiments, neuropathic pain may alternatively be manifested as allodynia, hyperalgesic pain, thermal hyperalgesia, or phantom pain. In another embodiment, neuropathy may instead lead to loss of pain sensitivity. Additional sub-categories of neuropathic pain are discussed in Dworkin, *Clin J Pain* (2002) vol. 18(6) pp. 343-9.

Furthermore, the compounds disclosed herein can be used in the treatment or prevention of opiate tolerance in patients needing protracted opiate analgesics, and benzodiazepine tolerance in patients taking benzodiazepines, and other addictive behavior, for example, nicotine addiction, alcoholism, and eating disorders. Moreover, the compounds disclosed herein are useful in the treatment or prevention of drug withdrawal symptoms, for example treatment or prevention of symptoms of withdrawal from opiate, alcohol, or tobacco addiction.

The compounds disclosed herein are useful in therapeutic methods to treat or prevent respiratory disease or conditions, including therapeutic methods of use in medicine for preventing and treating a respiratory disease or condition including: asthmatic conditions including allergen-induced asthma, exercise-induced asthma, pollution-induced asthma, cold-induced asthma, and viral-induced-asthma; chronic obstructive pulmonary diseases including chronic bronchitis with normal airflow, chronic bronchitis with airway obstruction (chronic obstructive bronchitis), emphysema, asthmatic bronchitis, and bullous disease; and other pulmonary diseases involving inflammation including bronchioectasis, cystic fibrosis, hypersensitivity pneumonitis, farmer's lung, acute respiratory distress syndrome, pneumonia, aspiration or inhalation injury, fat embolism in the lung, acidosis inflammation of the lung, acute pulmonary edema, acute mountain sickness, acute pulmonary hypertension, persistent pulmonary hypertension of the newborn, perinatal aspiration syndrome, hyaline membrane disease, acute pulmonary thromboembolism, heparin-protamine reactions, sepsis, status asthmaticus, hypoxia, hyperoxic lung injuries, and injury induced by inhalation of certain injurious agents including cigarette smoking, leading up to complications thereof such as lung carcinoma.

Other disorders or conditions which can be advantageously treated by the compounds disclosed herein include inflammation and inflammatory conditions. Inflammatory conditions include, without limitation: arthritis, including subtypes and related conditions such as rheumatoid arthritis, spondyloarthropathies, gouty arthritis, osteoarthritis, systemic lupus erythematosus, juvenile arthritis (including Still's disease), acute rheumatic arthritis, enteropathic arthritis, neuropathic arthritis, psoriatic arthritis, and pyogenic arthritis; osteoporosis, tendonitis, bursitis, and other related bone and joint disorders; gastrointestinal conditions such as reflux esophagitis, diarrhea, inflammatory bowel disease, Crohn's disease, gastritis, irritable bowel syndrome, ulcerative colitis, acute and chronic pancreatitis; pulmonary inflammation, such as that associated with viral infections and cystic fibrosis; skin-related conditions such as psoriasis, eczema, burns, sunburn, dermatitis (such as contact dermatitis, atopic dermatitis, and allergic dermatitis), and hives; pancreatitis, hepatitis, pruritis and vitiligo. In addition, compounds of invention are also useful in organ transplant patients either alone or in combination with conventional immunomodulators.

Autoimmune disorders may be ameliorated by the treatment with compounds disclosed herein. Autoimmune disorders include Crohns disease, ulcerative colitis, dermatitis, dermatomyositis, diabetes mellitus type 1, Goodpasture's syndrome, Graves' disease, Guillain-Barre syndrome (GBS), autoimmune encephalomyelitis, Hashimoto's disease, idiopathic thrombocytopenic purpura, systemic lupus erythematosus, mixed connective tissue disease, multiple sclerosis (MS), myasthenia gravis, narcolepsy, pemphigus vulgaris, pernicious anemia, psoriasis, psoriatic arthritis, polymyositis, primary biliary cirrhosis, rheumatoid arthritis, Sjögren's syndrome, scleroderma, temporal arteritis (also known as "giant cell arteritis"), vasculitis, and Wegener's granulomatosis. The compounds disclosed herein may regulate TH-17 (T-helper cells producing interleukin 17) cells or IL-17 levels, as well as modulate levels of IL-10 and IL-12. They may also regulate cellular production of osteopontin (eg in dendritic cells, monocytes/macrophages, T cells, fibroblasts, and other immunological and non-immunological cell-types).

In addition, the compounds disclosed herein can be used to treat metabolic disorders that are typically associated with an exaggerated inflammatory signaling, such as insulin resistance, diabetes (type I or type II), metabolic syndrome, non-alcoholic fatty liver disease (including non-alcoholic steatohepatitis), atherosclerosis, cardiovascular disease, congestive heart failure, myocarditis, atherosclerosis, and aortic aneurysm.

The compounds disclosed herein are also useful in treating organ and tissue injury associated with severe burns, sepsis, trauma, wounds, and hemorrhage- or resuscitation-induced hypotension, and also in such diseases as vascular diseases, migraine headaches, periarteritis nodosa, thyroiditis, aplastic anemia, Hodgkin's disease, scleroduma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, swelling occurring after injury, ischemias including myocardial ischemia, cardiovascular ischemia, and ischemia secondary to cardiac arrest, and the like.

The compounds of the subject invention are also useful for the treatment of certain diseases and disorders of the nervous system. Central nervous system disorders in which nitric oxide inhibition is useful include cortical dementias including Alzheimer's disease, central nervous system damage resulting from stroke, ischemias including cerebral ischemia (both focal ischemia, thrombotic stroke and global ischemia (for example, secondary to cardiac arrest), and trauma. Neurodegenerative disorders in which nitric oxide inhibition is useful include nerve degeneration or necrosis in disorders such as hypoxia, hypoglycemia, epilepsy, and in cases of central nervous system (CNS) trauma (such as spinal cord and head injury), hyperbaric oxygen-induced convulsions and toxicity, dementia e.g. pre-senile dementia, and AIDS-related dementia, cachexia, Sydenham's chorea, Huntington's disease, Parkinson's Disease, amyotrophic lateral sclerosis (ALS), Korsakoffs disease, cognitive disorders relating to a cerebral vessel disorder, hypersensitivity, sleeping disorders, schizophrenia, depression, depression or other symptoms associated with Premenstrual Syndrome (PMS), and anxiety.

Still other disorders or conditions advantageously treated by the compounds of the subject invention include the prevention or treatment of (hyper)proliferative diseases, especially cancers, either alone or in combination with standards of care especially those agents that target tumor growth by re-instating the aberrant apoptotic machinery in the malignant cells. Hematological and non-hematological malignancies which may be treated or prevented include but are not limited to multiple myeloma, acute and chronic leukemias including acute lymphocytic leukemia (ALL), chronic lymphocytic leukemia (CLL), and chronic myelogenous leukemia (CLL), lymphomas, including Hodgkin's lymphoma and non-Hodgkin's lymphoma (low, intermediate, and high grade), as well as solid tumors and malignancies of the brain, head and neck, breast, lung, reproductive tract, upper digestive tract, pancreas, liver, renal, bladder, prostate and colorectal. The present compounds and methods can also be used to treat the fibrosis, such as that which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP. Non-cancerous proliferative disorders additionally include psoriasis, eczema, and dermatitis.

Compounds disclosed herein may also be used in the treatment of polycystic kidney disease, as well as other diseases of renal dysfunction.

The compounds of the subject invention can be used in the treatment of ophthalmic diseases, such as glaucoma, retinal ganglion degeneration, ocular ischemia, corneal neovascularization, optic neuritis, retinitis, retinopathies such as glaucomatous retinopathy and/or diabetic retinopathy, uveitis, ocular photophobia, dry eye, Sjogren's syndrome, seasonal and chronic allergic conjunctivitis, and of inflammation and pain associated with chronic ocular disorders and acute injury to the eye tissue. The compounds can also be used to treat post-operative inflammation or pain as from ophthalmic surgery such as cataract surgery and refractive surgery.

The present compounds may also be used in co-therapies, partially or completely, in place of other conventional anti-inflammatory therapies, including steroids, NSAIDs, COX-2 selective inhibitors, 5-lipoxygenase inhibitors, $LTB_4$ antagonists and $LTA_4$ hydrolase inhibitors. The compounds of the subject invention may also be used to prevent tissue damage when therapeutically combined with antibacterial or antiviral agents.

Predicted Human Efficacy

Multi-species allometric scaling based on pharmacokinetic parameters was employed to calculate predicted pharmacokinetic parameters in humans according to methods known in the art. See, e.g., Ings R M, "Interspecies scaling and comparisons in drug development and toxicokinetics," *Xenobiotica,* 1990 November; 20(11):1201-31 and Khor, S P et al., "Dihydropyrimidine dehydrogenase inactivation and 5-fluorouracil pharmacokinetics: allometric scaling of animal data, pharmacokinetics and toxicodynamics of 5-fluorouracil in humans," *Cancer Chemother Pharmacol* (1997) 39(3): 833-38. Expected values are given below in Table 2.

TABLE 2

| ORAL | $t_{1/2}$ (h) | CL/F (mL/min/kg) | V/F (L/kg) |
|---|---|---|---|
| Based on Mouse, Rat, Dog, Rhesus | 23.3 | 21.0 | 42.4 |
| Based on Mouse, Dog, Rhesus | 23.0 | 20.9 | 41.6 |

In both the murine carrageenan-induced paw edema and hyperalgesia models, the top efficacious dose of MGBG is 30 mg/kg PO BID (totaling 60 mg/kg/day). Based upon this dosing paradigm in mice, at least two methods to estimate the equivalent dosing in humans may be used.

The first method is based upon body surface area (BSA) normalization (described in Reagen-Shaw et al. (2007) FASEB J. 22, 659-661), as the authors note that BSA correlates well across species for various biological parameters, including basal metabolic rate, blood volume, caloric expenditure, plasma protein levels, and renal function. Using this method, a 60 mg/kg/day dose in mice would convert to about 4.9 mg/kg/day in humans.

The second method used to convert the efficacious 60 mg/kg/day dose in mice to an equivalent dose in humans was based more directly on allometric scaling of actual pharmacokinetic data from various animal species. Data from an MGBG pharmacokinetic study consisting of a 10 mg/kg oral dose in mice was modeled in a simulation to determine the theoretical AUC value for a dosing regimen of 30 mg/kg PO BID, which was 9050 h*ng/mL. Next, predicted human clearance values as determined by single- and multi-species allometric scaling were used to estimate doses likely to produce an exposure in humans ($AUC_1$) similar to that of the 60 mg/kg/day in mice. Using single-species allometric scaling and a range of predicted human clearance values, a human equivalent dose would be in the range of 1.73 mg/kg/day to 4.51 mg/kg/day. Using multi-species allometric scaling, the predicted human equivalent dose is about 4.2 mg/kg/day.

In the murine carrageenan models, we also observed efficacy of MGBG at lower doses, including 3 mg/kg PO BID and 10 mg/kg PO BID, which would proportionally convert to human doses of ~0.42 mg/kg/day and ~1.2 mg/kg/day.

The average body weight of a normal male human is often presumed to be 70 kg. Thus, daily doses based on the predictions above could be estimated to range from about 25 mg/day to about 350 mg/day.

The proper dose depends, of course, on a number of factors. The patient may weigh much more or much less, or be female, elderly, or juvenile, requiring a lower or higher dose. The patient may exhibit a drug metabolic profile which might counsel for a lower or higher dose, such as a low expression level or activity of metabolizing enzymes such as cytochromes $P_{450}$ (CYPs). This low expression or activity level may be due to a number of factors. Polymorphic expression of one or more CYPs (for example CYP2C19 and CYP2D6, though polymorphisms have been described for nearly all the CYPs) is known to be responsible for some populations to be "deficient" as compared to the population at large, leading to a "poor metabolizer" phenotype, requiring a lower dose. Additionally, exposure to an infectious agent or xenobiotic may cause repression of CYP expression or inhibition of existing CYPs. Alternatively, the patient may be physically weak, injured, or immunocompromised, all of which might counsel a lower dose. The patient may be taking a number of other drugs which compete with metabolic systems (including CYPs as discussed above) for disposal; this well-known polypharmaceutical effect may call for a lower dose. The dose also depends, as discussed above, on the condition and its severity. The efficacious dose for one disease or clinical endpoint will not necessarily be the same as the dose for another, and a severe, chronic, or otherwise serious case may call for a higher dose. However, a chronic case may also call for a lower dose administered over a longer or even indefinite period of time. All of these are discussed by way of example to illustrate the variability of ideal dosing; it is within the capacity of the skilled artisan to select an appropriate dosing range for a disease, population, or individual.

With these factors in mind, it should be clear that it is possible that the daily human dose may be as low as 1 mg/day, and as high as a 1 g/day. In certain embodiments, the human dose may range: from 10 mg/day to 500 mg/day, from 20 mg/day to 400 mg/day, or from 25 mg/day to 350 mg/day. In further embodiments, the human dose may range from 120 mg/day to 350 mg/day, from 150 mg/day to 350 mg/day, from 200 mg/day to 350 mg/day, or from 250 mg/day to 350 mg/day. In certain embodiments, the human dose may be any one of 1, 2, 3, 4, 5, 6, 7, 8, 9, 10, 12, 15, 20, 25, 30, 35, 40, 45, 50, 55, 60, 65, 70 75, 80, 85, 90, 95, 100, 110, 120, 125, 130, 140, 150, 160, 170, 175, 180, 190, 200, 210, 220, 225, 230, 240, 250, 260, 270, 275, 280, 290, 300, 310, 320, 325, 330, 240 or 350 mg/day.

In certain embodiments, the human dose may be any one of 275, 280, 285, 290, 295, 300, 305, 310, 315, 320, 325, 330, 335, 340, 350, 355, 360, 365, 370, or 375 mg/day. In one embodiment, the dose may be 275 mg/day. In another embodiment, the dose may be 300 mg/day. In another embodiment, the dose may be 305 mg/day.

In another embodiment, the dose may be 310 mg/day. In another embodiment, the dose may be 315 mg/day. In another embodiment, the dose may be 320 mg/day. In another embodiment, the dose may be 325 mg/day. In another embodiment, the dose may be 330 mg/day. In another embodiment, the dose may be 335 mg/day. In another embodiment, the dose may be 340 mg/day. In another embodiment, the dose may be 345 mg/day. In another embodiment, the dose may be 350 mg/day.

In certain embodiments, the human dose may be any one of 350, 375, 400, 425, 450, 475, 500, 525, 550 or 600 mg/day. In one embodiment, the dose may be 375 mg/day. In another embodiment, the dose may be 400 mg/day. In another embodiment, the dose may be 450 mg/day. In another embodiment, the dose may be 500 mg/day.

In certain embodiments, the human dose may be any one of 25, 50, 75, 100, or 125 mg/day. In one embodiment, the dose may be 375 mg/day. In another embodiment, the dose may be 25 mg/day. In another embodiment, the dose may be 50 mg/day. In another embodiment, the dose may be 75 mg/day. In another embodiment, the dose may be 100 mg/day. In another embodiment, the dose may be 125 mg/day.

Exemplary Oral Pharmaceutical Formulations

The following are examples of dosage forms which may be used to orally deliver compounds disclosed herein.

Extended-Release Examples

The following examples illustrate the formulation of several therapeutic tablet dosage forms. In these examples, the ethylcellulose is typically a dry material of the standard type having a viscosity designation of 4 cps and an ethoxy content of 48% to 49.5%. The hydroxypropylmethylcellulose is typically a dry material having a hydroxypropoxyl content of 7 to 8.6 weight percent.

The carrier base material concentration in the tablet formulae (hydroxypropylmethylcellulose and ethylcellulose) range from 21% to 26.4% (weight by weight). The ethylcellulose to hydroxypropylmethylcellulose weight ratio in the tablet formulae ranges from 1 to 3.2 to 1 to 4.2.

Standard methods known in the art may be used to assess the efficacy of an extended-release formulation.

EXAMPLE 1

This example illustrates the preparation of a tablet with 200 milligrams of MGBG and containing the following ingredients in the listed amounts per tablet.

| Ingredient | mg/tablet |
| --- | --- |
| MGBG, micronized | 200 mg |
| Hydroxypropyl Methylcellulose, USP | 5.0 mg |
| Dibasic Sodium Phosphate, USP | 35.0 mg |
| Lactose, NF | 18.0 mg |
| Ethylcellulose, NF | 17.5 mg |
| Magnesium Stearate, NF | 3.50 mg |
| Talc | 1.00 mg |

Theoretical Tablet Weight = 350 mg

The MGBG together with ethylcellulose, hydroxypropylmethylcellulose, lactose, talc and the dibasic sodium phosphate is dry blended, and subsequently granulated with an alcohol, denatured 23A, and methylene chloride solvent mixture. Instead of using alcohol and methylene chloride as the granulating liquids, other liquids such as tap water may be used instead. Following wet sizing, drying and dry sizing of the granulate, it is blended with magnesium stearate. The final blend is compressed into tablets of the correct weight. Subsequently, an aqueous film coat color suspension and a gloss solution are applied to the tablets. Denatured 23A is a 100:10 blend of ethyl alcohol and acetone.

EXAMPLE 2

This example illustrates the preparation of a tablet with 300 milligrams of MGBG and containing the following ingredients in the listed amounts per tablet.

| Ingredient | mg/tablet |
| --- | --- |
| MGBG, micronized | 300.0 mg |
| Hydroxypropyl Methylcellulose, USP | 112.5 mg |
| Dibasic Sodium Phosphate, USP | 52.5 mg |
| Lactose, NF | 27.0 mg |
| Ethylcellulose, NF | 26.25 mg |
| Magnesium Stearate, NF | 5.25 mg |
| Talc | 1.5 mg |

Theoretical Tablet Weight = 525 mg

The method of manufacture is the same as that of Example 1.

EXAMPLE 3

This example illustrates the preparation of a tablet with 400 milligrams of MGBG and containing the following ingredients in the listed amounts per tablet.

| Ingredient | mg/tablet |
| --- | --- |
| MGBG, micronized | 400.0 mg |
| Hydroxypropyl Methylcellulose, USP | 150.0 mg |
| Dibasic Sodium Phosphate, USP | 70.0 mg |
| Lactose, NF | 36.0 mg |
| Ethylcellulose, NF | 35.0 mg |
| Magnesium Stearate, NF | 7.0 mg |
| Talc | 2.0 mg |

Theoretical Tablet Weight = 700 mg

The method of manufacture is the same as that for Example 1.

EXAMPLE 4

This example illustrates the preparation of a tablet with 600 milligrams of MGBG and containing the following ingredients in the listed amounts per tablet.

| Ingredient | mg/tablet |
| --- | --- |
| MGBG, micronized | 600.0 mg |
| Hydroxypropyl Methylcellulose, USP | 168.0 mg |
| Lactose, NF | 105.8 mg |
| Dibasic Sodium Phosphate, USP | 105.0 mg |
| Ethylcellulose, NF | 52.5 mg |
| Magnesium Stearate, NF | 15.75 mg |
| Talc | 3.0 mg |

Theoretical Tablet Weight = 1050 mg

The method of manufacture is the same as that for Example 1.

The dissolution profile of the above dosage forms may be tested according to standard USP procedures. It is expected that the tablet dosage forms will dissolve faster and release drug more rapidly as the hydroxypropoxyl content increases.

The in vivo performance of the novel dosage forms of this invention may be evaluated in bioavailability studies in comparison with equivalent immediate release dosage forms. Extended-release tablets prepared generally according to Examples 1-4 may be given once a day and evaluated in multi-day steady state bioavailability studies in comparison with capsules or tablets containing an equivalent per-diem amount of conventional immediate release drug given multiple times daily. The extended-release tablets are expected to demonstrate equivalent bioavailability to the immediate-release reference dosage forms. Other pharmacokinetic parameters may be measured as well. The $C_{max}$ and $T_{max}$ values are expected to be lower and later respectively for the extended-release dosage forms.

Encapsulated Micropellet Sustained-Release Examples

EXAMPLE 5

3.2 Kilograms polyvinylpyrrolidone, molecular weight 40,000 (Kollidon 30) is dissolved in 32 liters of isopropanol and 12.8 kilograms of micronized MGBG is dispersed therein. 4.0 kilograms of sugar, 60/80 mesh is placed in the Wurster air suspension coating column. After the air suspension system is in operation with the sugar, the dispersed MGBG is sprayed into the column with the inlet air having a temperature of 60° C., the spray pressure at 4 bars, and the spray rate being 100 ml/min. After completion of the above procedure, operation of the Wurster column is stopped, and the product reserved as "MGBG pellets, Active I."

A second 3.2 kilogram batch of polyvinylpyrrolidone, molecular weight 40,000 (Kollidon 30) is dissolved in 32.0 liters of isopropanol, and dispersed into the resultant mixture is 12.8 kilograms of micronized MGBG. 4.0 kilograms of "MGBG pellets, Active I" are then charged into the same Wurster column under the same conditions of temperature and pressure, and at the same rate. The second batch having the MGBG dispersed therein is then charged into the Wurster column to further build up the coating. The Wurster column is emptied and the product labelled "MGBG pellets, Active II".

A coating mixture of 13.2 liters of chloroform and 3.3 liters of methanol is prepared, into which are dispersed 992.0 grams of ethylcellulose (Ethocel N-10 Dow) and 329.0 grams of hydroxypropyl cellulose (Hercules, Klucel LF). Into the Wurster column is charged 19.0 kilograms of "MGBG pellets, Active II," which are then coated with the coating mixture under conditions of 30° C., spray pressure 3 bars and spray rate 100 ml/min. The resultant coated pellets are small micropellets which may be placed into capsules containing the desired dosage unit.

The above protocol may be scaled appropriately according to methods known in the art.

EXAMPLE 6

Using a procedure similar to that described in Example 5, MGBG pellets may be outer coated with 5% by weight of a mixture containing 75% by weight ethylcellulose and 25% by weight hydroxypropylcellulose. The release characteristics of the coated pellets may be measured according to the U.S.P. XX dissolution procedure (one hour in simulated gastric fluid followed by simulated intestinal fluid).

Spheronized Extended-Release Examples

EXAMPLE 7

A mixture of 44.8 parts of MGBG, 74.6 parts of the microcrystalline cellulose, NF, and 0.60 parts of hydroxypropylmethyl cellulose 2208, USP, are blended with the addition of 41.0 parts water. The plastic mass of material is extruded, spheronized and dried to provide uncoated drug containing spheroids.

Stir 38.25 parts of ethyl cellulose, NF, HG2834 and 6.75 parts of hydroxypropylmethylcellulose 2910, USP in a 1:1 v/v mixture of methylene chloride and anhydrous methanol until solution of the film coating material is complete.

To a fluidized bed of the uncoated spheroids is applied 0.667 parts of coating solution per part of uncoated spheroids to obtain extended release, film coated spheroids having a coating level of 3%.

The spheroids are sieved to retain the coated spheroids of a particle size between 0.85 mm to 1.76 mm diameter. These selected film coated spheroids are filled into pharmaceutically acceptable capsules conventionally, such as starch or gelatin capsules.

EXAMPLE 8

Same as for Example 7 except that 1.11 parts of the film coating solution per part of uncoated spheroids is applied to obtain a coating level of 5%.

EXAMPLE 9

Same as for Example 7 except that 1.33 parts of the film coating solution is applied to 1 part of uncoated spheroids to obtain a coating level of 6%.

EXAMPLE 10

Same as for Example 7 except that 1.55 parts of the film coating solution is applied to 1 part of uncoated spheroids to obtain a coating level of 7%.

EXAMPLE 11

MGBG 100-mg Tablets

The required quantities of MGBG, spray-dried lactose, and EUDRAGIT® RS PM are transferred into an appropriate-size mixer, and mixed for approximately 5 minutes. While the powders are mixing, the mixture is granulated with enough water to produce a moist granular mass. The granules are then dried in a fluid bed dryer at 60° C., and then passed through an 8-mesh screen. Thereafter, the granules are redried and pushed through a 12-mesh screen. The required quantity of stearyl alcohol is melted at approximately 60°-70° C., and while the granules are mixing, the melted stearyl alcohol is added. The warm granules are returned to the mixer.

The coated granules are removed from the mixer and allowed to cool. The granules are then passed through a 12-mesh screen. The granulate is then lubricated by mixing the required quantity of talc and magnesium stearate in a suitable blender. Tablets are compressed to 375 mg in weight on a suitable tableting machine. The formula for the tablets of Example 11 is set forth below:

| Component | mg/Tablet | % (by wt) |
|---|---|---|
| MGBG | 100.0 | 27 |
| Lactose (spray-dried) | 143.75 | 38 |
| EUDRAGIT ® RS PM | 45.0 | 12 |
| Purified Water q.s* | — | — |
| Stearyl Alcohol | 75.0 | 20 |
| Talc | 7.5 | 2 |
| Magnesium Stearate | 3.75 | 1 |
| Total: | 375.0 | 100% |

*Used in manufacture and remains in final product as residual quantity only.

The tablets of Example 11 are then tested for dissolution via the USP Basket Method, 37° C., 100 RPM, first hour 700 ml gastric fluid at pH 1.2, then changed to 900 ml at 7.5.

EXAMPLE 12

MGBG 50 mg Controlled Release Tablets

The required quantities of MGBG and spray dried lactose are transferred into an appropriate sized mixer and mix for approximately 6 minutes. Approximately 40 percent of the required EUDRAGIT® RS PM powder is dispersed in Ethanol. While the powders are mixing, the powders are granulated with the dispersion and the mixing continued until a moist granular mass is formed. Additional ethanol is added if needed to reach granulation end point. The granulation is transferred to a fluid bed dryer and dried at 30° C.; and then passed through a 12-mesh screen. The remaining EUDRAGIT® RS PM is dispersed in a solvent of 90 parts ethanol and 10 parts purified water; and sprayed onto the granules in the fluid bed granulator/dryer at 30° C. Next, the granulate is passed through a 12-mesh screen. The required quantity of stearyl alcohol is melted at approximately 60°-70° C. The warm granules are returned to the mixer. While mixing, the melted stearyl alcohol is added. The coated granules are removed from the mixer and allowed to cool. Thereafter, they are passed through a 12-mesh screen.

Next, the granulate is lubricated by mixing the required quantities of talc and magnesium stearate in a suitable blender. The granulate is then compressed to 125 mg tablets on a suitable tableting machine.

The formula for the tablets of Example 12 (10 mg controlled release MGBG) is set forth below:

| Component | mg/Tablet | % (by wt) |
|---|---|---|
| MGBG | 50.00 | 40 |
| Lactose (spray-dried) | 31.25 | 25 |
| EUDRAGIT ® RS PM | 15.00 | 12 |
| Ethanol q.s.* | — | — |

| Component | mg/Tablet | % (by wt) |
| --- | --- | --- |
| Purified Water q.s.* | — | — |
| Stearyl Alcohol | 25.00 | 20 |
| Talc | 2.50 | 2 |
| Magnesium stearate | 1.25 | 1 |
| Total: | 125.00 mg | 100% |

*Used only in the manufacture and remains in final product as residual quantity only.

The tablets of Example 12 are then tested for dissolution via USP Basket Method at 37° C., 100 RPM, first hour 700 ml simulated gastric (pH 1.2) then changed to 900 ml at pH 7.5.

EXAMPLES 13-14

Controlled Release MGBG 50 and 25 mg Tablets (Aqueous Manufacture)

EUDRAGIT® RS 30D and TRIACETIN® are combined while passing though a 60 mesh screen, and mixed under low shear for approximately 5 minutes or until a uniform dispersion is observed.

Next, suitable quantities of MGBG, lactose, and povidone are placed into a fluid bed granulator/dryer (FBD) bowl, and the suspension sprayed onto the powder in the fluid bed. After spraying, the granulation is passed through a #12 screen if necessary to reduce lumps. The dry granulation is placed in a mixer.

In the meantime, the required amount of stearyl alcohol is melted at a temperature of approximately 70° C. The melted stearyl alcohol is incorporated into the granulation while mixing. The waxed granulation is transferred to a fluid bed granulator/dryer or trays and allowed to cool to room temperature or below. The cooled granulation is then passed through a #12 screen. Thereafter, the waxed granulation is placed in a mixer/blender and lubricated with the required amounts of talc and magnesium stearate for approximately 3 minutes, and then the granulate is compressed into 125 mg tablets on a suitable tableting machine.

The formula for the tablets of Example 13 is set forth below:

| Formula of Controlled Release MGBG 10 mg Tablets | | |
| --- | --- | --- |
| Component | mg/Tablet | % (by wt) |
| MGBG | 50.0 | 40.0 |
| Lactose (spray dried) | 29.25 | 23.4 |
| Povidone | 5.0 | 4.0 |
| EUDRAGIT ® RS 30D (solids) | 10.0* | 8.0 |
| TRIACETIN ® | 2.0 | 1.6 |
| Stearyl Alcohol | 25.0 | 20.0 |
| Talc | 2.5 | 2.0 |
| Magnesium Stearate | 1.25 | 1.0 |
| Total: | 125.0 | 100% |

*Approximately 33.33 mg EUDRAGIT ® RS 30D Aqueous dispersion is equivalent to 10 mg of EUDRAGIT ® RS 30D dry substance.

The tablets of Example 13 are then tested for dissolution via the USP Basket Method at 37° C., 100 RPM, first hour 700 ml simulated gastric fluid at pH 1.2, then changed to 900 ml at pH 7.5.

The formula for the tablets of Example 14 is set forth below:

| Formula of Controlled Release MGBG 20 mg Tablets | |
| --- | --- |
| Component | mg/Tablet |
| MGBG | 25.0 |
| Lactose (spray dried) | 54.25 |
| Povidone | 5.0 |
| EUDRAGIT ® RS 30D (solids) | 10.0* |
| TRIACETIN ® | 2.0 |
| Stearyl Alcohol | 25.0 |
| Talc | 2.5 |
| Magnesium Stearate | 1.25 |
| Total: | 125.0 |

The tablets of Example 14 are then tested for dissolution via the USP Basket Method at 37° C., 100 RPM, first hour 700 ml simulated gastric fluid at pH 1.2, then changed to 900 ml at pH 7.5.

EXAMPLES 15-16

In Example 15, 30 mg controlled release MGBG tablets are prepared according to the process set forth in Example 10. In Example 16, 10 mg controlled release MGBG tablets are prepared according to the process set forth in Example 12. Thereafter, dissolution studies of the tablets of Examples 5 and 6 are conducted at different pH levels, namely, pH 1.3, 4.56, 6.88 and 7.5.

EXAMPLES 17-22

In Examples 17-22, 4 mg and 10 mg MGBG tablets are prepared in a manner similar to the formulations and methods set forth in U.S. Pat. No. 4,990,341. In Example 17, MGBG (10.00 gm) is wet granulated with lactose monohydrate (417.5 gm) and hydroxyethyl cellulose (100.00 gm), and the granules are sieved through a 12 mesh screen. The granules are then dried in a fluid bed dryer at 50° C. and sieved through a 16 mesh screen. Molten cetostearyl alcohol (300.0 gm) is added to the warmed MGBG containing granules, and the whole was mixed thoroughly. The mixture is allowed to cool in the air, regranulated and sieved through a 16 mesh screen. Purified Talc (15.0 gm) and magnesium stearate (7.5 gm) are then added and mixed with the granules. The granules are then compressed into tablets.

Example 18 is prepared in the same manner as Example 17; however, the formulation includes 10 mg MGBG/tablet. The formulas for Examples 17 and 18 are set forth below.

FORMULATION OF EXAMPLE 17

| Ingredient | mg/tablet | g/batch |
| --- | --- | --- |
| MGBG | 4.0 | 10.0 |
| Lactose monohydrate | 167.0 | 417.5 |
| Hydroxyethylcellulose | 40.0 | 100.0 |
| Cetostearyl alcohol | 120.0 | 300.0 |
| Purified talc | 6.0 | 15.0 |
| Magnesium stearate | 3.0 | 7.5 |

FORMULATION OF EXAMPLE 18

| Ingredient | mg/tablet | g/batch |
|---|---|---|
| MGBG | 10.0 | 25.0 |
| Lactose monohydrate | 167.0 | 417.5 |
| Hydroxyethylcellulose | 40.0 | 100.0 |
| Cetostearyl alcohol | 120.0 | 300.0 |
| Talc | 6.0 | 15.0 |
| Magnesium stearate | 3.0 | 7.5 |

In Example 19, 4 mg MGBG controlled release tablets are prepared according to the excipient formula cited in Example 2 of U.S. Pat. No. 4,990,341. The method of manufacture is the same as set forth in Examples 17 and 18 above. Example 20 is prepared according to Example 19, except that 10 mg MGBG is included per tablet. The formulas for Examples 19 and 20 are set forth below.

FORMULATION OF EXAMPLE 19

| Ingredient | mg/tablet | g/batch |
|---|---|---|
| MGBG | 4.0 | 10.0 |
| Anhydrous Lactose | 167.0 | 417.5 |
| Hydroxyethylcellulose | 30.0 | 75.0 |
| Cetostearyl alcohol | 90.0 | 225.0 |
| Talc | 6.0 | 15.0 |
| Magnesium stearate | 3.0 | 7.5 |

FORMULATION OF EXAMPLE 20

| Ingredient | mg/tablet | g/batch |
|---|---|---|
| MGBG | 10.0 | 25.0 |
| Hydrous lactose | 167.0 | 417.5 |
| Hydroxyethylcellulose | 30.0 | 75.0 |
| Cetostearyl alcohol | 90.0 | 225.0 |
| Talc | 6.0 | 15.0 |
| Magnesium stearate | 3.0 | 7.5 |

In Example 21, MGBG 4 mg controlled release tablets are prepared in a manner analogous to, and with the same excipient formula cited in Example 3 of, U.S. Pat. No. 4,990,341.

MGBG (32.0 gm) is wet granulated with lactose monohydrate (240.0 gm) hydroxyethyl cellulose (80.0 gm) and methacrylic acid copolymer (240.0 gm, EUDRAGIT® L-100-55), and the granules are sieved through a 12 mesh screen. The granules are then dried in a Fluid Bed Dryer at 50° C. and passed through a 16 mesh screen.

To the warmed MGBG containing granules is added molten cetostearyl alcohol (240.0 gm), and the whole is mixed thoroughly. The mixture is allowed to cool in the air, regranulated and sieved through a 16 mesh screen. The granules are then compressed into tablets.

Example 22 is prepared in identical fashion to Example 21, except that 10 mg MGBG is included per tablet. The formulations for Examples 21 and 22 are set forth below.

FORMULATION OF EXAMPLE 21

| Ingredient | mg/tablet | g/batch |
|---|---|---|
| MGBG | 4.0 | 32.0 |
| Lactose monohydrate | 30.0 | 240.5 |
| Hydroxyethylcellulose | 10.0 | 80.0 |
| Methacrylic acid copolymer | 30.0 | 240.0 |
| Cetostearyl alcohol | 30.0 | 240.0 |

FORMULATION OF EXAMPLE 22

| Ingredient | mg/tablet | g/batch |
|---|---|---|
| MGBG | 10.0 | 80.0 |
| Lactose monohydrate | 30.0 | 240.5 |
| Hydroxyethylcellulose | 10.0 | 80.0 |
| Methacrylic acid copolymer | 30.0 | 240.0 |
| Cetostearyl alcohol | 30.0 | 240.0 |

Delayed-Release Enteric Coated Dosage Forms

EXAMPLE 23

Enteric Coated Capsule with Hypromellose/Microcrystalline Cellulose Pellet Core

| Ingredient | mg/capsule (250 mg MGBG dosage) |
|---|---|
| Pellet Core: | |
| MBGB | 250 |
| Microcrystalline cellulose | 75.07 |
| Hypromellose | 65 |
| Seal Coat: | |
| OPADRY® Clear | 6.5 |
| Enteric Coat: | |
| EUDRAGIT® L30-D55 | 71.77 |
| Triethyl Citrate | 2.15 |
| Sodium Hydroxide | 3.23 |
| Talc | 10.64 |
| Water* | NA |

EXAMPLE 24

Capsule Dosage Unit with Pellet Core and Delay Coat

| Ingredient | mg/capsule (250 mg MGBG dosage) |
|---|---|
| Pellet Core: | |
| MGBG | 250 |
| Microcrystalline cellulose | 75.07 |
| Hypromellose | 65 |
| Seal Coat: | |
| OPADRY ® Clear | 6.5 |
| "Delay" Coat: | |
| SURELEASE ® ethylcellulose dispersion | 27 |
| Hypomellose | 3 |
| Water* | NA |

EXAMPLE 25

Tablet Dosage Unit with Delay Coat

| Ingredient | mg/capsule (250 mg MGBG dosage) |
|---|---|
| Tablet Core: | |
| MGBG | 250 |
| Microcrystalline cellulose | 135 |
| Hypromellose | 60 |
| Talc | 18 |
| Magnesium stearate | 7 |
| "Delay" Coat: | |
| SURELEASE ® ethylcellulose dispersion | 27 |
| Hypomellose | 3 |
| Water* | NA |

EXAMPLE 26

Tablet Core with Enteric Coat

| Tablet Core: | |
|---|---|
| MGBG | 250 |
| Microcrystalline cellulose | 135 |
| Hypromellose | 60 |
| Talc | 18 |
| Magnesium stearate | 7 |
| Enteric ("delay") Coat: | |
| EUDRAGIT ® L30-D55 | 71.77 |
| Triethyl Citrate | 2.15 |
| Sodium Hydroxide | 3.23 |
| Talc | 10.64 |

EXAMPLES 27-506

Additional Enterically Coated Dosage Forms

Enterically coated dosage forms may be made by the methods below. In certain embodiments, methods are chosen so as to ensure that the final dosage form is substantially anhydrous. The moisture content can be measured by methods known in the art. Additionally, the dosage form may be tested for isomerization of MGBG. A stable dosage form would show minimal isomerization.

Tablets in the examples below may be made either by direct compression or by dry granulation. For manufacture by direct compression, MGBG in the amount cited is combined with magnesium stearate in an amount equal to about 1% of the total weight of the tablet core, crospovidone in an amount equal to about 2% of the total weight of the tablet core, and sufficient anhydrous lactose to form a tablet core of a total weight of 500 mg. The ingredients are de-lumped, by screening or milling, then blended until the mixture is substantially uniform. Unifomity may be tested by sampling at three different points in the blend container and assessing using standard methods such as HPLC; test result of 95-105% of target potency, with an RSD of 5% would be near ideal. The mixture is poured into dies, optionally with a forced-flow feeder, and compressed into tablets which may then be enterically coated.

For manufacture by dry granulation, MGBG in the amount cited, a disintegrant such as crospovidone and a lubricant such as magnesium stearate, and a sufficient amount of a filler/diluent such as anhydrous lactose to form a tablet core of a total weight of 500 mg (similar quantities of other excipients used in direct compression may be used, with adjustment to allow for an additional lubricating step at the end) are de-lumped by screening or milling, then blended until the mixture is substantially uniform. The mixture is poured into dies and compressed with a flat-faced punch into slugs, typically of ¾" to 1"; alternatively, the powder is densified by passing through the rollers of a compacting mill. The slugs are then broken up gently to form granules and reduced to a substantially uniform granule size by screening or milling. The granules are lubricated a second time. At this stage, the granules may themselves be enterically coated and then encapsulated, or compressed into tablets which may then be enterically coated.

For manufacture by spheronization, MGBG is combined with a binder/filler and wet granulated using a minimum of solvent according to methods known in the art. Microcrystalline cellulose is an appropriate binder. This mixture is passed through an extruder to form cylinders desired thickness. These cylindrical segments are collected and placed in a Marumerizer where they are shaped into spheroids by centrifugal and frictional forces. The spheroids should be screened for uniform size, such as roughly 0.5-1 mm in diameter. The spheroids may then be dried, lubricated, and enterically coated before being encapsulated. Alternatively, the spheroids may be compressed into a tablet which may then enterically coated.

For manufacture by micropeletization, MGBG is coated onto seed crystals of substantially uniform size, optionally after combining with a binder such as polyvinylpyrrolidone, in layers. The layers may be deposited by spraying the MGBG as a solution onto sugar seeds in an air column suspension unit, repeating the process as necessary until the micropellets are of the desired size. The micropellets may then be dried, lubricated, and enterically coated before being encapsulated.

EXAMPLES 27-212

Additional Enterically Coated Dosage Forms for Duodenal Release

The following Examples are enterically coated dosage forms made using a methacrylic acid/ethyl acrylate copolymer as the release-delaying agent in the enteric coat. The methacrylic acid/ethyl acrylate copolymer may be any such suitable copolymer, for example, EUDRAGIT® L 30 D-55 or EUDRAGIT® L 100-55. As formulated, the MGBG core of the tablet, micropellets, or spheroids may optionally be combined with one or more excipients as disclosed herein or known in the art. It is expected that the formulations below will bypass the stomach and release MGBG in the duodenum. Standard USP or in vitro assays as well as in vivo models which are known in the art may be used to confirm this effect. When using USP or in vitro models, it is expected that successful delayed-release dosage forms will dissolve between about pH 5.5 and about pH 6. When using in vivo models, it is expected that exceptionally successful delayed-release dosage forms will yield reduced gastrointestinal side effects, such as nausea, emesis, gastric irritation, ulceration, and/or bleeding, and loose stool and/or diarrhea, in subjects. It is also expected that the $T_{max}$ will be right-shifted (on a concentration-versus-time graph having concentration on the vertical axis and time on the horizontal axis, i.e., delayed) by at least one hour; in certain embodiments, the $T_{max}$ will be right-shifted by one to six hours.

Additionally, the amounts of MGBG may be varied as needed according to methods known in the art. Different proportions of MGBG and filler may be used to achieve, for example—using the same enteric coating proportions—a 50, 75, 100, 150, 200, 225, 325, 375, 400, or 450 mg dosage form. Additional excipients such as lubricants (for example talc), compression protectants (for example triethyl citrate or a polyethylene glycol such as macrogol 6000), etc. may be added. Table 3 below provides additional enterically coated dosage forms.

TABLE 3

| Ex. | MGBG Dose, mg | Enteric Coating | Enteric Coating as % of Total Weight of Formulation | Enteric Coating Applied To (Dosage Form) |
| --- | --- | --- | --- | --- |
| 27 | 250 | Methacrylic acid/ethyl acrylate copolymer | 1%-5% | tablet |
| 28 | 250 | Methacrylic acid/ethyl acrylate copolymer | 1%-2% | tablet |
| 29 | 250 | Methacrylic acid/ethyl acrylate copolymer | 2%-3% | tablet |
| 30 | 250 | Methacrylic acid/ethyl acrylate copolymer | 3%-4% | tablet |
| 31 | 250 | Methacrylic acid/ethyl acrylate copolymer | 4%-5% | tablet |
| 32 | 250 | Methacrylic acid/ethyl acrylate copolymer | 5%-10% | tablet |
| 33 | 250 | Methacrylic acid/ethyl acrylate copolymer | 5%-6% | tablet |
| 34 | 250 | Methacrylic acid/ethyl acrylate copolymer | 6%-7% | tablet |
| 35 | 250 | Methacrylic acid/ethyl acrylate copolymer | 7%-8% | tablet |
| 36 | 250 | Methacrylic acid/ethyl acrylate copolymer | 8%-9% | tablet |
| 37 | 250 | Methacrylic acid/ethyl acrylate copolymer | 9%-10% | tablet |
| 38 | 250 | Methacrylic acid/ethyl acrylate copolymer | 10%-15% | tablet |
| 39 | 250 | Methacrylic acid/ethyl acrylate copolymer | 10%-11% | tablet |
| 40 | 250 | Methacrylic acid/ethyl acrylate copolymer | 11%-12% | tablet |
| 41 | 250 | Methacrylic acid/ethyl acrylate copolymer | 12%-13% | tablet |
| 42 | 250 | Methacrylic acid/ethyl acrylate copolymer | 13%-14% | tablet |
| 43 | 250 | Methacrylic acid/ethyl acrylate copolymer | 14%-15% | tablet |
| 44 | 250 | Methacrylic acid/ethyl acrylate copolymer | 15%-20% | tablet |
| 45 | 250 | Methacrylic acid/ethyl acrylate copolymer | 20%-25% | tablet |
| 46 | 250 | Methacrylic acid/ethyl acrylate copolymer | 25%-30% | tablet |
| 47 | 250 | Methacrylic acid/ethyl acrylate copolymer | 1%-5% | capsule |
| 48 | 250 | Methacrylic acid/ethyl acrylate copolymer | 1%-2% | capsule |
| 49 | 250 | Methacrylic acid/ethyl acrylate copolymer | 2%-3% | capsule |
| 50 | 250 | Methacrylic acid/ethyl acrylate copolymer | 3%-4% | capsule |
| 51 | 250 | Methacrylic acid/ethyl acrylate copolymer | 4%-5% | capsule |
| 52 | 250 | Methacrylic acid/ethyl acrylate copolymer | 5%-10% | capsule |
| 53 | 250 | Methacrylic acid/ethyl acrylate copolymer | 5%-6% | capsule |
| 54 | 250 | Methacrylic acid/ethyl acrylate copolymer | 6%-7% | capsule |
| 55 | 250 | Methacrylic acid/ethyl acrylate copolymer | 7%-8% | capsule |
| 56 | 250 | Methacrylic acid/ethyl acrylate copolymer | 8%-9% | capsule |
| 57 | 250 | Methacrylic acid/ethyl acrylate copolymer | 9%-10% | capsule |
| 58 | 250 | Methacrylic acid/ethyl acrylate copolymer | 10%-15% | capsule |
| 59 | 250 | Methacrylic acid/ethyl acrylate copolymer | 10%-11% | capsule |
| 60 | 250 | Methacrylic acid/ethyl acrylate copolymer | 11%-12% | capsule |
| 61 | 250 | Methacrylic acid/ethyl acrylate copolymer | 12%-13% | capsule |
| 62 | 250 | Methacrylic acid/ethyl acrylate copolymer | 13%-14% | capsule |
| 63 | 250 | Methacrylic acid/ethyl acrylate copolymer | 14%-15% | capsule |
| 64 | 250 | Methacrylic acid/ethyl acrylate copolymer | 15%-20% | capsule |
| 65 | 250 | Methacrylic acid/ethyl acrylate copolymer | 20%-25% | capsule |
| 66 | 250 | Methacrylic acid/ethyl acrylate copolymer | 25%-30% | capsule |
| 67 | 250 | Methacrylic acid/ethyl acrylate copolymer | 1%-5% | micropellets (capsule) |
| 68 | 250 | Methacrylic acid/ethyl acrylate copolymer | 1%-2% | micropellets (capsule) |
| 69 | 250 | Methacrylic acid/ethyl acrylate copolymer | 2%-3% | micropellets (capsule) |
| 70 | 250 | Methacrylic acid/ethyl acrylate copolymer | 3%-4% | micropellets (capsule) |
| 71 | 250 | Methacrylic acid/ethyl acrylate copolymer | 4%-5% | micropellets (capsule) |
| 72 | 250 | Methacrylic acid/ethyl acrylate copolymer | 5%-10% | micropellets (capsule) |
| 73 | 250 | Methacrylic acid/ethyl acrylate copolymer | 5%-6% | micropellets (capsule) |
| 74 | 250 | Methacrylic acid/ethyl acrylate copolymer | 6%-7% | micropellets (capsule) |
| 75 | 250 | Methacrylic acid/ethyl acrylate copolymer | 7%-8% | micropellets (capsule) |
| 76 | 250 | Methacrylic acid/ethyl acrylate copolymer | 8%-9% | micropellets (capsule) |
| 77 | 250 | Methacrylic acid/ethyl acrylate copolymer | 9%-10% | micropellets (capsule) |
| 78 | 250 | Methacrylic acid/ethyl acrylate copolymer | 10%-15% | micropellets (capsule) |
| 79 | 250 | Methacrylic acid/ethyl acrylate copolymer | 10%-11% | micropellets (capsule) |
| 80 | 250 | Methacrylic acid/ethyl acrylate copolymer | 11%-12% | micropellets (capsule) |

TABLE 3-continued

| Ex. | MGBG Dose, mg | Enteric Coating | Enteric Coating as % of Total Weight of Formulation | Enteric Coating Applied To (Dosage Form) |
|---|---|---|---|---|
| 81 | 250 | Methacrylic acid/ethyl acrylate copolymer | 12%-13% | micropellets (capsule) |
| 82 | 250 | Methacrylic acid/ethyl acrylate copolymer | 13%-14% | micropellets (capsule) |
| 83 | 250 | Methacrylic acid/ethyl acrylate copolymer | 14%-15% | micropellets (capsule) |
| 84 | 250 | Methacrylic acid/ethyl acrylate copolymer | 15%-20% | micropellets (capsule) |
| 85 | 250 | Methacrylic acid/ethyl acrylate copolymer | 20%-25% | micropellets (capsule) |
| 86 | 250 | Methacrylic acid/ethyl acrylate copolymer | 25%-30% | micropellets (capsule) |
| 87 | 250 | Methacrylic acid/ethyl acrylate copolymer | 1%-5% | spheroids (capsule) |
| 88 | 250 | Methacrylic acid/ethyl acrylate copolymer | 1%-2% | spheroids (capsule) |
| 89 | 250 | Methacrylic acid/ethyl acrylate copolymer | 2%-3% | spheroids (capsule) |
| 90 | 250 | Methacrylic acid/ethyl acrylate copolymer | 3%-4% | spheroids (capsule) |
| 91 | 250 | Methacrylic acid/ethyl acrylate copolymer | 4%-5% | spheroids (capsule) |
| 92 | 250 | Methacrylic acid/ethyl acrylate copolymer | 5%-10% | spheroids (capsule) |
| 93 | 250 | Methacrylic acid/ethyl acrylate copolymer | 5%-6% | spheroids (capsule) |
| 94 | 250 | Methacrylic acid/ethyl acrylate copolymer | 6%-7% | spheroids (capsule) |
| 95 | 250 | Methacrylic acid/ethyl acrylate copolymer | 7%-8% | spheroids (capsule) |
| 96 | 250 | Methacrylic acid/ethyl acrylate copolymer | 8%-9% | spheroids (capsule) |
| 97 | 250 | Methacrylic acid/ethyl acrylate copolymer | 9%-10% | spheroids (capsule) |
| 98 | 250 | Methacrylic acid/ethyl acrylate copolymer | 10%-15% | spheroids (capsule) |
| 99 | 250 | Methacrylic acid/ethyl acrylate copolymer | 10%-11% | spheroids (capsule) |
| 100 | 250 | Methacrylic acid/ethyl acrylate copolymer | 11%-12% | spheroids (capsule) |
| 101 | 250 | Methacrylic acid/ethyl acrylate copolymer | 12%-13% | spheroids (capsule) |
| 102 | 250 | Methacrylic acid/ethyl acrylate copolymer | 13%-14% | spheroids (capsule) |
| 103 | 250 | Methacrylic acid/ethyl acrylate copolymer | 14%-15% | spheroids (capsule) |
| 104 | 250 | Methacrylic acid/ethyl acrylate copolymer | 15%-20% | spheroids (capsule) |
| 105 | 250 | Methacrylic acid/ethyl acrylate copolymer | 20%-25% | spheroids (capsule) |
| 106 | 250 | Methacrylic acid/ethyl acrylate copolymer | 25%-30% | spheroids (capsule) |
| 107 | 300 | Methacrylic acid/ethyl acrylate copolymer | 1%-5% | tablet |
| 108 | 300 | Methacrylic acid/ethyl acrylate copolymer | 1%-2% | tablet |
| 109 | 300 | Methacrylic acid/ethyl acrylate copolymer | 2%-3% | tablet |
| 110 | 300 | Methacrylic acid/ethyl acrylate copolymer | 3%-4% | tablet |
| 111 | 300 | Methacrylic acid/ethyl acrylate copolymer | 4%-5% | tablet |
| 112 | 300 | Methacrylic acid/ethyl acrylate copolymer | 5%-10% | tablet |
| 113 | 300 | Methacrylic acid/ethyl acrylate copolymer | 5%-6% | tablet |
| 114 | 300 | Methacrylic acid/ethyl acrylate copolymer | 6%-7% | tablet |
| 115 | 300 | Methacrylic acid/ethyl acrylate copolymer | 7%-8% | tablet |
| 116 | 300 | Methacrylic acid/ethyl acrylate copolymer | 8%-9% | tablet |
| 117 | 300 | Methacrylic acid/ethyl acrylate copolymer | 9%-10% | tablet |
| 118 | 300 | Methacrylic acid/ethyl acrylate copolymer | 10%-15% | tablet |
| 119 | 300 | Methacrylic acid/ethyl acrylate copolymer | 10%-11% | tablet |
| 120 | 300 | Methacrylic acid/ethyl acrylate copolymer | 11%-12% | tablet |
| 121 | 300 | Methacrylic acid/ethyl acrylate copolymer | 12%-13% | tablet |
| 122 | 300 | Methacrylic acid/ethyl acrylate copolymer | 13%-14% | tablet |
| 123 | 300 | Methacrylic acid/ethyl acrylate copolymer | 14%-15% | tablet |
| 124 | 300 | Methacrylic acid/ethyl acrylate copolymer | 15%-20% | tablet |
| 125 | 300 | Methacrylic acid/ethyl acrylate copolymer | 20%-25% | tablet |
| 126 | 300 | Methacrylic acid/ethyl acrylate copolymer | 25%-30% | tablet |
| 127 | 300 | Methacrylic acid/ethyl acrylate copolymer | 1%-5% | capsule |
| 128 | 300 | Methacrylic acid/ethyl acrylate copolymer | 1%-2% | capsule |
| 129 | 300 | Methacrylic acid/ethyl acrylate copolymer | 2%-3% | capsule |
| 130 | 300 | Methacrylic acid/ethyl acrylate copolymer | 3%-4% | capsule |
| 131 | 300 | Methacrylic acid/ethyl acrylate copolymer | 4%-5% | capsule |
| 132 | 300 | Methacrylic acid/ethyl acrylate copolymer | 5%-10% | capsule |
| 133 | 300 | Methacrylic acid/ethyl acrylate copolymer | 5%-6% | capsule |
| 134 | 300 | Methacrylic acid/ethyl acrylate copolymer | 6%-7% | capsule |
| 135 | 300 | Methacrylic acid/ethyl acrylate copolymer | 7%-8% | capsule |
| 136 | 300 | Methacrylic acid/ethyl acrylate copolymer | 8%-9% | capsule |
| 137 | 300 | Methacrylic acid/ethyl acrylate copolymer | 9%-10% | capsule |
| 138 | 300 | Methacrylic acid/ethyl acrylate copolymer | 10%-15% | capsule |
| 139 | 300 | Methacrylic acid/ethyl acrylate copolymer | 10%-11% | capsule |
| 140 | 300 | Methacrylic acid/ethyl acrylate copolymer | 11%-12% | capsule |
| 141 | 300 | Methacrylic acid/ethyl acrylate copolymer | 12%-13% | capsule |
| 142 | 300 | Methacrylic acid/ethyl acrylate copolymer | 13%-14% | capsule |
| 143 | 300 | Methacrylic acid/ethyl acrylate copolymer | 14%-15% | capsule |
| 144 | 300 | Methacrylic acid/ethyl acrylate copolymer | 15%-20% | capsule |
| 145 | 300 | Methacrylic acid/ethyl acrylate copolymer | 20%-25% | capsule |
| 146 | 300 | Methacrylic acid/ethyl acrylate copolymer | 25%-30% | capsule |
| 147 | 300 | Methacrylic acid/ethyl acrylate copolymer | 1%-5% | micropellets (capsule) |
| 148 | 300 | Methacrylic acid/ethyl acrylate copolymer | 1%-2% | micropellets (capsule) |
| 149 | 300 | Methacrylic acid/ethyl acrylate copolymer | 2%-3% | micropellets (capsule) |
| 150 | 300 | Methacrylic acid/ethyl acrylate copolymer | 3%-4% | micropellets (capsule) |
| 151 | 300 | Methacrylic acid/ethyl acrylate copolymer | 4%-5% | micropellets (capsule) |
| 152 | 300 | Methacrylic acid/ethyl acrylate copolymer | 5%-10% | micropellets (capsule) |
| 153 | 300 | Methacrylic acid/ethyl acrylate copolymer | 5%-6% | micropellets (capsule) |
| 154 | 300 | Methacrylic acid/ethyl acrylate copolymer | 6%-7% | micropellets (capsule) |

TABLE 3-continued

| Ex. | MGBG Dose, mg | Enteric Coating | Enteric Coating as % of Total Weight of Formulation | Enteric Coating Applied To (Dosage Form) |
|---|---|---|---|---|
| 155 | 300 | Methacrylic acid/ethyl acrylate copolymer | 7%-8% | micropellets (capsule) |
| 156 | 300 | Methacrylic acid/ethyl acrylate copolymer | 8%-9% | micropellets (capsule) |
| 157 | 300 | Methacrylic acid/ethyl acrylate copolymer | 9%-10% | micropellets (capsule) |
| 158 | 300 | Methacrylic acid/ethyl acrylate copolymer | 10%-15% | micropellets (capsule) |
| 159 | 300 | Methacrylic acid/ethyl acrylate copolymer | 10%-11% | micropellets (capsule) |
| 160 | 300 | Methacrylic acid/ethyl acrylate copolymer | 11%-12% | micropellets (capsule) |
| 161 | 300 | Methacrylic acid/ethyl acrylate copolymer | 12%-13% | micropellets (capsule) |
| 162 | 300 | Methacrylic acid/ethyl acrylate copolymer | 13%-14% | micropellets (capsule) |
| 163 | 300 | Methacrylic acid/ethyl acrylate copolymer | 14%-15% | micropellets (capsule) |
| 164 | 300 | Methacrylic acid/ethyl acrylate copolymer | 15%-20% | micropellets (capsule) |
| 165 | 300 | Methacrylic acid/ethyl acrylate copolymer | 20%-25% | micropellets (capsule) |
| 166 | 300 | Methacrylic acid/ethyl acrylate copolymer | 25%-30% | micropellets (capsule) |
| 167 | 300 | Methacrylic acid/ethyl acrylate copolymer | 1%-5% | spheroids (capsule) |
| 168 | 300 | Methacrylic acid/ethyl acrylate copolymer | 1%-2% | spheroids (capsule) |
| 169 | 300 | Methacrylic acid/ethyl acrylate copolymer | 2%-3% | spheroids (capsule) |
| 170 | 300 | Methacrylic acid/ethyl acrylate copolymer | 3%-4% | spheroids (capsule) |
| 171 | 300 | Methacrylic acid/ethyl acrylate copolymer | 4%-5% | spheroids (capsule) |
| 172 | 300 | Methacrylic acid/ethyl acrylate copolymer | 5%-10% | spheroids (capsule) |
| 173 | 300 | Methacrylic acid/ethyl acrylate copolymer | 5%-6% | spheroids (capsule) |
| 174 | 300 | Methacrylic acid/ethyl acrylate copolymer | 6%-7% | spheroids (capsule) |
| 175 | 300 | Methacrylic acid/ethyl acrylate copolymer | 7%-8% | spheroids (capsule) |
| 176 | 300 | Methacrylic acid/ethyl acrylate copolymer | 8%-9% | spheroids (capsule) |
| 177 | 300 | Methacrylic acid/ethyl acrylate copolymer | 9%-10% | spheroids (capsule) |
| 178 | 300 | Methacrylic acid/ethyl acrylate copolymer | 10%-15% | spheroids (capsule) |
| 179 | 300 | Methacrylic acid/ethyl acrylate copolymer | 10%-11% | spheroids (capsule) |
| 180 | 300 | Methacrylic acid/ethyl acrylate copolymer | 11%-12% | spheroids (capsule) |
| 181 | 300 | Methacrylic acid/ethyl acrylate copolymer | 12%-13% | spheroids (capsule) |
| 182 | 300 | Methacrylic acid/ethyl acrylate copolymer | 13%-14% | spheroids (capsule) |
| 183 | 300 | Methacrylic acid/ethyl acrylate copolymer | 14%-15% | spheroids (capsule) |
| 184 | 300 | Methacrylic acid/ethyl acrylate copolymer | 15%-20% | spheroids (capsule) |
| 185 | 300 | Methacrylic acid/ethyl acrylate copolymer | 20%-25% | spheroids (capsule) |
| 186 | 300 | Methacrylic acid/ethyl acrylate copolymer | 25%-30% | spheroids (capsule) |
| 187 | 350 | Methacrylic acid/ethyl acrylate copolymer | 1%-5% | tablet |
| 188 | 350 | Methacrylic acid/ethyl acrylate copolymer | 1%-2% | tablet |
| 189 | 350 | Methacrylic acid/ethyl acrylate copolymer | 2%-3% | tablet |
| 190 | 350 | Methacrylic acid/ethyl acrylate copolymer | 3%-4% | tablet |
| 191 | 350 | Methacrylic acid/ethyl acrylate copolymer | 4%-5% | tablet |
| 192 | 350 | Methacrylic acid/ethyl acrylate copolymer | 5%-10% | tablet |
| 193 | 350 | Methacrylic acid/ethyl acrylate copolymer | 5%-6% | tablet |
| 194 | 350 | Methacrylic acid/ethyl acrylate copolymer | 6%-7% | tablet |
| 195 | 350 | Methacrylic acid/ethyl acrylate copolymer | 7%-8% | tablet |
| 196 | 350 | Methacrylic acid/ethyl acrylate copolymer | 8%-9% | tablet |
| 197 | 350 | Methacrylic acid/ethyl acrylate copolymer | 9%-10% | tablet |
| 198 | 350 | Methacrylic acid/ethyl acrylate copolymer | 10%-15% | tablet |
| 199 | 350 | Methacrylic acid/ethyl acrylate copolymer | 10%-11% | tablet |
| 200 | 350 | Methacrylic acid/ethyl acrylate copolymer | 11%-12% | tablet |
| 201 | 350 | Methacrylic acid/ethyl acrylate copolymer | 12%-13% | tablet |
| 202 | 350 | Methacrylic acid/ethyl acrylate copolymer | 13%-14% | tablet |
| 203 | 350 | Methacrylic acid/ethyl acrylate copolymer | 14%-15% | tablet |
| 204 | 350 | Methacrylic acid/ethyl acrylate copolymer | 15%-20% | tablet |
| 205 | 350 | Methacrylic acid/ethyl acrylate copolymer | 20%-25% | tablet |
| 206 | 350 | Methacrylic acid/ethyl acrylate copolymer | 25%-30% | tablet |
| 207 | 350 | Methacrylic acid/ethyl acrylate copolymer | 1%-5% | capsule |
| 208 | 350 | Methacrylic acid/ethyl acrylate copolymer | 1%-2% | capsule |
| 209 | 350 | Methacrylic acid/ethyl acrylate copolymer | 2%-3% | capsule |
| 210 | 350 | Methacrylic acid/ethyl acrylate copolymer | 3%-4% | capsule |
| 211 | 350 | Methacrylic acid/ethyl acrylate copolymer | 4%-5% | capsule |
| 212 | 350 | Methacrylic acid/ethyl acrylate copolymer | 5%-10% | capsule |
| 213 | 350 | Methacrylic acid/ethyl acrylate copolymer | 5%-6% | capsule |
| 214 | 350 | Methacrylic acid/ethyl acrylate copolymer | 6%-7% | capsule |
| 215 | 350 | Methacrylic acid/ethyl acrylate copolymer | 7%-8% | capsule |
| 216 | 350 | Methacrylic acid/ethyl acrylate copolymer | 8%-9% | capsule |
| 217 | 350 | Methacrylic acid/ethyl acrylate copolymer | 9%-10% | capsule |
| 218 | 350 | Methacrylic acid/ethyl acrylate copolymer | 10%-15% | capsule |
| 219 | 350 | Methacrylic acid/ethyl acrylate copolymer | 10%-11% | capsule |
| 220 | 350 | Methacrylic acid/ethyl acrylate copolymer | 11%-12% | capsule |
| 221 | 350 | Methacrylic acid/ethyl acrylate copolymer | 12%-13% | capsule |
| 222 | 350 | Methacrylic acid/ethyl acrylate copolymer | 13%-14% | capsule |
| 223 | 350 | Methacrylic acid/ethyl acrylate copolymer | 14%-15% | capsule |
| 224 | 350 | Methacrylic acid/ethyl acrylate copolymer | 15%-20% | capsule |
| 225 | 350 | Methacrylic acid/ethyl acrylate copolymer | 20%-25% | capsule |
| 226 | 350 | Methacrylic acid/ethyl acrylate copolymer | 25%-30% | capsule |
| 227 | 350 | Methacrylic acid/ethyl acrylate copolymer | 1%-5% | micropellets (capsule) |
| 228 | 350 | Methacrylic acid/ethyl acrylate copolymer | 1%-2% | micropellets (capsule) |

TABLE 3-continued

| Ex. | MGBG Dose, mg | Enteric Coating | Enteric Coating as % of Total Weight of Formulation | Enteric Coating Applied To (Dosage Form) |
|---|---|---|---|---|
| 229 | 350 | Methacrylic acid/ethyl acrylate copolymer | 2%-3% | micropellets (capsule) |
| 230 | 350 | Methacrylic acid/ethyl acrylate copolymer | 3%-4% | micropellets (capsule) |
| 231 | 350 | Methacrylic acid/ethyl acrylate copolymer | 4%-5% | micropellets (capsule) |
| 232 | 350 | Methacrylic acid/ethyl acrylate copolymer | 5%-10% | micropellets (capsule) |
| 233 | 350 | Methacrylic acid/ethyl acrylate copolymer | 5%-6% | micropellets (capsule) |
| 234 | 350 | Methacrylic acid/ethyl acrylate copolymer | 6%-7% | micropellets (capsule) |
| 235 | 350 | Methacrylic acid/ethyl acrylate copolymer | 7%-8% | micropellets (capsule) |
| 236 | 350 | Methacrylic acid/ethyl acrylate copolymer | 8%-9% | micropellets (capsule) |
| 237 | 350 | Methacrylic acid/ethyl acrylate copolymer | 9%-10% | micropellets (capsule) |
| 238 | 350 | Methacrylic acid/ethyl acrylate copolymer | 10%-15% | micropellets (capsule) |
| 239 | 350 | Methacrylic acid/ethyl acrylate copolymer | 10%-11% | micropellets (capsule) |
| 240 | 350 | Methacrylic acid/ethyl acrylate copolymer | 11%-12% | micropellets (capsule) |
| 241 | 350 | Methacrylic acid/ethyl acrylate copolymer | 12%-13% | micropellets (capsule) |
| 242 | 350 | Methacrylic acid/ethyl acrylate copolymer | 13%-14% | micropellets (capsule) |
| 243 | 350 | Methacrylic acid/ethyl acrylate copolymer | 14%-15% | micropellets (capsule) |
| 244 | 350 | Methacrylic acid/ethyl acrylate copolymer | 15%-20% | micropellets (capsule) |
| 245 | 350 | Methacrylic acid/ethyl acrylate copolymer | 20%-25% | micropellets (capsule) |
| 246 | 350 | Methacrylic acid/ethyl acrylate copolymer | 25%-30% | micropellets (capsule) |
| 247 | 350 | Methacrylic acid/ethyl acrylate copolymer | 1%-5% | spheroids (capsule) |
| 248 | 350 | Methacrylic acid/ethyl acrylate copolymer | 1%-2% | spheroids (capsule) |
| 249 | 350 | Methacrylic acid/ethyl acrylate copolymer | 2%-3% | spheroids (capsule) |
| 250 | 350 | Methacrylic acid/ethyl acrylate copolymer | 3%-4% | spheroids (capsule) |
| 251 | 350 | Methacrylic acid/ethyl acrylate copolymer | 4%-5% | spheroids (capsule) |
| 252 | 350 | Methacrylic acid/ethyl acrylate copolymer | 5%-10% | spheroids (capsule) |
| 253 | 350 | Methacrylic acid/ethyl acrylate copolymer | 5%-6% | spheroids (capsule) |
| 254 | 350 | Methacrylic acid/ethyl acrylate copolymer | 6%-7% | spheroids (capsule) |
| 255 | 350 | Methacrylic acid/ethyl acrylate copolymer | 7%-8% | spheroids (capsule) |
| 256 | 350 | Methacrylic acid/ethyl acrylate copolymer | 8%-9% | spheroids (capsule) |
| 257 | 350 | Methacrylic acid/ethyl acrylate copolymer | 9%-10% | spheroids (capsule) |
| 258 | 350 | Methacrylic acid/ethyl acrylate copolymer | 10%-15% | spheroids (capsule) |
| 259 | 350 | Methacrylic acid/ethyl acrylate copolymer | 10%-11% | spheroids (capsule) |
| 260 | 350 | Methacrylic acid/ethyl acrylate copolymer | 11%-12% | spheroids (capsule) |
| 261 | 350 | Methacrylic acid/ethyl acrylate copolymer | 12%-13% | spheroids (capsule) |
| 262 | 350 | Methacrylic acid/ethyl acrylate copolymer | 13%-14% | spheroids (capsule) |
| 263 | 350 | Methacrylic acid/ethyl acrylate copolymer | 14%-15% | spheroids (capsule) |
| 264 | 350 | Methacrylic acid/ethyl acrylate copolymer | 15%-20% | spheroids (capsule) |
| 265 | 350 | Methacrylic acid/ethyl acrylate copolymer | 20%-25% | spheroids (capsule) |
| 266 | 350 | Methacrylic acid/ethyl acrylate copolymer | 25%-30% | spheroids (capsule) |

EXAMPLES 267-506

Additional Enterically Coated Dosage Forms for Jejunal Release

Examples 267-506 are enterically coated dosage forms which can be made in proportions analogous to each corresponding Example among those in Examples 27-266, but using a methacrylic acid/methyl methacrylate copolymer ("MA/MM-C") as the release-delaying agent in the enteric coat instead of a methacrylic acid/ethyl acrylate copolymer. The methacrylic acid/methyl methacrylate copolymer may be any such suitable copolymer, for example, EUDRAGIT® L 100 or EUDRAGIT® L 12.5. As formulated, the MGBG core of the tablet, micropellets, or spheroids may optionally be combined with one or more excipients as disclosed herein or known in the art. It is expected that the formulations below will bypass the stomach and release MGBG primarily in the jejunum. Standard USP or in vitro assays as well as in vivo models which are known in the art may be used to confirm this effect. When using USP or in vitro models, it is expected that successful delayed-release dosage forms will dissolve between about pH 6 and about pH 7. When using in vivo models, it is expected that exceptionally successful delayed-release dosage forms will yield reduced gastrointestinal side effects, such as nausea, emesis, gastric irritation, ulceration, and/or bleeding, and loose stool and/or diarrhea, in subjects. It is also expected that the $T_{max}$ will be right-shifted (on a concentration-versus-time graph having concentration on the vertical axis and time on the horizontal axis, i.e., delayed) by at least two hours; in certain embodiments, the $T_{max}$ will be right-shifted by two to twelve hours.

Additionally, the amounts of MGBG may be varied as needed according to methods known in the art. Different proportions of MGBG and filler may be used to achieve, for example—using the same enteric coating proportions—a 50, 75, 100, 150, 200, 225, 325, 375, 400, or 450 mg dosage form. Additional excipients such as lubricants (for example talc), compression protectants (for example triethyl citrate or a polyethylene glycol such as macrogol 6000), etc. may be added. Table 4 below provides additional enterically coated dosage forms.

TABLE 4

| Ex. | MGBG Dose, mg | MA/MM-C Enteric Coating as % of Total Weight of Formulation | Enteric Coating on Dosage Form: |
|---|---|---|---|
| 267 | 250 | 1%-5% | tablet |
| 268 | 250 | 1%-2% | tablet |
| 269 | 250 | 2%-3% | tablet |
| 270 | 250 | 3%-4% | tablet |
| 271 | 250 | 4%-5% | tablet |
| 272 | 250 | 5%-10% | tablet |
| 273 | 250 | 5%-6% | tablet |
| 274 | 250 | 6%-7% | tablet |

TABLE 4-continued

| Ex. | MGBG Dose, mg | MA/MM-C Enteric Coating as % of Total Weight of Formulation | Enteric Coating on Dosage Form: |
|---|---|---|---|
| 275 | 250 | 7%-8% | tablet |
| 276 | 250 | 8%-9% | tablet |
| 277 | 250 | 9%-10% | tablet |
| 278 | 250 | 10%-15% | tablet |
| 279 | 250 | 10%-11% | tablet |
| 280 | 250 | 11%-12% | tablet |
| 281 | 250 | 12%-13% | tablet |
| 282 | 250 | 13%-14% | tablet |
| 283 | 250 | 14%-15% | tablet |
| 284 | 250 | 15%-20% | tablet |
| 285 | 250 | 20%-25% | tablet |
| 286 | 250 | 25%-30% | tablet |
| 287 | 250 | 1%-5% | capsule |
| 288 | 250 | 1%-2% | capsule |
| 289 | 250 | 2%-3% | capsule |
| 290 | 250 | 3%-4% | capsule |
| 291 | 250 | 4%-5% | capsule |
| 292 | 250 | 5%-10% | capsule |
| 293 | 250 | 5%-6% | capsule |
| 294 | 250 | 6%-7% | capsule |
| 295 | 250 | 7%-8% | capsule |
| 296 | 250 | 8%-9% | capsule |
| 297 | 250 | 9%-10% | capsule |
| 298 | 250 | 10%-15% | capsule |
| 299 | 250 | 10%-11% | capsule |
| 300 | 250 | 11%-12% | capsule |
| 301 | 250 | 12%-13% | capsule |
| 302 | 250 | 13%-14% | capsule |
| 303 | 250 | 14%-15% | capsule |
| 304 | 250 | 15%-20% | capsule |
| 305 | 250 | 20%-25% | capsule |
| 306 | 250 | 25%-30% | capsule |
| 307 | 250 | 1%-5% | micropellets (capsule) |
| 308 | 250 | 1%-2% | micropellets (capsule) |
| 309 | 250 | 2%-3% | micropellets (capsule) |
| 310 | 250 | 3%-4% | micropellets (capsule) |
| 311 | 250 | 4%-5% | micropellets (capsule) |
| 312 | 250 | 5%-10% | micropellets (capsule) |
| 313 | 250 | 5%-6% | micropellets (capsule) |
| 314 | 250 | 6%-7% | micropellets (capsule) |
| 315 | 250 | 7%-8% | micropellets (capsule) |
| 316 | 250 | 8%-9% | micropellets (capsule) |
| 317 | 250 | 9%-10% | micropellets (capsule) |
| 318 | 250 | 10%-15% | micropellets (capsule) |
| 319 | 250 | 10%-11% | micropellets (capsule) |
| 320 | 250 | 11%-12% | micropellets (capsule) |
| 321 | 250 | 12%-13% | micropellets (capsule) |
| 322 | 250 | 13%-14% | micropellets (capsule) |
| 323 | 250 | 14%-15% | micropellets (capsule) |
| 324 | 250 | 15%-20% | micropellets (capsule) |
| 325 | 250 | 20%-25% | micropellets (capsule) |
| 326 | 250 | 25%-30% | micropellets (capsule) |
| 327 | 250 | 1%-5% | spheroids (capsule) |
| 328 | 250 | 1%-2% | spheroids (capsule) |
| 329 | 250 | 2%-3% | spheroids (capsule) |
| 330 | 250 | 3%-4% | spheroids (capsule) |
| 331 | 250 | 4%-5% | spheroids (capsule) |
| 332 | 250 | 5%-10% | spheroids (capsule) |
| 333 | 250 | 5%-6% | spheroids (capsule) |
| 334 | 250 | 6%-7% | spheroids (capsule) |
| 335 | 250 | 7%-8% | spheroids (capsule) |
| 336 | 250 | 8%-9% | spheroids (capsule) |
| 337 | 250 | 9%-10% | spheroids (capsule) |
| 338 | 250 | 10%-15% | spheroids (capsule) |
| 339 | 250 | 10%-11% | spheroids (capsule) |
| 340 | 250 | 11%-12% | spheroids (capsule) |
| 341 | 250 | 12%-13% | spheroids (capsule) |
| 342 | 250 | 13%-14% | spheroids (capsule) |
| 343 | 250 | 14%-15% | spheroids (capsule) |
| 344 | 250 | 15%-20% | spheroids (capsule) |
| 345 | 250 | 20%-25% | spheroids (capsule) |
| 346 | 250 | 25%-30% | spheroids (capsule) |
| 347 | 300 | 1%-5% | tablet |
| 348 | 300 | 1%-2% | tablet |
| 349 | 300 | 2%-3% | tablet |
| 350 | 300 | 3%-4% | tablet |
| 351 | 300 | 4%-5% | tablet |
| 352 | 300 | 5%-10% | tablet |
| 353 | 300 | 5%-6% | tablet |
| 354 | 300 | 6%-7% | tablet |
| 355 | 300 | 7%-8% | tablet |
| 356 | 300 | 8%-9% | tablet |
| 357 | 300 | 9%-10% | tablet |
| 358 | 300 | 10%-15% | tablet |
| 359 | 300 | 10%-11% | tablet |
| 360 | 300 | 11%-12% | tablet |
| 361 | 300 | 12%-13% | tablet |
| 362 | 300 | 13%-14% | tablet |
| 363 | 300 | 14%-15% | tablet |
| 364 | 300 | 15%-20% | tablet |
| 365 | 300 | 20%-25% | tablet |
| 366 | 300 | 25%-30% | tablet |
| 367 | 300 | 1%-5% | capsule |
| 368 | 300 | 1%-2% | capsule |
| 369 | 300 | 2%-3% | capsule |
| 370 | 300 | 3%-4% | capsule |
| 371 | 300 | 4%-5% | capsule |
| 372 | 300 | 5%-10% | capsule |
| 373 | 300 | 5%-6% | capsule |
| 374 | 300 | 6%-7% | capsule |
| 375 | 300 | 7%-8% | capsule |
| 376 | 300 | 8%-9% | capsule |
| 377 | 300 | 9%-10% | capsule |
| 378 | 300 | 10%-15% | capsule |
| 379 | 300 | 10%-11% | capsule |
| 380 | 300 | 11%-12% | capsule |
| 381 | 300 | 12%-13% | capsule |
| 382 | 300 | 13%-14% | capsule |
| 383 | 300 | 14%-15% | capsule |
| 384 | 300 | 15%-20% | capsule |
| 385 | 300 | 20%-25% | capsule |
| 386 | 300 | 25%-30% | capsule |
| 387 | 300 | 1%-5% | micropellets (capsule) |
| 388 | 300 | 1%-2% | micropellets (capsule) |
| 389 | 300 | 2%-3% | micropellets (capsule) |
| 390 | 300 | 3%-4% | micropellets (capsule) |
| 391 | 300 | 4%-5% | micropellets (capsule) |
| 392 | 300 | 5%-10% | micropellets (capsule) |
| 393 | 300 | 5%-6% | micropellets (capsule) |
| 394 | 300 | 6%-7% | micropellets (capsule) |
| 395 | 300 | 7%-8% | micropellets (capsule) |
| 396 | 300 | 8%-9% | micropellets (capsule) |
| 397 | 300 | 9%-10% | micropellets (capsule) |
| 398 | 300 | 10%-15% | micropellets (capsule) |
| 399 | 300 | 10%-11% | micropellets (capsule) |
| 400 | 300 | 11%-12% | micropellets (capsule) |
| 401 | 300 | 12%-13% | micropellets (capsule) |
| 402 | 300 | 13%-14% | micropellets (capsule) |
| 403 | 300 | 14%-15% | micropellets (capsule) |
| 404 | 300 | 15%-20% | micropellets (capsule) |
| 405 | 300 | 20%-25% | micropellets (capsule) |
| 406 | 300 | 25%-30% | micropellets (capsule) |
| 407 | 300 | 1%-5% | spheroids (capsule) |
| 408 | 300 | 1%-2% | spheroids (capsule) |
| 409 | 300 | 2%-3% | spheroids (capsule) |
| 410 | 300 | 3%-4% | spheroids (capsule) |
| 411 | 300 | 4%-5% | spheroids (capsule) |
| 412 | 300 | 5%-10% | spheroids (capsule) |
| 413 | 300 | 5%-6% | spheroids (capsule) |
| 414 | 300 | 6%-7% | spheroids (capsule) |
| 415 | 300 | 7%-8% | spheroids (capsule) |
| 416 | 300 | 8%-9% | spheroids (capsule) |
| 417 | 300 | 9%-10% | spheroids (capsule) |
| 418 | 300 | 10%-15% | spheroids (capsule) |
| 419 | 300 | 10%-11% | spheroids (capsule) |
| 420 | 300 | 11%-12% | spheroids (capsule) |
| 421 | 300 | 12%-13% | spheroids (capsule) |
| 422 | 300 | 13%-14% | spheroids (capsule) |
| 423 | 300 | 14%-15% | spheroids (capsule) |
| 424 | 300 | 15%-20% | spheroids (capsule) |
| 425 | 300 | 20%-25% | spheroids (capsule) |
| 426 | 300 | 25%-30% | spheroids (capsule) |

TABLE 4-continued

| Ex. | MGBG Dose, mg | MA/MM-C Enteric Coating as % of Total Weight of Formulation | Enteric Coating on Dosage Form: |
|---|---|---|---|
| 427 | 350 | 1%-5% | tablet |
| 428 | 350 | 1%-2% | tablet |
| 429 | 350 | 2%-3% | tablet |
| 430 | 350 | 3%-4% | tablet |
| 431 | 350 | 4%-5% | tablet |
| 432 | 350 | 5%-10% | tablet |
| 433 | 350 | 5%-6% | tablet |
| 434 | 350 | 6%-7% | tablet |
| 435 | 350 | 7%-8% | tablet |
| 436 | 350 | 8%-9% | tablet |
| 437 | 350 | 9%-10% | tablet |
| 438 | 350 | 10%-15% | tablet |
| 439 | 350 | 10%-11% | tablet |
| 440 | 350 | 11%-12% | tablet |
| 441 | 350 | 12%-13% | tablet |
| 442 | 350 | 13%-14% | tablet |
| 443 | 350 | 14%-15% | tablet |
| 444 | 350 | 15%-20% | tablet |
| 445 | 350 | 20%-25% | tablet |
| 446 | 350 | 25%-30% | tablet |
| 447 | 350 | 1%-5% | capsule |
| 448 | 350 | 1%-2% | capsule |
| 449 | 350 | 2%-3% | capsule |
| 450 | 350 | 3%-4% | capsule |
| 451 | 350 | 4%-5% | capsule |
| 452 | 350 | 5%-10% | capsule |
| 453 | 350 | 5%-6% | capsule |
| 454 | 350 | 6%-7% | capsule |
| 455 | 350 | 7%-8% | capsule |
| 456 | 350 | 8%-9% | capsule |
| 457 | 350 | 9%-10% | capsule |
| 458 | 350 | 10%-15% | capsule |
| 459 | 350 | 10%-11% | capsule |
| 460 | 350 | 11%-12% | capsule |
| 461 | 350 | 12%-13% | capsule |
| 462 | 350 | 13%-14% | capsule |
| 463 | 350 | 14%-15% | capsule |
| 464 | 350 | 15%-20% | capsule |
| 465 | 350 | 20%-25% | capsule |
| 466 | 350 | 25%-30% | capsule |
| 467 | 350 | 1%-5% | micropellets (capsule) |
| 468 | 350 | 1%-2% | micropellets (capsule) |
| 469 | 350 | 2%-3% | micropellets (capsule) |
| 470 | 350 | 3%-4% | micropellets (capsule) |
| 471 | 350 | 4%-5% | micropellets (capsule) |
| 472 | 350 | 5%-10% | micropellets (capsule) |
| 473 | 350 | 5%-6% | micropellets (capsule) |
| 474 | 350 | 6%-7% | micropellets (capsule) |
| 475 | 350 | 7%-8% | micropellets (capsule) |
| 476 | 350 | 8%-9% | micropellets (capsule) |
| 477 | 350 | 9%-10% | micropellets (capsule) |
| 478 | 350 | 10%-15% | micropellets (capsule) |
| 479 | 350 | 10%-11% | micropellets (capsule) |
| 480 | 350 | 11%-12% | micropellets (capsule) |
| 481 | 350 | 12%-13% | micropellets (capsule) |
| 482 | 350 | 13%-14% | micropellets (capsule) |
| 483 | 350 | 14%-15% | micropellets (capsule) |
| 484 | 350 | 15%-20% | micropellets (capsule) |
| 485 | 350 | 20%-25% | micropellets (capsule) |
| 486 | 350 | 25%-30% | micropellets (capsule) |
| 487 | 350 | 1%-5% | spheroids (capsule) |
| 488 | 350 | 1%-2% | spheroids (capsule) |
| 489 | 350 | 2%-3% | spheroids (capsule) |
| 490 | 350 | 3%-4% | spheroids (capsule) |
| 491 | 350 | 4%-5% | spheroids (capsule) |
| 492 | 350 | 5%-10% | spheroids (capsule) |
| 493 | 350 | 5%-6% | spheroids (capsule) |
| 494 | 350 | 6%-7% | spheroids (capsule) |
| 495 | 350 | 7%-8% | spheroids (capsule) |
| 496 | 350 | 8%-9% | spheroids (capsule) |
| 497 | 350 | 9%-10% | spheroids (capsule) |
| 498 | 350 | 10%-15% | spheroids (capsule) |
| 499 | 350 | 10%-11% | spheroids (capsule) |
| 500 | 350 | 11%-12% | spheroids (capsule) |
| 501 | 350 | 12%-13% | spheroids (capsule) |
| 502 | 350 | 13%-14% | spheroids (capsule) |
| 503 | 350 | 14%-15% | spheroids (capsule) |
| 504 | 350 | 15%-20% | spheroids (capsule) |
| 505 | 350 | 20%-25% | spheroids (capsule) |
| 506 | 350 | 25%-30% | spheroids (capsule) |

Further analogous examples for release in the colon may be made by substituting ethyl acrylate/methyl methacrylate/methacrylic acid copolymer as the release-delaying agent in the enteric coat instead of a methacrylic acid/ethyl acrylate or methacrylic acid/methyl methacrylate copolymer copolymer. The ethyl acrylate/methyl methacrylate/methacrylic acid copolymer may be any such suitable copolymer, for example, EUDRAGIT® S 100, EUDRAGIT® S 12.5 or EUDRAGIT® FS 30-D. As formulated, the MGBG core of the tablet, micropellets, or spheroids may optionally be combined with one or more excipients as disclosed herein or known in the art. It is expected that the formulations below will bypass the stomach and release MGBG primarily in the colon. Standard USP or in vitro assays as well as in vivo models which are known in the art may be used to confirm this effect. When using USP or in vitro models, it is expected that successful delayed-release dosage forms will dissolve above about pH 7. When using in vivo models, it is expected that exceptionally successful delayed-release dosage forms will yield reduced gastrointestinal side effects, such as nausea, emesis, gastric irritation, ulceration, and/or bleeding, and loose stool and/or diharrhea, in subjects. It is also expected that the $T_{max}$ will be right-shifted (on a concentration-versus-time graph having concentration on the vertical axis and time on the horizontal axis, i.e., delayed) by at least three hours; in certain embodiments, the $T_{max}$ will be right-shifted by three to twenty-four hours.

EXAMPLE 507

Enterically Coated Capsules for Delayed Release

MGBG was encapsulated neat (undiluted) using Torpac gelatin capsules. Methylglyoxal bis (guanylhydrazone) dihydrochloride hydrate (MGBG), was used; a correction factor of 1.49 (to account for the dihydrochloride salt/monohydrate) was used when calculating the required amount of test article. The amount in each capsule was 10, 30, or 100 mg/kg, calculated based on subject body weight. Capsules were enterically coated with EUDRAGIT® L100-55, as required, using a Torpac "ProCoater" coating apparatus according to the standard dip procedure provided by the manufacturer (see www.torpac.com, go to "Reference/ProCoater Manual.pdf" or contact Torpac, Inc. for detailed instructions).

COMPARATIVE EXAMPLES

Immediate-Release Dosage Forms

Solid MGBG or a salt thereof may be passed through one or more sieve screens to produce a consistent particle size. Excipients, too, may be passed through a sieve. Appropriate weights of compounds, sufficient to achieve the target dosage per capsule, may be measured and added to a mixing container or apparatus, and the blend is then mixed until uniform. Blend uniformity testing may be done by, for example, sampling 3 points within the container (top, middle, and bottom) and testing each sample for potency. A test result of 95-105% of target, with an RSD of 5%, would be considered ideal; optionally, additional blend time may be allowed to achieve a uniform blend. Upon acceptable blend uniformity results, a measured aliquot of this stock formulation may be separated to manufacture the lower strengths. Magnesium stearate may be passed through a sieve, collected, weighed, added to the blender as a lubricant, and mixed until dispersed. The final blend is weighed and reconciled. Capsules may then be opened and blended materials flood fed into the body of the capsules using a spatula. Capsules in trays may be tamped to settle the blend in each capsule to assure uniform target fill weight, then sealed by combining the filled bodies with the caps.

COMPARATIVE EXAMPLE C1

300 mg Capsule

Total fill weight of capsule is 500 mg, not including capsule weight. Target compound dosage is 300 mg per capsule, but may be adjusted to account for the weight of counterions and/or solvates if given as a salt or solvated polymorph thereof. In such a case the weight of the other excipients, typically the filler, is reduced.

| Ingredient | Quantity per Capsule, mg |
| --- | --- |
| MGBG | 300.00 |
| Lactose monohydrate | 179.00 |
| Silicon dioxide | 3.00 |
| Crospovidone | 15.00 |
| Magnesium stearate (vegetable grade) | 3.00 |

COMPARATIVE EXAMPLE C2

150 mg Capsule

Total fill weight of capsule is 300 mg, not including capsule weight. Target compound dosage is 150 mg per capsule, but may be adjusted to account for the weight of counterions and/or solvates if given as a salt or solvated polymorph thereof. In such a case the weight of the other excipients, typically the filler, is reduced.

| Ingredient | Quantity per Capsule, mg |
| --- | --- |
| MGBG | 150 |
| Microcrystalline cellulose (MCC) | 147 |
| Magnesium stearate (vegetable grade) | 3 |

It is expected that when tested in humans or animals, the comparative immediate-release examples above will exhibit several of the following characteristics when compared to a controlled-release dosage form: shorter half life, higher $C_{max}$, shorter $T_{max}$, and higher frequency and/or severity of side effects including gastrointestinal side effects.

In Vivo Evaluation of Enterically Coated Capsules

A comparative study of single, escalating doses of enterically coated MGBG capsules was undertaken in order to ascertain the feasibility and pharmacologic effect of delaying release of MGBG until the capsule has passed the stomach. The dog was selected as the test species, both because it is typically the most gastrointestinally sensitive species and because it has consistently demonstrated dose-limiting emesis upon oral administration of standard capsules containing MGBG. Six male beagle dogs aged approximately 4 years 8 months to 5 years 6 months and weighing 10.95 to 12.85 kg (Covance Research Products) were weighed, acclimatized, and randomly assigned to treatment groups as shown below in Table 5.

TABLE 5

| | | No. of Animals | |
| --- | --- | --- | --- |
| Group No. | Dose, mpk | Standard Capsule | Enterically-Coated Capsule |
| 1 | 10 | 3 | — |
| 2 | 10 | — | 3 |
| 3 | 30 | 3 | — |
| 4 | 30 | — | 3 |
| 5 | 100 | 3 | — |
| 6 | 100 | — | 3 |

The test article was administered once at each dose level during the study orally via capsule. Duplicate sets of enteric-coated capsules were prepared for each animal at each dose and evaluated for dissolution. The duplicate sample was placed in a 0.1 N HCl solution, and stirred using a magnetic stir bar and stir plate, for at least two hours. Triplicate samples of the acidic dissolution media were collected for analysis of MGBG content. The capsule was transferred to a phosphate buffer solution (pH 6.8), and stirred using a magnetic stir bar and stir plate, for approximately one hour. The capsule was visually inspected for signs of deformation. If dissolution criteria were not met—≤10% the concentration of the capsule in solution; visual inspection showing deformation of the capsule and release of the product—the enteric-coated capsule preparation was repeated in duplicate, until the results of the duplicate test met the study requirements. Non-enterically coated (immediate release) reference capsules were also prepared.

Dose levels were selected on the basis of previous studies in dogs, which exhibited dose-limiting emesis when administered single doses of MGBG in standard capsules ≥10 mg/kg. The dose levels for the treated groups were 10, 30, and 100 mg/kg administered on Days 1, 8, and 33, respectively, in standard or enteric coated gelatin capsules. Individual doses were based on the most recent body weights. The animals were administered the next escalating dose of the test article after the completion of a 7 day (between doses 1 and 2) or 25 day (between doses 2 and 3) wash-out period.

Observations for morbidity, mortality, injury, and the availability of food and water were conducted twice daily for all animals. Observations for clinical signs were conducted pre-dose and at 0.25, 0.5, 0.75, 1, 1.25, 1.5, 1.75, 2, 4, 8, and 24 hours postdose on Days 1, 8, and 33, and daily on non-dosing days. On occasion, clinical observations were recorded at unscheduled intervals. Body weights were measured and recorded on Days 1-4, 5, 12, and 32.

Sample Collection and Handling.

Blood samples (approximately 1 mL) were collected from all animals for determination of the plasma concentrations of the test article. Samples were collected predose and at 0.5, 1, 2, 4, 8, and 24 hours postdose on Day 1, and predose and at 0.5, 1, 2, 4, 8, 12, 18, and 24 hours postdose on Days 8 and 33. The animals were not fasted prior to blood collection. Samples were placed in tubes containing lithium heparin as an anticoagulant. The blood samples were collected on wet ice and centrifuged for 10 minutes at 3000 g RCF under refrigeration at 4° C. At study termination, all animals were euthanized.

Analysis.

Plasma samples were separated into two aliquots (approximately 200 μL per aliquot) following centrifugation and placed in tightly capped, pre-labeled, plastic vials and were stored frozen at −50 to −90° C. until analyzed. The vial label included the study number, relative study day, animal number, and the date and time interval of collection.

Pharmacodynamic Results.

One objective of this study was to compare tolerability and systemic exposure when the test article was administered by standard versus enteric-coated gelatin capsules. All dose levels were tolerated with all animals surviving to study termination. MGBG-related clinical observations, with the highest incidence for salivation and emesis/vomitus, were primarily noted in the dogs administered standard capsules and most notably at 100 mg/kg/day. Enteric coating of MGBG capsules therefore appeared to be effective in preventing gastrointestinal adverse effects. See Table 6 below.

TABLE 6

| Dose Level (mpk) | Incidence of Emesis from Standard Capsules (%) | Incidence of Emesis from Enteric-Coated Capsules (%) |
| --- | --- | --- |
| 10 | 0 (0) | 0 (0) |
| 30 | 2 (67) | 1 (33) |
| 100 | 3 (100) | 0 (0) |

Pharmacokinetic Results.

Figure 2:
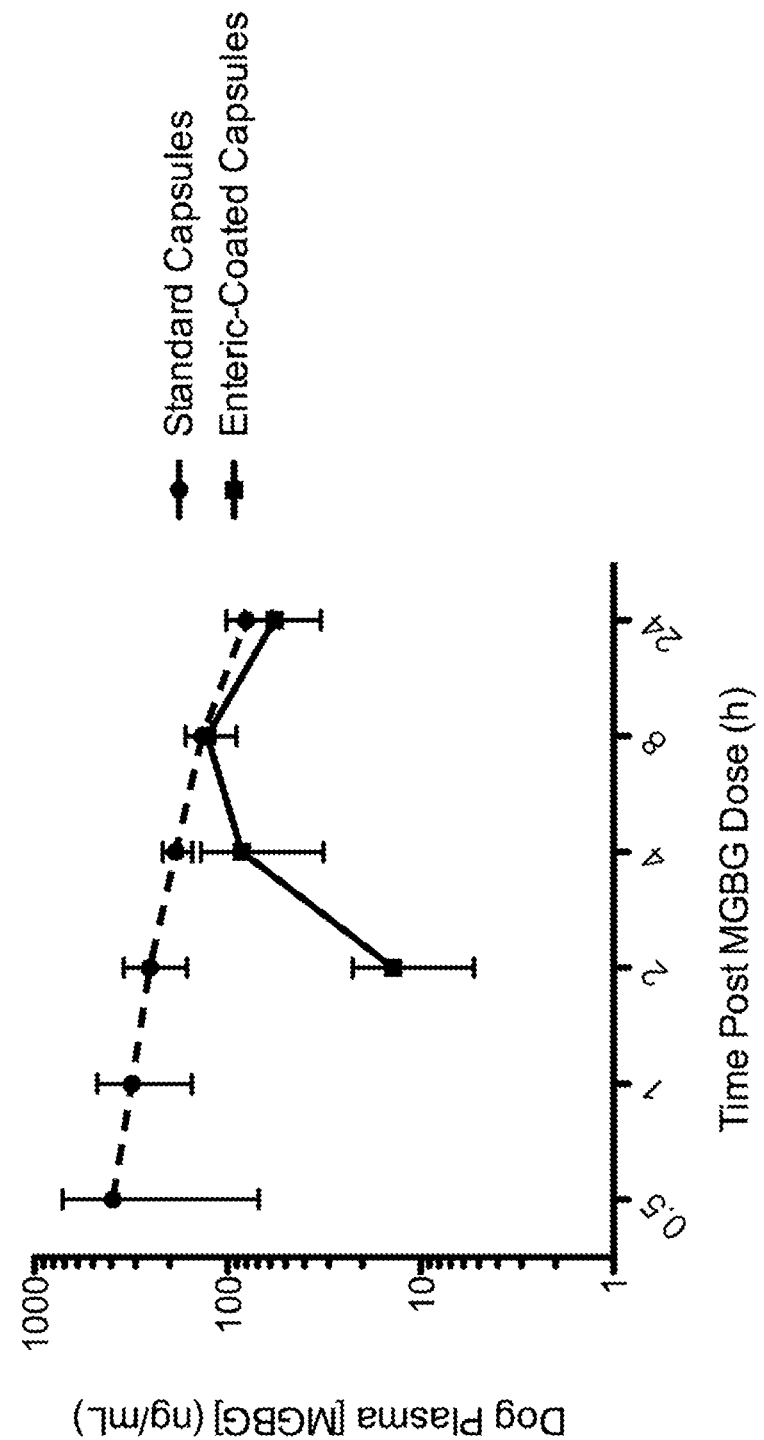
FIG. 2 depicts the time-versus-drug-concentration curves for standard and enterically-coated capsules in dogs, dosed at 10 mg/kg.
Figure 3:
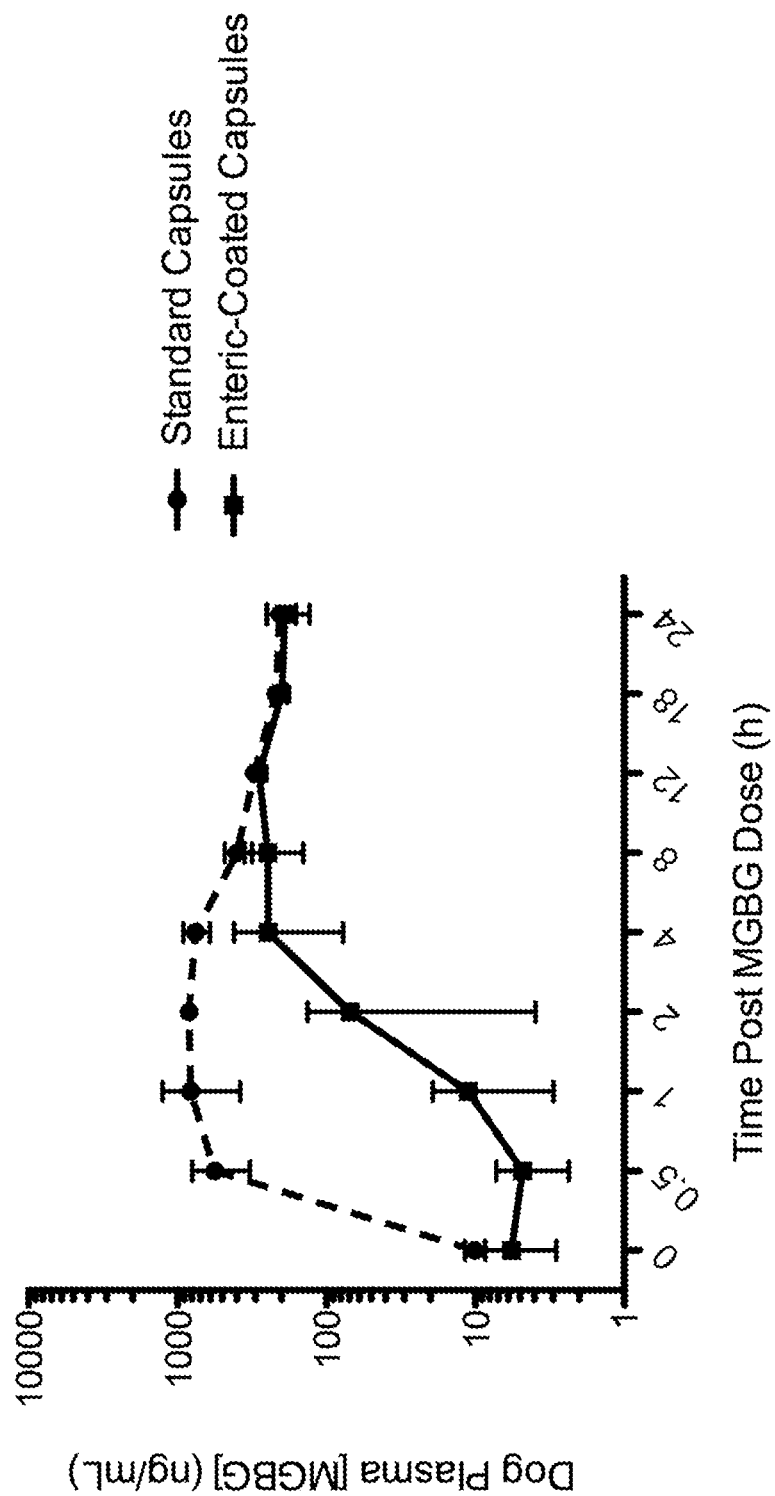
FIG. 3 depicts the time-versus-drug-concentration curves for standard and enterically-coated capsules in dogs, dosed at 30 mg/kg.
Figure 4:
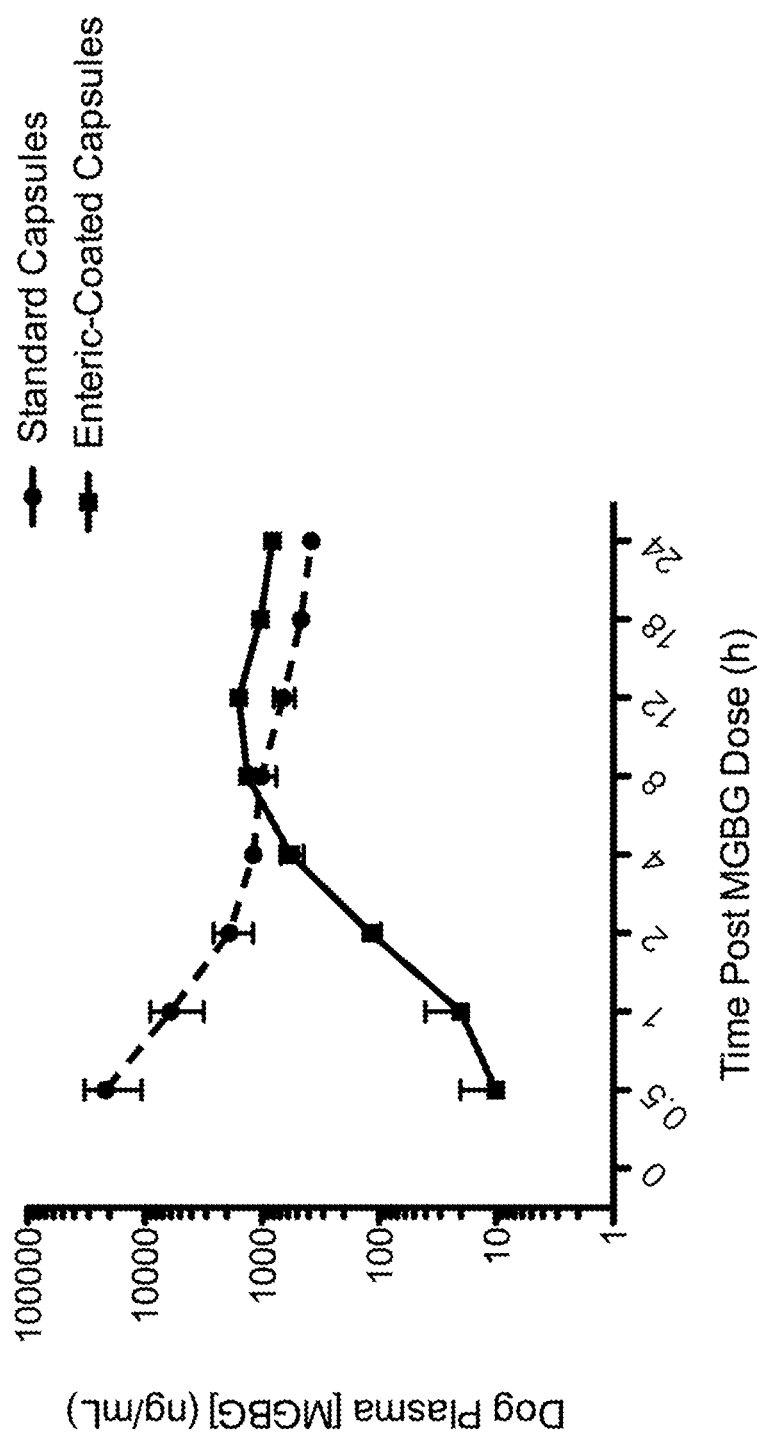
FIG. 4 depicts the time-versus-drug-concentration curves for standard and enterically-coated capsules in dogs, dosed at 100 mg/kg.
Figure 5:
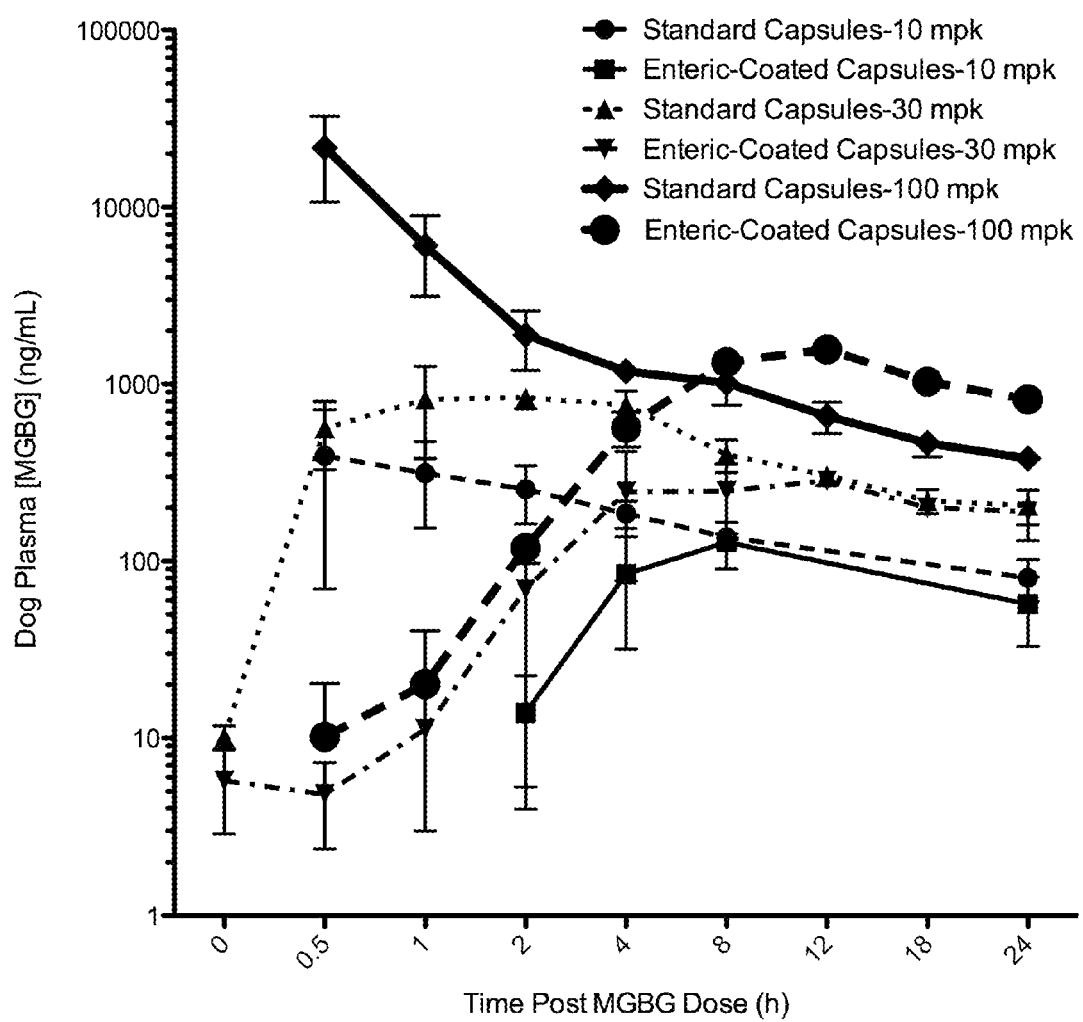
FIG. 5 depicts the time-versus-drug-concentration curves for standard and enterically-coated capsules in dogs, at all tested doses (10, 30, and 100 mg/kg).

Mean time-versus-concentration curves for standard and enterically coated capsules are presented in FIG. 2 (10 mg/kg), FIG. 3 (30 mg/kg) and FIG. 4 (100 mg/kg) and FIG. 5 (all doses on same axes). Plasma concentrations with the standard capsules generally declined rapidly during the first 4 hours and then gradually from 4 to 24 hours, while plasma concentrations with the enteric-coated capsules increased slowly from 0 to 8 (or 12) hours, and then declined gradually. Measurable concentrations were observed after 24-hours in all groups and both capsule types. $T_{max}$ ranged from 2.33 to 3.5 hours for standard capsules, and from 8 to 13.3 hours for enteric-coated capsules. Mean $C_{max}$ and mean $AUC_{0-t}$ exposure to MGBG increased with increasing dose for both capsule types. $C_{max}$ was sometimes greater than dose-proportional with the standard capsule and dose-proportional with the enteric-coated capsules. $AUC_{0-t}$ was dose-proportional for both capsule types. The dogs dosed with the standard capsules had higher mean exposures at all dose levels, compared to dogs dosed with the enteric-coated capsules, even at 100 mg/kg/day with the incidence of emesis/vomitus. $C_{max}$ for the standard capsule ranged from 510 to 22,090 ng/mL, and 128 to 1,580 ng/mL for the enteric-coated capsules. $AUC_{0-t}$ for the standard capsule ranged from 3,370 to 33,000 ng·hr/mL, and 2,010 to 23,700 ng·hr/mL for the enteric-coated capsules. Mean data and standard deviations are given below in Table 7; see also FIG. 6 where $T_{max}$ and $C_{max}$ are compared across doses.

TABLE 7

| Dose (mg/kg) | $T_{max}$ (h) | $C_{max}$ (ng/mL) | $AUC_{0-t}$ (ng * hr/mL) |
| --- | --- | --- | --- |
| 10 mg/kg Standard | 3.50 ± 3.97 | 510 ± 492 | 3370 ± 1210 |
| 10 mg/kg Enteric | 8 | 128 ± 65 | 2010 ± 1240 |
| 30 mg/kg Standard | 2.33 ± 1.53 | 1200 ± 456 | 9500 ± 1780 |
| 30 mg/kg Enteric | 13.3 ± 10.1 | 403 ± 150 | 5040 ± 1640 |
| 100 mg/kg Standard | 3.00 ± 4.33 | 22090 ± 18392 | 33000 ± 12922 |
| 100 mg/kg Enteric | 10.7 ± 2.31 | 1580 ± 413 | 23700 ± 4100 |

Comparison of mean $AUC_{0-t}$ between the enteric-coated capsules and standard capsules within dose groups resulted in relative bioavailability estimates that ranged from 53.1% to 71.8%. Dose proportionality was also analyzed. The ratio of high to low mean $C_{max}$/Dose values was found to be 5.3 across the standard capsule dosages and 1.2 across the same dosages in enterically-coated capsules. In contrast, the ratio of high to low mean $AUC_{0-t}$/Dose (relative bioavailability) values was found to be 1.1 across the standard capsule dosages and 1.4 across the same dosages in enterically-coated capsules. This indicates that MGBG exhibited greater than dose-proportional changes in $C_{max}$ after administration of the standard capsule and dose-proportional increases in $C_{max}$ with dose for the enteric-coated capsule.

All references cited herein are incorporated by reference as if written herein in their entireties. U.S. Pat. Nos. U.S. Pat. No. 4,587,118, U.S. Pat. No. 6,274,171, U.S. Pat. No. 4,966,768, U.S. Pat. No. 6,874,207, and U.S. Pat. No. 5,508,042, as well as Remington: the Science and Practice of Pharmacy, 21$^{st}$ Ed., Am J Pharm Educ. 2006 Jun. 15; 70(3): 71, are explicitly incorporated by reference as if written herein.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating pain comprising the administration, to a patient in need thereof, a delayed-release oral pharmaceutical dosage form comprising MGBG.

2. The method as recited in claim 1, wherein said delayed release oral pharmaceutical dosage form is an enterically-coated capsule comprising MGBG.

3. The method as recited in claim 2, wherein the administration of the enterically-coated capsule comprising MGBG results in a reduction of gastrointestinal side effects when compared to a reference standard that is not enterically coated.

4. The method as recited in claim 3, wherein said gastrointestinal side effects are chosen from nausea, emesis, diarrhea, abdominal pain, oral mucositis, oral ulceration, pharyngitis, stomatitis, irritation of the gastric mucosa, and gastrointestinal ulceration.

5. The method as recited in claim 4, wherein said gastrointestinal side effect is emesis.

6. The method as recited in claim 3, wherein MGBG is administered at a dosage level which would result in dose-limiting side effects if administered as a non-enteric coated dosage form.

* * * * *